US010930167B2

(12) United States Patent
Upchurch, Jr.

(10) Patent No.: US 10,930,167 B2
(45) Date of Patent: Feb. 23, 2021

(54) SOUND ASSOCIATION TEST

(71) Applicant: Upchurch & Associates Inc., Fort Worth, TX (US)

(72) Inventor: Jesse L. Upchurch, Jr., Fort Worth, TX (US)

( * ) Notice: Subject to any disclaimer, the term of this patent is extended or adjusted under 35 U.S.C. 154(b) by 1097 days.

(21) Appl. No.: 15/182,285

(22) Filed: Jun. 14, 2016

(65) Prior Publication Data

US 2016/0367179 A1 Dec. 22, 2016

Related U.S. Application Data

(60) Provisional application No. 62/180,225, filed on Jun. 16, 2015.

(51) Int. Cl.
| | |
|---|---|
| A61B 5/16 | (2006.01) |
| G09B 5/06 | (2006.01) |
| A61B 5/024 | (2006.01) |
| A61B 5/0533 | (2021.01) |
| A61B 5/145 | (2006.01) |

(52) U.S. Cl.
CPC .............. *G09B 5/065* (2013.01); *A61B 5/162* (2013.01); *A61B 5/167* (2013.01); *A61B 5/024* (2013.01); *A61B 5/0533* (2013.01); *A61B 5/14542* (2013.01)

(58) Field of Classification Search
CPC ..................................................... G09B 5/065
USPC ........................................................ 434/236
See application file for complete search history.

(56) References Cited

U.S. PATENT DOCUMENTS

| | | | | |
|---|---|---|---|---|
| 5,393,236 A | * | 2/1995 | Blackmer | G09B 7/04 434/169 |
| 6,006,188 A | * | 12/1999 | Bogdashevsky | G10L 17/26 704/270 |
| 6,026,361 A | * | 2/2000 | Hura | G10L 25/69 704/200 |
| 2008/0071136 A1 | * | 3/2008 | Oohashi | A61M 21/02 600/27 |
| 2008/0184206 A1 | * | 7/2008 | Vikutan | G06F 11/3688 717/127 |
| 2009/0018407 A1 | * | 1/2009 | Jung | A61B 3/113 600/301 |
| 2012/0071785 A1 | * | 3/2012 | Forbes | G16H 10/20 600/558 |

(Continued)

*Primary Examiner* — David L Lewis
*Assistant Examiner* — Shauna-Kay Hall
(74) *Attorney, Agent, or Firm* — Kir

(57) ABSTRACT

An auditory projective test is provided that emphasizes a shift in focus from visual and verbal/linguistic stimuli to an examination of the phenomena of acoustic and sonic association. The design discovers a "canon" of sound stimuli that may provide psychological associations with the aim to further inform and compliment the findings of Jung's word association test. The design includes a computer software program that gathers and calculates data in Excel format. Jung's traditional Word Association test is presented alongside the sound association test. The design may include the use of digital video recording to help observe and demonstrate behavioral responses. Additionally, the design may include the addition of a digital interface that will reintroduce the measurement of certain physiological data originally used in Jung's association experiments.

10 Claims, 18 Drawing Sheets

(56) References Cited

U.S. PATENT DOCUMENTS

2012/0090446 A1* 4/2012 Moreno ................. G09B 15/00
                                                                               84/470 R
2012/0144455 A1* 6/2012 Lazar ..................... G06F 21/31
                                                                                726/4
2017/0046971 A1* 2/2017 Moreno ................. G09B 19/00

* cited by examiner

FIG. 5

| | |
|---|---|
| Median for words 1-50: | 15.0 |
| Responses Over PM | 20 |
| Repeated SWs: | 0 |
| SWs with noise: | 6 |
| SWs with failed repro: | 8 |
| Rhymes or completions: | 3 |
| Multi-word responses: | 1 |
| Mis-heard SW: | 0 |
| Responses with gestures: | 14 |
| Perseverations: | 0 |
| No response in 30s: | 0 |
| Stereotypes: Around(5);Many(4),often (5) | |
| Mediate responses: | 0 |
| Meaningless responses: | 0 |
| Defensive reactions: | 0 |
| Slip of the tongue: | 0 |
| Foreign language: | 0 |
| Stutter/mispronunciation: | 0 |
| Factual Responses: | 25 |
| Egocentric Responses: | 25 |

FIG. 7

SUBJECT 6 SOUNDS

| Sound Number | Stimulus Sounds | Reaction Time 5ths | Reaction Time 100ths | Reaction | Reproduction | Reaction Notes | Complex Indicator Types | | | | Type of Response | | |
|---|---|---|---|---|---|---|---|---|---|---|---|---|---|
| | | | | | | | Over PM | repeat | noise | other | GS | Factual | Egocentric |
| 1 | AMB_Bayle | 18 | 360 | Bells | + | | | ✓ | | 0 | | | |
| 2 | AN_bird | 20 | 396 | Jungle | + | | | | | 0 | | | |
| 3 | HU_sick | 18 | 358 | Coughing | - | Sick | | | | 0 | | | |
| 4 | OB_phone | 18 | 353 | Not again | - | | | | | MWR,GS | | | |
| 5 | NA_river | 19 | 378 | River | + | | | ✓ | | GS | | | |
| 6 | OB_door | 30 | 596 | Dungeon | + | | ✓ | | ✓ | GS | | | |
| 7 | AMB_Diaz16 | 24 | 485 | Footsteps | + | Footsteps | | | ✓ | 0 | | | |
| 8 | AN_rooster | 26 | 510 | Chores | + | | | | | GS | | | |
| 9 | UR_traffic | 27 | 531 | 5oclock | + | | | | | GS | | | |
| 10 | OB_cooking | 20 | 401 | Breakfast | + | | | | | 0 | | | |
| 11 | HU_sing | 32 | 639 | Indian | + | | ✓ | | | GS | | | |
| 12 | AMB_Gobeil | 57 | 1135 | Solitary | - | Isolation | ✓ | | | 0 | | | |
| 13 | HU_laugh | 27 | 531 | Party | + | | | | | 0 | | | |
| 14 | AN_dog | 31 | 618 | Neighborhood | - | Black | ✓ | | | GS | | | |
| 15 | HU_walk | 30 | 607 | Walking on leaves | - | Secret | ✓ | | | MWR | | | |
| 16 | NA_rain | 26 | 529 | Shower | + | | | | | RC | | | |
| 17 | AMB_Diaz19 | 40 | 799 | UfO | + | | ✓ | | | GS | | | |
| 18 | AN_cow | 30 | 598 | Cattle | + | | ✓ | ✓ | | GS | | | |
| 19 | HU_sex | 51 | 1015 | Good | + | | ✓ | | | GS | | | |
| 20 | AN_wolf | 35 | 694 | Lonely | - | Lonesome | ✓ | | | 0 | | | |
| 21 | OB_bells | 18 | 360 | Mass | + | | | | | 0 | | | |
| 22 | HU_bride | 42 | 833 | Wedding | - | Marry | ✓ | | | GS | | | |
| 23 | AN_pig | 33 | 653 | Sty; pigsty | + | Pigsty | ✓ | | | RC,MWR | | | |
| 24 | HU_applause | 14 | 279 | Concert | + | | | | | 0 | | | |
| 25 | UR_siren | 16 | 313 | Danger | + | | | | | 0 | | | |
| 26 | NA_thunderstorm | 23 | 457 | Peaceful | + | | | | | 0 | | | |
| 27 | AMB_beno | 34 | 679 | Insane | - | Insane asylum | ✓ | | | MWR,GS | | | |
| 28 | AN_owl | 27 | 547 | Nighttime | + | | | | | 0 | | | |
| 29 | HU_kiss | 30 | 600 | Kissing | + | | ✓ | ✓ | | GS | | | |
| 30 | OB_ice | 28 | 558 | Cocktail | + | | | | | GS | | | |
| 31 | NA_wind | 37 | 734 | Desert | + | | ✓ | | | 0 | | | |
| 32 | AMB_Diaz22 | 33 | 664 | Floating | + | | ✓ | | | GS | | | |
| 33 | UR_train | 24 | 483 | Cargo | + | | | | ✓ | GS | | | |
| 34 | OB_shots | 19 | 384 | War | + | | | | ✓ | 0 | | | |
| 35 | HU_scream | 35 | 697 | Torture | + | | ✓ | | | GS | | | |
| 36 | UR_accident | 43 | 859 | Oh...accident | - | Hurt | ✓ | ✓ | ✓ | GS | | | |
| 37 | UR_siren | 12 | 246 | Help | + | | | | | 0 | | | |
| 38 | AN_cat | 23 | 460 | Kitty cat | + | | | | ✓ | 0 | | | |
| 39 | HU_laugh | 23 | 469 | Park | + | | | | | 0 | | | |
| 40 | OB_teapot | 20 | 390 | Teatime | + | | | | | 0 | | | |
| 41 | NA_waves | 53 | 1060 | Distance | - | Ocean | ✓ | | | 0 | | | |
| 42 | UR_airport | 15 | 296 | Late | + | | | | | 0 | | | |
| 43 | AMB_Diaz15 | 22 | 448 | Electric | - | Electronic | | | | 0 | | | |
| 44 | AN_crickets | 23 | 459 | Rainforest | - | Pond | | | | 0 | | | |
| 45 | HU_breath | 15 | 300 | Out of breath | + | | | | | MWR | | | |
| 46 | OB_ship | 32 | 646 | Fog | + | | ✓ | | | 0 | | | |
| 47 | UR_jackhammer | 18 | 357 | Construction | + | | | | | 0 | | | |
| 48 | AMB_Diaz16 | 31 | 612 | Marching | - | Footsteps | ✓ | | | 0 | | | |
| 49 | AN_frog | 23 | 466 | Pond | - | Rainforest | | | | GS | | | |
| 50 | SCN_storm | 38 | 753 | Voyage | - | Night trip | ✓ | | | GS | | | |

Median for sounds 1-50: 26.5

Responses Over PM: 21
Repeated SWs: 5
SWs with noise: 6
SWs with failed repro: 14
Rhymes or completions: 2
Multi-word responses: 5
Mis-heard SW: 0
Responses with gestures: 20
Perseverations: 0
No response in 30s: 0
Stereotypes: Footsteps
Mediate responses: 0
Meaningless responses: 0
Defensive reactions: 0
Slip of the tongue: 0
Foreign language: 0
Stutter/mispronunciation: 0

Factual Responses: 24
Egocentric Responses: 26

*FIG. 17*

SUBJECT 6 WORDS

| Word Number | Stimulus Word | Reaction Time 5ths | Reaction Time 100ths | Reaction | Reproduction | Reaction Notes | Complex Indicator Types - Over PM | repeat | noise | other | Type of Response - Factual | Egocentric |
|---|---|---|---|---|---|---|---|---|---|---|---|---|
| 1 | Play | 13 | 262 | Around | + | Around | | | | 0 | | |
| 2 | Mouth | 14 | 283 | Heart | + | | | | | GS | | |
| 3 | Free | 14 | 271 | Dom | + | | | | | RC,GS | | |
| 4 | Car | 15 | 293 | Pet | - | Wreck | | | | RC | | |
| 5 | Make | 13 | 254 | More | + | | | | | 0 | | |
| 6 | Friend | 28 | 552 | Many | + | Many | ✓ | | | ST,GS | | |
| 7 | Stupid | 22 | 445 | Idiot | + | | ✓ | | ✓ | GS | | |
| 8 | Together | 19 | 378 | Again | + | | ✓ | | | 0 | | |
| 9 | Go | 15 | 290 | Away | + | | | | | 0 | | |
| 10 | Habit | 20 | 402 | Forming | - | Monk | ✓ | | | 0 | | |
| 11 | New | 16 | 322 | Old | + | | | | | 0 | | |
| 12 | Tree | 17 | 336 | Of life | + | | ✓ | | | MWR | | |
| 13 | Kiss | 13 | 256 | Often | + | Often | | | | ST | | |
| 14 | Finger | 14 | 281 | Pointing | + | | | | | 0 | | |
| 15 | Sad | 24 | 480 | Happy | + | | ✓ | | ✓ | GS | | |
| 16 | Knife | 21 | 427 | Cut | + | | ✓ | | | 0 | | |
| 17 | Dance | 20 | 402 | Around | + | Around | ✓ | | ✓ | GS,ST | | |
| 18 | Choice | 14 | 280 | Many | + | Many | | | | 0 | | |
| 19 | Naked | 14 | 287 | Woman | + | | | | | 0 | | |
| 20 | Plain | 16 | 319 | Jane | + | | | | | 0 | | |
| 21 | Learn | 17 | 341 | A lot | - | Often | ✓ | | | GS | | |
| 22 | Pity | 11 | 216 | Party | + | | | | | RC | | |
| 23 | Weak | 17 | 336 | Strong | + | | ✓ | | | 0 | | |
| 24 | Boss | 21 | 426 | None | + | | ✓ | | | GS | | |
| 25 | Wait | 18 | 351 | Around | + | Around | ✓ | | | ST | | |
| 26 | Family | 14 | 279 | Good | - | Mine | | | | 0 | | |
| 27 | Sick | 14 | 286 | Hospital | + | | | | | 0 | | |
| 28 | Cat | 12 | 244 | Good | + | | | | | GS | | |
| 29 | Pray | 13 | 266 | Often | + | Often | | | | ST | | |
| 30 | Wages | 13 | 250 | More | + | | | | | 0 | | |
| 31 | Old | 12 | 233 | Men | + | | | | | 0 | | |
| 32 | Fight | 24 | 487 | No | - | Who | ✓ | | | 0 | | |
| 33 | Glass | 10 | 205 | House | + | | | | | 0 | | |
| 34 | Marry | 28 | 563 | Wedding | + | | ✓ | | ✓ | GS | | |
| 35 | Guilt | 10 | 198 | Shame | + | | | | | 0 | | |
| 36 | Work | 12 | 242 | A lot | + | | | | | GS | | |
| 37 | Proud | 12 | 237 | Father | + | | | | | 0 | | |
| 38 | Fear | 15 | 293 | Night | - | Nighttime | | | | 0 | | |
| 39 | Red | 17 | 335 | Car | + | | ✓ | | | 0 | | |
| 40 | Water | 12 | 232 | Thirsty | + | | | | | 0 | | |
| 41 | Hurt | 15 | 302 | Inside | + | | | | | 0 | | |
| 42 | Flower | 29 | 589 | Arrangement | + | | ✓ | | ✓ | GS | | |
| 43 | Evil | 19 | 385 | Satan | + | | ✓ | | | GS | | |
| 44 | Party | 14 | 276 | Often | + | Often | | | | ST | | |
| 45 | Fly | 14 | 276 | Home | + | | | | | 0 | | |
| 46 | Death | 37 | 739 | Darkness | + | | ✓ | | ✓ | GS | | |
| 47 | Clean | 14 | 273 | Up | - | Now | | | | 0 | | |
| 48 | Try | 15 | 298 | Again | + | | | | | 0 | | |
| 49 | Sin | 18 | 360 | Devil | + | | ✓ | | | 0 | | |
| 50 | Home | 20 | 407 | Warm | - | Sweet | ✓ | | | 0 | | |

Median for words 1-50: 15.0

Responses Over PM: 20
Repeated SWs: 0
SWs with noise: 8
SWs with failed repro: 8
Rhymes or completions: 3
Multi-word responses: 1
Mis-heard SW: 0
Responses with gestures: 14
Perseverations: 0
No response in 30s: 0
Stereotypes: Around (5);Many(4) Often (5)
Mediate responses: 0
Meaningless responses: 0
Defensive reactions: 0
Slip of the tongue: 0
Foreign language: 0
Stutter/mispronunciation: 0

Factual Responses: 25
Egocentric Responses: 25

*FIG. 18*

SOUND ASSOCIATION TEST

CROSS-REFERENCE TO RELATED APPLICATION

The present Application claims the benefit of U.S. Provisional Application No. 62/180,225 entitled "Sound Association Test," filed Jun. 16, 2015, the disclosure of which is hereby incorporated by reference in its entirety.

FIELD OF THE DISCLOSURE

The present disclosure generally relates to projective tests, and more particularly to sound association tests.

BACKGROUND

Man's inclination to project or impose his own internal ideas on unstructured external stimuli has been noted and recorded for centuries. For example, Leonardo da Vinci states, in his Introduction to the Painter, referring to possible associative experiences from viewing a blot made with a sponge on the wall stated, that "various experiences can be seen in such a blot, provided one wants to find them in it—human heads, various animals, battles, cliffs, seas, clouds or forests and other things . . . " (Zubin, et al., 1965, p. 167). Also mentioned by Leonardo is the possibility of "hearing" words when a bell is ringing, indicating therefore that, "stimuli is not restricted to one sensory modality in their potential to evoke associative experiences" (Rabin, 1968, p. 3).

Association tests have their origin in the work of Sir Francis Galton (1822-1911) who used a word-association test as early as 1884, focusing his attention on the nature of the response words, and their relationship to the stimulus words. Galton's work was continued in Germany by Wundt (1832-1920), Ebbinghaus (1850-1909) and Kraepelin (1856-1926). Wundt was interested in the way in which individual words are connected with each other and how long the associations would last. Ebbinghaus used a system of "unrelated syllables" in the experimental study of memory. Kraepelin used the word association test as a clinical diagnostic tool and demonstrated that often-used associations needed shorter reaction times than the unusual ones (Kast, 1980). Jung (1875-1961) was to continue the development of previous word association tests while working under Bleuer. Jung was mainly interested in the diagnostic aspect of the word association; a projective method to uncover unconscious constellations (Kast, 1980).

Throughout the twentieth century, measurements of personality continued to play an important part in the clinical and experimental psychology of that time. During this time, the innovative and most prevalent projective methods, involved a shift from word-based association to the use of visual stimuli (Rabin, 1968). One of the most commonly recognized projective tests today continues to be the Rorschach test consisting of a series of ten symmetrical inkblot cards. The cards are presented to the subject individually and the subject is asked what the inkblot reminds him of or what they might represent. Additional projective tests such as the Thematic Apperception Test (TAT) that provided subjects with pictures that are intended to illicit internal information also enjoyed a degree of success and acceptance in the psychological community of the time.

It would seem natural then, given the success of projective tests such as the Rorschach and the Thematic Apperception Test (TAT), that the predominant use of one sensory or perception modality (visual) would eventually lead to the incentive or motivation to explore other sensory modalities, in this case the auditory. This motivation also included a practical consideration: that of attempting to create personality assessments for the blind and visually handicapped. Additionally one could consider that, "the frequent occurrence in everyday life of "mishearing" with self-reference and the marked preference of auditory hallucinations in psychotic patients speaks to the probable usefulness of an auditory approach" (Shakow, D., Rosenzweig, S., 1940).

Early in this century, Jung (1906, 1907, 1910, 1918) made the remarkable discovery that word association techniques, long fashionable among academic psychologists for the study of normal cognitive structure (Cattell, 1887; Galton, 1879), and already used by Kraepelin in psychiatric research (1892), could be used to identify what he called "complexes", unknown psychic factors lying outside of consciousness representing important areas of unconscious conflict (Lindzey, 1961, p. 33). In addition to the discovery of these "autonomous groups of associations", Jung's experiments revealed that the more unconscious a person becomes the greater the tendency to shift the mode of association from semantic to phonetic with the result that "reactions will be more and more influenced by sound, until finally only a sound will be associated" (Kugler, 2002).

Jung writes: "When a longish series of associations, say two hundred is given to a subject, he will, without really being tired, soon find the process boring, and then he will not pay so much attention as at the beginning. For this reason we have separated the first hundred form the second hundred in our classifications and have found that in all cases where the subject had become bored there is a clear decrease in the internal (semantic) associations. This observation made us think that the cause of sound association is not so much a muscular stimulation, which is absent in normal boredom, but a lack of attention . . . . Furthermore, we found an increase in the proportion of sounds associations with subjects whose ability to concentrate had been weakened by a recent affect, [and] with psychotics . . . it can therefore be said that the more the attention of the patient decreases, the more the external and sound associations increase (Jung, Psychopathological Significance of the Experiment, pp. 414-15). While this state of so-called "lack of attention" is worthy of note, the tendency to sonic and auditory association to be equally interesting.

The contemporary and principal use of visual stimuli in projective testing has limited the exploration of additional physiological sources of stimuli. Although the statement of words during the word association test may in a sense be said to be a auditory stimulus (we hear the word), words carry cognitive and culturally defined connotations relative to the spoken language that may or may not be evident in sounds. Jung reflects on the nature of speech stating, "Speech is originally a system of emotional and imitative sounds—sounds which express terror, fear, anger, love; and sounds which imitate the noises of the elements, the rushing and gurgling of water, rolling thunder, the tumults of winds, the tones of the animal world, and so on; and finally, those which represent a combination of the sounds of perception and of affective reaction" (Jung, C. G. 2002 p. 15).

While first half of the twentieth century saw an interest in attempts to create an auditory projective test (Lindzey, 1963), auditory stimuli did not experience the popularity and broader use attributed to visual projective tests. One contributing factor to its lack of use was the often bulky and cumbersome audio equipment needed to perform the tests. In contrast to previous difficulties, the design of the sound association test will address these deficiencies by making use of current advances in computer hardware/software technology, quality digital audio/video recording as well as the accessibility and portability of such equipment.

Projective tests have their beginning in psychoanalytic psychology, which argues that "humans have conscious and unconscious attitudes and motivations that are beyond or hidden from conscious awareness" (Singer, 1968, p. 582). Since almost anything a person may say or do could be said to reveal his/her unique style and be subject to interpretation as projection, it may be of value to explore some common characteristics evident in projective tests. By examining a variety of descriptions or definitions of projective test we should be able to ascertain several common characteristics relevant to these tests in general. The traits of projective tests derived from these definitions will serve as guidelines that inform the design and construction of the sound association test founded within the theory of projective testing.

Projective tests could be classified along many dimensions, however, a logical classification would seem to be one that is based upon the type of responses elicited; since such a classification would most likely be related to the underlying psychological processes involved in the test and what the subject is actually doing (Lindzey, 1961). Within this classification one could establish five general types of responses, that is, construction (story), completion (sentence), choice or ordering, expression, and association (Lindzey, 1961). According to Campos (1968), "The projective hypothesis has been extended to materials which encompass a wide range of stimuli not covered elsewhere: diverse objects, lines, forms, designs, patterns, expressions, words, pictures, cartoons, films, shadows, reflections, ideas, movements, toys, blocks, animals, paint, clay, drama, sounds, colors, clouds, symbols, dreams, memories, and pain" (Campos, 1968, p. 461).

Frank (1948) provides a short yet concise definition stating, "the essential feature of a projective test is that it evokes from the subject what is in various ways expressive of his/her private world and personality process" (Rabin, 1968, p. 11). After conducting an analysis of several definitions of projective tests and the criteria they are based on, Lindzey (1961) proposes that, "a projective technique is an instrument that is considered especially sensitive to covert or unconscious aspects of behavior, it permits or encourages a wide variety of subject responses, is highly multidimensional, and it evokes unusually rich and profuse response data with a minimum of subject awareness concerning the purpose of the test." He further adds that, "the stimulus material presented by the projective test is ambiguous, interpreters of the test depend upon holistic analysis, the test evokes fantasy responses, and there are no correct or incorrect responses to the test" (Lindzey, 1961 p. 45).

Rabin (1968) more concisely identifies three main attributes. First, that the stimulus is characterized by its "ambiguity", or more appropriately, by the "freedom" it allows the respondent to have in response to the stimulus (Rabin, 1968). Secondly, the responses involves a "variety and richness" [of content] with little awareness of the purpose of the material or the implication that may be drawn from it. Thirdly, the task of the examiner involves a multidimensional analytical approach and broad interpretation.

From these short definitions several characteristics related to the nature and technique of projective tests may be ascertained. The distinguishing features include: ambiguous or a lack of structured stimuli, a wide latitude for response alternatives, lack of awareness of the subject as to purpose of the test, a holistic view of the individual's personality, and the possibility of measurement for an unlimited number of variables and their interrelationship. (Lindzey, 1961, p. 41). In contrast to "objective tests" in which responses are analyzed according to a universal standard, projective tests are "content" analyzed for meaning rather than being based upon presuppositions about meaning (Neiu.edu, 2012).

In the beginning of the twentieth century several attempts were made to develop an auditory projective test. Primary amongst these was the Verbal Summator originally conceived by Skinner (1936), which he often referred to as "a devise for snaring out complexes", similar in concept to an auditory counterpart to the Rorschard inkblots. Skinner's interest in the projective potential of this technique was short-lived choosing instead to use his device to generate experimental data for his theory of verbal behavior. The Verbal Summator consisted of a series of recorded disks containing a combination of vowel sounds, a phonograph, and a specific tool that automatically reset the pick up (needle) so that patterns of vowels on the recorded disks could be repeated at will. Subjects were informed that the sounds replicated the speech of a man and that they were to identify what was being said even though this might be difficult. Some samples of single patterns are: u ' ' e (ooh, uh, ee), 'ah i (uh, ah, i), a o ' (a, oh, uh), di -dah -di -di dah and so on. (Skinner, B. F., 1936). Skinner (1963) published his article "The Verbal Summator and a Method for the Study of Latent Speech" (Skinner, 1936). While Skinner acknowledged the projective potential of his design, his article focused primarily on testing fundamental assumptions about verbal behaviors.

Other clinicians consequently adapted Skinner's devise for its research potential and applied purposes (Rutherford, 2002). Rosenzweig and Shakow (1938, 1940), for example, created variation on this technique to test for projective potential renaming their approach "The Tautophone", from the Greek prefix tauto, meaning to "repeat the same" (Rosenzweig, 1942, p. 48). Under this design, the subjects (schizophrenic and control groups) were instructed to provide responses to barely audible "vowel sound patterns" (ambiguous stimuli), while the experimenter recorded all responses, noting the number of repetitions necessary to elicit a response from each stimulus sample (Shakow & Rosenzweig, 1940). Subjects were instructed that they would hear some "rather unclear" voices, which they would have to listen closely and then report what they heard as soon as they had any idea. Dwight Chapman (1936), from the Psychopathic Clinic of the Recorder's Court in Detroit, on the other hand, requested the auditory devise feeling that the technique would be useful in criminological cases. He considered auditory technique to have the potential as an approach that could overcome criminal defensiveness as the test could be passed off as a "hearing test".

The auditory technique exhibited additional popularity evident by numerous requests for the devise by various Universities (Rutherford, 2003). Archival sources (Rutherford, 2003) indicate that additional requests for the Skinner's method came from, among others, Hadley Cantril at Princeton University (Cantril, Nov. 30, 1938), Wendell Johnson and William Grings at University of Iowa (Grings, Dec. 8, 1940; Johnson, Sep. 28, 1938) and Joseph Zubin at the New York State Psychiatric Institute and Hospital (Zubin, Oct. 14, 1938). In his correspondence with Skinner, Zubin (1939) stated, "all in all I feel that your approach has much promise both as a technique in its own field (verbal behavior) as well as a means for throwing light on the less objective aspects of the Rorschard experiment" (Zubin, Nov. 20, 1939). These and many other requests for Skinner's auditory test demonstrate the widespread interest in the auditory method and its potential as a projective test.

Williams Grings (1942) incorporated the auditory technique in the Iowa Psychopathic Hospital. He administered the test to variety of patient groups including those suffering from schizophrenia, psychoneurosis, and manic depression stating that, "As a test for the study of personality characteristics, the devise seems to have certain advantages, notably the capability of eliciting responses from patients when other techniques had failed" (Grings, 1940, p. 543). Additional requests for the auditory method continued throughout the 1940's with changes to the approach and application being incorporated. One such variation, for example, was the development and use of the auditory method by the American Foundation for the Blind (Braverman & Chevign y, 1952). Such variations and other applications of the auditory method speak to its potential as a complimentary and supportive technique to other projective techniques such as the word association test.

While many of the auditory tests were derivatives of previous models, Stone (1950) develop and new technique he called the Auditory Apperception Test (AAT). His technique marked a difference in auditory testing in that he replaced ambiguous sonic (verbal) stimuli with combinations of discernible sounds. His stimuli included for example, simple dialogue, crowd sounds, animal sounds, and sounds from nature (Rutherford, 2003). Subjects were given the following instructions, "This is a test of imagination, one form of intelligence. In a moment you will hear three sounds. When you have heard all the sounds, write or tell a story explaining what caused the sounds, what is happening and the outcome" (Stone, 1950, p. 351).

Bell and Bernardoni (1953) created a variation of Stone's AAT for use at the U.S. Disciplinary Barracks in Lampoc, Calif. This version contained two sets of stimuli including an instrumental recording to which subjects were to create a dramatic story describing what was happening, what had happened and what the outcome would be (Bell & Bernardoni, 1953). The remaining set of stimuli included a series of sound effects which subjects were asked to put together (construct) as parts of a dramatic story. In conclusion, the examiners stated, "Results indicate that the auditory projective technique utilized has been of practical value in a clinical situation and appears to offer good possibilities for further research" (Bell & Bernardoni, 1953, p. 58).

One final development included the work of Davids and Murray from the Harvard Psychological Clinic (1955). They adapted Skinner's original technique alongside those of subsequent developers renaming their version the Azzageddi test. Their approach presented subjects with spoken paragraphs designed to represent eight major dispositions or traits: optimism, trust, sociocenticity, pessimism, distrust, anxiety, resentment, and egocentricity (Rutherford, 2003). Subjects were requested to listen to the paragraphs and then recollect all ideas or thoughts that they could remember, indicating a major idea and two minor ideas as well as providing a report on the speaker's mood (Rutherford, 2003; Davids & Murray, 1955). The examiners concluded that the test had potential, in that "results accorded with clinical impressions of experienced psychologist and with sentence completion and word association results from subjects" (Rutherford, 2003).

The literature review presented demonstrates the historical interest in and the potential benefits of an auditory approach to projective testing both as a method in and of itself as well as a complimentary method to other projective techniques. The varieties of auditory stimuli presented (identifiable, unidentifiable) as well as the applications of auditory techniques (story creation, sound completion) will help to inform the design of the sound association test.

Jung made a distinction between two aspects of the unconscious, which he termed the "personal" unconscious and the "collective" unconscious. The personal unconscious contains an accumulation of experiences from a person's lifetime that is not consciously recalled; lost memories, painful ideas that are repressed, ideas or memories not strong enough, or not yet ready to reach consciousness. The collective unconscious, on the other hand, was the layer of the human psyche containing inherited elements. "The collective unconscious contains the whole spiritual heritage of mankind's evolution, born anew in the brain structure of every individual" ("The Structure of the Psyche", CW 8, par 342.). While the personal unconscious is the realm of the complexes, the complexes are normally centered about an archetype or and anthropological constant belonging to the collective unconscious. Thus by "complex" we are referring to contents of the personal unconscious that are connected emotionally around a nucleus of meaning (archetype).

We experience complexes in our everyday life. For example, when we experience a certain situation, an encounter, a conflict, a smell and even a sound (italics mine) that we connect with a particular circumstance, and this experience arouses in us the memory of a very significant event in our life, of a "situation that was connected with strong emotions, or many small hurts that refer back to the same problem . . . then we can say that a complex is evident" (Kast, 1980). This is particularly evident when the emotion that wells up inside us is disproportionate to the present situation. When we are in the midst of a complex, we not only experience intense emotions, we often react with unexplainable defense mechanisms or behavior patterns which are not in alignment with the current situation. We are regularly overwhelmed by our reactions; we react in way we are not aware of, we act as if under the influence of some autonomous power (Kast, 1980).

Jung spoke of an autonomous feeling-toned complex, when he said, "What then, scientifically speaking, is a 'feeling-toned complex'? It is the image of a certain psychic situation, which is strongly accentuated emotionally and is, moreover, incompatible with the habitual attitude of consciousness. This image has a powerful inner coherence, it has its own wholeness and, in addition, a relatively high degree of autonomy, so that it is subject to the control of the conscious mind to only a limited extent, and therefore behaves like an animated foreign body in the sphere of consciousness" (Jung, [1960] 1969:par. 201).

Complexes can thus represent a set of "feeling toned ideas"; that is ideas or associative connections that accumulate over the years around certain nucleus of meaning or archetypes, such as, "father" or "mother". Complexes are also evidenced by a strong emotional characteristic. When a complex is constellated it is habitually accompanied by an affected emotional state that is comparatively autonomous. Jung additionally states that, "Complexes interfere with the intentions of the will and disturb the conscious performance; they produce disturbances of memory and blockages in the flow of associations; they appear and disappear according to their own laws; they can temporarily obsess consciousness, or influence speech and action in an unconscious way. In a word, complexes behave like independent beings ("A Review of the Complex Theory," CW 8, par. 253.). Therefore complexes are held to operate autonomously, are characterized by an emotional affect and often have the effect of interfering with the intensions of one's will and conscious performance precisely because we are relatively unconscious of them.

A complex is not negative in and of itself but the effects of the complex often can be. Complexes may have a positive as well as a negative impact on the personality of an individual. For example, one may have a positive mother complex characterized by nurturing feelings and behaviors of kindness and compassion; or have a negative mother complex characterized by a devouring, destructive nature and a rigid obsession with perfectionism. A positive complex may provide inspiration and positive direction to one's life while a negative complex may make it difficult for an individual to express his/her genuine intentions or goals.

"The possession of complexes does not in itself signify neurosis . . . and the fact that they are painful is no proof of pathological disturbance. Suffering is not an illness; it is the normal counterpole to happiness. A complex becomes pathological only when we think we have not got it ("Psychotherapy and a Philosophy of Life," CW 16, par. 179). Jung additionally states that, "complexes are focal or nodal point of psychic life which we would not wish to do without; indeed, they should not be missing, for other wise psychic activity would come to a fatal stand still" ("A Psychological Theory of Types," CW 6, par. 925). What often results from a negatively affected complex is that in place of sound judgment and appropriate emotional responses, one simply reacts according to what the complex decrees. It is a matter of consciousness, that is, as long as one remains unconscious of the complexes they are likely to be governed by them. It is often more the case that the complex has us than we have the complex.

Each complex begins with its own individual experience usually occurring in our childhood or youth. Its origin is to be found in the initial trauma and consequent emotionally charged situation. When a person reacts negatively to a certain challenge or change in life a complex can be initiated. A person who suffers from the complex then finds it difficult to judge and act rationally in similar situations since these situations are affected and influenced by the initial experience. When we develop symptoms characterized by ineffective old patterns, thoughts and behaviors that are influenced by these complexes, we tend to fail to develop the true potential within our personality.

One of the goals of Jungian analysis is the process of psychological differentiation or the development of the individual personality, a process known as individuation. Jung (Psychological types [1921] 1971 par. 757) states, "The concept of individuation plays an important role in our psychology. In general, it is the process by which individual beings are formed and differentiated; in particular, it is the development of the psychological individual as being distinct from the general, collective psychology. Individuation, therefore, is a process of differentiation having for its goal the development of the individual personality". Jung goes on to state, "Individuation is practically the same as the development of consciousness out of the original state of identity. It is thus an extension of the sphere of consciousness, an enriching of conscious psychological life (Ibid par. 762). Jung states, "The task consists of integrating unconscious, in bringing together "conscious" and "unconscious". I have called this the individuation process . . . " (Jung, CW5, p. 301 par. 459). The aim is more to build a dynamic relationship (Auseinandersetzung) between the conscious and unconscious parts of the mind so that psychic development can be an ongoing process. Finally Jung states, "Individuation means becoming a single, homogenous being, and in so far as "individuality" embraces our innermost, last, and incomparable uniqueness, it also implies becoming one's own self. We could therefore translate individuation as 'coming to selfhood' or 'self-realization'." (Two Essays on Analytical Psychology, CW7, par. 266)

In order to realize this goal one must become aware of the unconscious processes that may be hindering ones development. The goal of analysis is to bring the subject into a state of awareness of all that was previously unconscious. Analysis examines our thoughts, actions and motivations that lie beneath our conscious awareness in the hopes of achieving a long lasting and positive change in the development of our personality. Through this process we come closer to the realization our true potential to the realization of our meaning and purpose in life.

To aid in the goal of analysis it is useful to have some knowledge of the nature of the complexes that may be hindering an individual in his personal development. Jung's study of complexes where closely related to the association tests. Jung's work in this field was founded upon word association techniques that had been used by psychologist such as Cattell (1887) and Galton (1879) in the study of normal cognitive structures, as well as in psychiatric research by Kraepelin (1892). As indicated earlier, Jung (1906, 1907, 1910, 1918) made the notable discovery that previous work in word association techniques could be used to identify what he termed "complexes", or "unknown psychic forces lying outside of consciousness representing important areas of unconscious conflict (Lindzey, 1961, p. 33).

During the years 1900 to 1909, Jung worked at the Burgholzli Hospital, the Psychiatric Clinic of the University of Zurich (Jaffe, A. 1989). His use of the association test was part of the "pioneering research going on at the Burgholzli in Zurich under the aegis of Eugen Bleuler (Jung, 1973). Ellenberger (1970) reports that, "Jung was experimenting, at this time, with formulating one of the first psychological tests that would be administered as a word association test". The test consisted of articulating a succession of carefully chosen words to a subject; to each of them the subject had to respond with the first word that occurred to him; the reaction time was exactly measured (Ellenberger, 1980). Specific reactions or "perplexing behaviors of association" were noted, "So instead of brushing these to one side and considering them as aberrant features or as "failures to react", he applied the interpretive method and formulated the theory of complexes". (Jung, C. G. 1973, Ellenberger, 1970)".

In what way does the word association test help to identify complexes? Jung postulated that, "Our conscious intentions and actions are often frustrated by unconscious processes whose very existence is a continual surprise to us. We make slips of the tongue and slips in writing and unconsciously do things that betray our most closely guarded secrets—which are sometimes unknown even to ourselves . . . . These phenomena can . . . be demonstrated experimentally by the association tests, which are very useful for finding out things that people cannot or will not speak about" ("The Structure of the Psyche," CW 8, par. 296).

The Word Association Test consists of a list of one hundred words to which the subject is asked to respond as quickly as possible to with an association. The examiner conducting the test measures the delay in response between the stimulus word and the subject's response. An average response time is calculated to the first set of associations. Responses over this average mean are considered to be a complex indicator. The words are read a second time to the subject without the need for timing, again noting any differences in responses be they a lack of response, incorrect reproduction or other types of physical motions. The final step involves the subject commenting on the responses to words for which there was a longer than average response time. The subject would also comment to situations in which there was a different response, no response altogether or for which there was an unusual number of physical signs.

The primary types of criteria that indicate complexes include responses that are over the mean average response time, no response or a different response reproduction to stimuli word. Additional complex indicators include response to a misunderstood word, gestures, movement, laughter, noises, stuttering, mispronunciation, rhymes, disconnected reactions, multiple word responses, colloquialism, foreign language response, and stereotypes. These subtle differences in responses, lack of recall, slips of tongue, gestures, all indicative of unconscious processes are considered to be "complex indicators" and were as Jung stated above, "helpful for finding out things people cannot or will not talk about", things that "betray our most closely guarded secrets" ("The Structure of the Psyche," Ibid, par. 296).

Other ways in which the association test may be helpful in the analytical process include establishing a standing diagnosis during the initial stages of analysis. Its use can be helpful in establishing a preliminary view of presenting issues; issues of which the subject may not even be aware. The successive administration of the test may help to inform any changes that may or may not be occurring during the course of analysis. The association test can also be beneficial in those situations where the subject presents with little or no unconscious material. In theses cases, the administration of the test often has the effect of stimulating dreams (Kast, 1980).

Historically the auditory tests have tended to be dismissed in certain scientific circles by those who favor strict quantitative results citing low reliability and validity content, poor subjectivity of interpretation, and other factors; a problem ascribed to projective testing in general. Additional reviewers (Bean, 1959; Swensen, 1959; Lindzey, 1961) who listened to the AAT (auditory apperception test) recordings found many of the sounds poor in auditory quality with the result that the poor quality of the recordings may lead to gross, but justifiable, misperceptions. Early auditory efforts were plagued by poor sound quality as well as cumbersome equipment that often made its use impractical. Many of the auditory systems were never fully developed or published with adequate manuals or scoring systems and lacked large-scale standardization and validation studies. The initial interest and popularity of auditory projective testing was replaced by the growing movement based on cognitive behavioral sciences and emphasis on objective personality assessments (Baso & Berg, 1959).

In general, psychoanalytic methods have been criticized on many counts including the fact that they can be a lengthy and expensive process, that they involve extensive subjective content, and the belief that subjectivity versus objectivity creates difficulties in the measurement of effectiveness. The outcomes of analysis that are considered beneficial often involve elusive constructs such as "meaning in life", "self-realization", "balance", and amelioration of specific symptoms. Not all participants may be motivated to explore deep-rooted psychological issues.

SUMMARY

Embodiments of the present disclosure may provide an auditory projective test that emphasizes a shift in focus from visual and verbal/linguistic stimuli to an examination of the phenomena of acoustic and sonic association. The design discovers a "canon" of sound stimuli that may provide psychological associations with the aim to further inform and compliment the findings of Jung's word association test. The design includes a computer software program that gathers and calculates data in Excel format. Jung's traditional Word Association test is presented alongside the sound association test. The design may include the use of digital video recording to help observe and demonstrate behavioral responses. Additionally, the design may include the addition of a digital interface that will reintroduce the measurement of certain physiological data originally used in Jung's association experiments. The design represents continued research in the field of analytical psychology. This design examines the nature of association phenomena through the design of a new associative test that will provide sounds as the origin of the stimulus effect.

In an effort to explore the state of decreased attention (unconscious) in which "sound associations increase" (Jung) the design of a test using external nonverbal sounds. Sounds may present a more primitive, preverbal, or archetypical association not influenced by the socio-cultural superimposition of connotations evident in language. The design may allow for the administration of the test to be given using a laptop computer.

Not all stimuli sources need be ambiguous. In some cases subjects are requested to respond to identifiable stimulus such as words, recognizable images and/or specific sounds. The design for this sound association may include identifiable as well as ambiguous sounds. The combination of sound stimuli (ambiguous/identifiable) is meant to stimulate a variety of responses that can help to inform the creation of a canon of (psychologically relevant) sounds.

The associative techniques reflect those found in the word association test, namely that the subject is requested to respond to some stimulus (auditory in this case) presented by the examiner with the first word, image, or percept that occurs to him. A subject will have relatively no idea of the purpose of the test and will have wide latitude for response. Following the nature of projective experiments, the auditory test according to embodiments of the present disclosure aims to inform the examiner of underlying psychological processes evident in the subject based upon responses to auditory stimuli.

The rationale for the design of the auditory test according to embodiments of the present disclosure is based upon the projective hypothesis, which states "when a subject attempts to understand an ambiguous stimuli they tend to impose their own meaningful structure with the result that their personal interpretation reflects the unconscious needs, motives and conflicts of the subject" (Gregory, 1996, p. 51 as cited in Merrell, 2003, p. 184). By ambiguous, we are referring here to stimulation to any sensorial mode in such a way that that it could be construed in one or more ways than one, and that is it is open to interpretation. According to Murray (1973) the rationale behind projective techniques is that people tend to interpret ambiguous situations in reference to their own past experiences and current motivations, whether this be conscious or unconscious. He further reasoned that by asking subjects to relate an association, that defenses to the examiner would be diminished and thus allow sensitive information to be divulged. White (1944) additionally states that the "general idea behind the projective methods is to confront the subject with an unstructured, ambiguous stimulus and allow the subject a certain degree of freedom to organize responses or create meaning in his own way" (p. 215).

Not all projective stimulus needs to be ambiguous in nature. Identifiable stimulus also has the ability to allow for projection. The use of individually identifiable words or sounds could be said to be rather clear cut, definite and identifiable. These would be words one would know the meaning to or sounds one could identify. However when these words or sounds are presented out of context, they develop a sense of ambiguity, which may then serve to elicit unconscious associations. The placement of individual words in random order could be said to constitute an element of ambiguity. The design of this test has followed the work of previous sound association tests, primarily that of Stone (1960), in which both identifiable and ambiguous acoustic stimuli presented in an unstructured manner.

As seen from the literature review, Skinner (1936) originally conceived of his Verbal Summator test as "a device for snaring out complexes", a concept similar to an auditory counterpart of the Rorschard (Rutherford, 2002). Skinner's design was consequently adapted and modified by other clinicians for its research potential and applied purposes. The design of this sound association test according to embodiments of the present disclosure may reestablish the use of auditory stimuli in projective testing both for research purposes and applied techniques such as complimenting the findings of the word association test. In the same manner as the word association test is designed to elicit associations and discover complexes, so too the design of the sound association test according to embodiments of the present disclosure seeks to discern complexes through associations to auditory stimuli. The responses to (sonic) stimuli (ambiguous or identifiable) and the consequent content analysis of such responses may help to inform associative results (of word association test) by providing the analyst with a complimentary set of data gathered from an auxiliary physiological source. (Projective Methods for Personality Assessment. (n.d.). Retrieved Nov. 21, 2012, from http://www.neiu.edu/~mecondon/proj-lec.htm).

Associative experiments may have dismissed the importance of sound on the unconscious, focusing on the symbolism found in visual imagery without considering the potential symbolism that may be apparent in sound. The principal method of projective testing during the early twentieth century focused on visual stimuli (Rorschach, TAT). The dominant preference for the visual constantly strengthens the word image and its visual connotations by implying that "images" are seen rather than sensed. One could put forth the concept of a sound image but then again one would be using a visual construct ("image") to describe it.

The benefits of including an auditory approach consist in accessing an alternate physiological source other than the traditional use of visual stimuli. Visscher, Kaplan, & Sekuler, (2006) state that, "Since visual and auditory information arise from different sensory organs and are processed across different pathways, discrepancies in their associated memory processes would not be surprising, and have been claimed by various studies". Due to these differences in sensory processing, auditory stimuli may be able to recreate environmental conditions in ways that are difficult for visual stimuli to replicate and thus give rise to thematic material not elicited by other forms of stimulus.

We do not hear sounds in isolation; we hear sounds in connection to our environment, events and people, motion of objects, nature, always interdependent with the dynamics of the moment. Recalling a sound requires consideration of the event that produced it. Musicians and composers have long understood the ability of sound to produce and preserve emotion. Sounds are as integral a part of our daily and historical experience as is the visual world. Memories, experiences and their associated affects are the substance of complexes, and sounds, much like other forms of stimuli, additionally have the ability evoke "images" and recall experiences useful in eliciting associations.

A large portion for the lack of auditory testing in the past was related to technical issues, such as cumbersome equipment and difficulties related to audio fidelity. The advances in modern computers and digital audio technology have addressed many of these issues. The suggested design allows for the administration of the sound association test to be given from a standard laptop computer currently running Mac OS X 10.9.5 or higher. From this platform, digital (audio) samples can be created and reproduced with great fidelity. The use of computer software programs also allows for the gathering and processing of significant amounts of data. The portability of current computers makes the use of a sound association test accessible to large population of examiners. The flexibility and increased processing power of current laptop computers has aided this design by allowing the incorporation of a video component that permits the examiner to record video footage of subject's responses to both the word and sound stimuli. The design anticipates that the addition of video should prove beneficial in the identification of physical/mechanical complex indicators. Additionally, the computer platform has allowed for the integration of a digital interface that will reintroduce the use of biometric data that originally accompanied the word association test.

Additional benefits to an auditory test is that the test may be given without consideration for linguistic misinterpretation, that is sounds, would not need to be translated into different languages nor would there be potential for misunderstanding based on colloquial dialects. The use of auditory projective techniques could also prove to be helpful with populations that are visually impaired and or blind.

BRIEF DESCRIPTION OF THE DRAWINGS

For a more complete understanding of this disclosure, reference is now made to the following description, taken in conjunction with the accompanying drawings, in which:

FIG. 5 depicts a spreadsheet in a main application window for use in a sound association test according to an embodiment of the present disclosure;

FIG. 7 depicts a sample of calculated results of a sound association test according to an embodiment of the present disclosure;

FIG. 17 depicts a sound protocol according to an embodiment of the present disclosure; and FIG. 18 depicts a word protocol according to an embodiment of the present disclosure.

DETAILED DESCRIPTION

Figure 1:
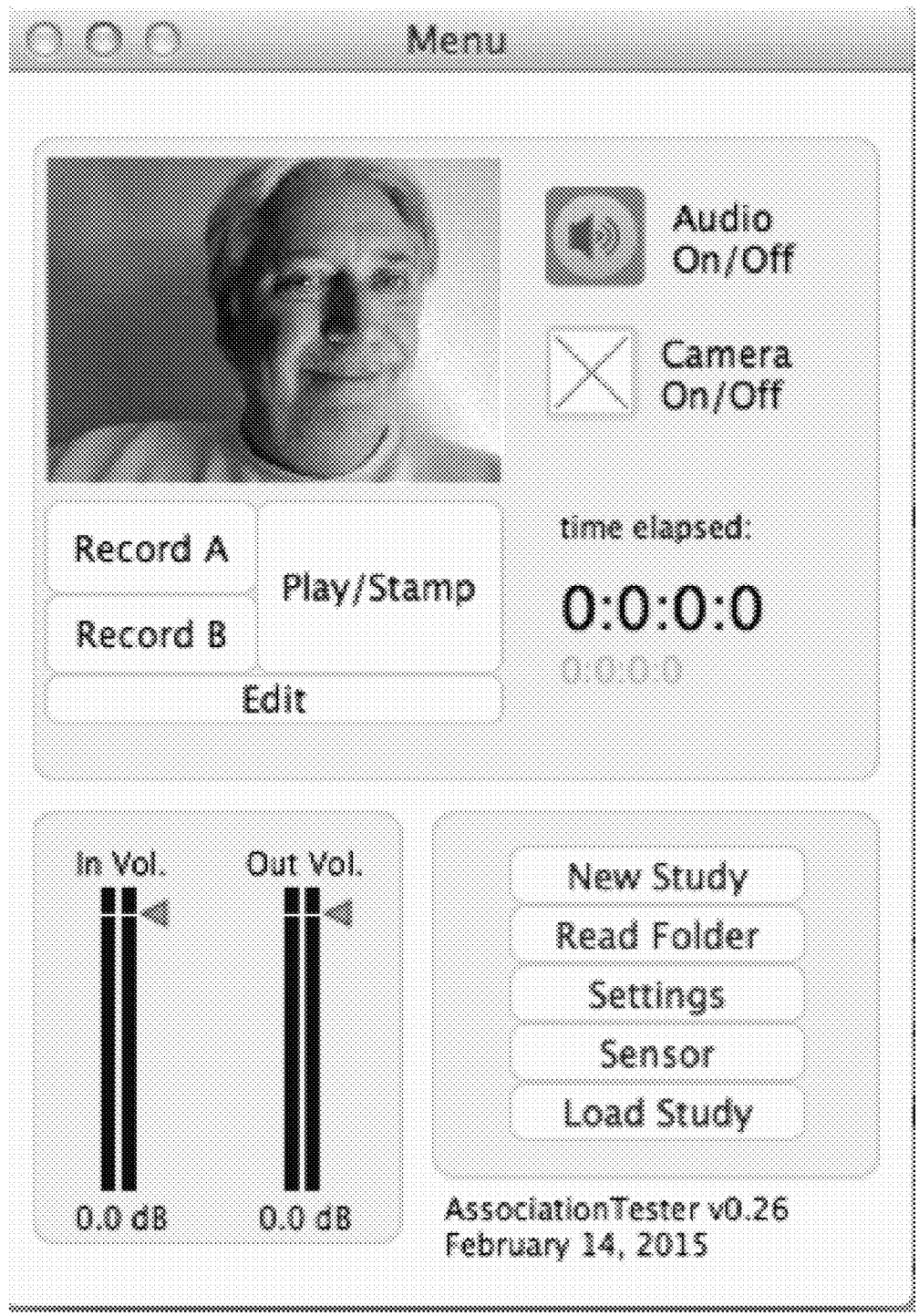
FIG. 1 depicts a main menu design for use in a sound association test according to an embodiment of the present disclosure.
Figure 2:
FIG. 2 depicts settings for use in a sound association test according to an embodiment of the present disclosure.

The use of sounds (ambiguous and identifiable) and their ability to elicit associations has been evidenced to various degrees by the examples of sound associations tests referenced in the literature review. The sound association test according to embodiments of the present disclosure is based upon the principles of the projective hypothesis (association to stimulus) and the use of previous (sound) association methods whose goal it was to elicit unconscious information. The design will introduce the use of audio and visual elements as well as physiological measurements.

The design according to embodiments of the present disclosure may inform and compliment the results derived form the Word Association Test through the introduction of "sonic" stimuli. The introduction of "sonic" stimuli may elicit associations that reveal unconscious material in a similar manner, as does the word association. The sound association test according to embodiments of the present disclosure may broaden the findings of the Word Association Test by providing additional information in the realm of complex indicators. To this end, both the Sound and Word Association Test may be presented within the same application providing a compare and contrast scenario.

The design may utilize ambiguous as well as identifiable "sound" stimuli with the intent of eliciting associative responses. The design follows the criteria present in the word association test that classify certain reactions as complex indicators. These include response time above average mean, no response to stimulus, different reproduction, repetition, identification of sound versus association, multiple word response, gestures, movement, laughter, stuttering, noises, rhymes, disconnected reactions, misunderstood sound, mediated response, and response in foreign language.

The sound association test according to embodiments of the present disclosure does not seek to stipulate conclusive results as to the associative qualities between words and sounds but rather seeks to create an experimental platform that will allow the examination of the phenomena of sonic association. Subsequent use of the sound association test according to embodiments of the present disclosure may lead to the establishment of "standard set" or "canon" of sounds to be used based upon their ability to elicit unconscious associations in a manner similar to the word association.

To address the difficulties found in earlier versions of auditory association testing (cumbersome equipment and poor audio quality) a computer program has been created that contains and plays digital samples, records the auditory and visual (physical) responses of the subject, has the ability to record certain physiological data, and provides calculations of gathered data. The computer program may run on a single laptop computer and contain within it all the necessary software and hardware features to implement the test. The current design combines two distinct computer programs: MAX, an object oriented music programing software developed by IRCAM ((Institut de Recherche et Coordination Acoustique/Musique) and Excel 2011 by Microsoft. Currently the program is designed to work with Apple Mac computer running OS X 10.9.5 or higher. Additional hardware components that can be added and used include different formats of video recorders, microphones, headphones, and a digital interface for physiological data (GSR, Pulse, Oxygen, etc.). However, other hardware and software components may be utilized without departing from the present disclosure.

The sound association test according to embodiments of the present disclosure is designed after the Jung's Word Association experiment. The application contains dual component within a single application. The sound association test according to embodiments of the present disclosure may contain the fifty (50) word association test along with a fifty (50) sound stimulus test. The words are the standard words found in the fifty (50) Word Association Test. The fifty (50) sounds are classified by categories identified by the following initials: sounds of nature (NA), human sounds (HU), animal sounds (AN), urban sounds (UR), and ambiguous stimuli (AMB) (see section on Sound Categories bellow). The sound association test according to embodiments of the present disclosure was designed with both the word and the sound association portion of the test within the same application to provide a "compare and contrast" environment between the use of word and sounds in projective testing. [Note: A second version of the test containing the one hundred (100) word association test and one hundred (100) sound stimuli is also available]. It also should be appreciated that more or fewer words and sound stimuli may be utilized without departing from the present disclosure.

The sound association test according to embodiments of the present disclosure introduces the use of audio and visual recording. The design allows for the visual and audio recording of reactions to both words and sounds, as well as the recording or the reproductions. This element was incorporated into the design in an effort help log responses and identify complex indicators. The video and audio responses of the test can be replayed and further analyzed by the examiner after the test has been completed. This may allow for a higher degree for the recognition of "complex indicators" as these can often be difficult to recognize and notate during the examination process. This design function can be used for educational purposes in demonstrating what constitutes a complex (gestural responses, noise, motion, etc.).

One consideration that has become evident from the inclusion of the video design element is the need for increased client confidentiality. While findings of the tests can normally be disguised by withholding the subject's identity or by referring to the subject in an unspecified way, this is not necessarily possible with the video component.

Subjects often requested that the video component of their test not be disclosed in the process of discussing test results.

The sound association test according to embodiments of the present disclosure incorporates a new timing element, which allows the computer keyboard "spacebar" to act as the stopwatch mechanism usually used in the association experiment. Once a stimulus word is active (indicated in "red") the pressing of the spacebar on the computer keyboard activates the presentation of the stimulus and begins timing. Pressing the spacebar again upon hearing the reaction word stops and completes the recording process. The timing may be automatically recorded and presented in the timing column. This process frees the administrator of a significantly difficult activity of notating and calculating the timing of 5th and 100s of seconds.

In addition, an interface has been incorporated that will allow for the monitoring and recording of supplementary physiological data. Presently the biometric data will include heart rate, oxygen level, and galvanic skin response. The interface has the potential to incorporate various other physiological data. The results of the biometric reading may be displayed in graph form as well. The graphic information will be found at the bottom of the excel sheet by clicking on the desired name. The fields available are AEprot, Response Graph, Reaction Time Frequencies, CI Ranking, and various Biometric graphs such as GSR (galvanic skin response), Oxy (oxygen), Pulse. However, other fields may be provided without departing from the present disclosure.

The design (Version 27) has been informed by changes in the developmental construction of the test. While not all versions are discussed, the previous versions were generally helpful in informing changes that became necessary as a result of the implementation of the test during the preliminary design phase. The primary changes included issues with compatibility between programs, translation of information between program applications, the introduction and presentation of digital audio and visual recordings within the application, the introduction of physiological measurements and formatting features for representation of the information.

Results from the administration of the sound association test included herein are not conclusive but rather, represent efforts to create the construction of a stable design. Preliminary findings, observations, and questions that have become apparent and have been essential in the design of the test will be discussed. While the current version of the test represents an operable and stable platform, it is important to recognize that the design is created to be flexible and allows for subsequent additions and or modifications to be made. This characteristic provides the test with the potential to adapt and transform along with findings that may become apparent from future results.

The word association component of the design uses the same words evident in the fifty (50)-word version of Jung's Word Association Test. On the "word" side of the test, digital samples have been used to replicate the stimulus words (in English). The examiner can use the digital voice samples of the stimulus words or chose a "Mute" function and articulate the words themselves. The voice samples were created to demonstrate an additional design function, which addresses the potential of recreating the word association test in different languages. For example, digital samples of the words in English can be created in both masculine and feminine voice and can be representative of different regions (England vs. America). The words could be digitally recorded in variety of languages form English, German, Spanish, French, and Italian, indeed any language in which the test may conceivable be given. However, one would have to consider whether the same words that exist in the current English or German version of the word association test would be suitable stimulus words in other languages and cultures as they may have significantly different meanings and cultural connotations. It is not the intent of this design to ascertain what words may be of psychological interest in different languages. The design of the test, however, allows the flexibility for any examiner to introduce digitally sampled words to suit the design of their own experimental decisions in their own native language.

"Sound", as discussed according to embodiments of the present disclosure, may refer to the heard vibration of any object that has been struck or set into vibratory motion. Objects include tangible items as well as living things. The slamming of a door, a human voice, the sounds of nature, animals, all create sound through vibration. This is somewhat different from what is referred to in the word association test under the categorization of "sound reactions". The content of the "sound reactions" group (as indicated in the word association test) corresponds to Aschaffenburg's group of "stimulus-words acting only by sound." Jung, C. G. (2014 Mar. 1). Within this classification of "sound reaction" we have "word completion" (wonder-ful, love-ly), "sound" (enchain, enchant; humility, humidity), and "rhyme" (dream, cream; heart, smart). "Sounds" may include sounds of objects, human voices, sounds of nature, and environmental sounds and sounds heard in everyday life.

The nature, type and category of the sounds that stimulate associations are also an integral element of embodiments of the present disclosure. Identification of sounds may be an ongoing developmental process informed by the results of the sound association test according to embodiments of the present disclosure. It is further anticipated that psychological insights acquired throughout the choice of and initial testing of sounds may provide criterion for the development of a standard or norm of sounds that can be used by subsequent examiners.

To address this developmental issue, "folders" of different sounds can be created that allow for the examiner to change, add and/or replace individual sounds samples in a "master" folder which is then used for experimentation. The digital samples (.wav format) contained within files serve as the stimulus sounds to be used in this research. The sound stimulus for this test may include 50 sounds in five categories. The sounds have been placed within the test in random order.

The selection of sounds and their categorization is informed by previous work done in sound association as mentioned in the literature review. This includes the use of ambiguous sonic/vocal segments as well as identifiable environmental sounds. The choice of sound groups for this design is based primarily upon categorization of sounds used by Stone (1950) in the Auditory Apperception Test (AAT). While many of the auditory tests were derivatives of previous models, Stone's (1950) technique marked a difference in auditory testing in that he replaced ambiguous sonic (verbal) stimuli with combinations of discernible sounds. His stimuli included for example, simple dialogue, crowd sounds, animal sounds, and sounds from nature (Rutherford, 2003). Based upon previous classifications the following categories listed below have been developed for inclusion in the sound association test according to embodiments of the present disclosure; however, other categories may be used without departing from the present disclosure.

Additionally, many of the words in the word association test that have the potential of being represented as a sound have been included. For example, the word "Water" can be represented by the sound of running water. Words that are found in either the one hundred or the fifty-word association test and have the potential to be represented as a sound have been included as such in the sound association portion of the test. These are shown in bold and include: #3. Water, #4. Sing, #18. Sick, #20. Cook, #22. Angry, #40. Pray, #47. Bird, #51. Frog, #55. Child, #63. Glass, #64. #77. Cow, #88. Kiss, #89. Bride, #91. Door. These sonic representations of the words may be of special interest and will allow for a compare and contrast observation of reactions between words and sounds.

Sound Categories:

AMBVALENT: Electronically generated sounds—identified by number. 001, 007, 012, 017, 027, 032, 043, 048.

HUMAN: Sound related to human beings, behaviors, activities, bodily functions, etc. Sick, sing, walk, sex, applause, kiss, scream, laugh, breath, bride.

NATURE: Sounds indicative of nature and natural phenomena. River, rain, thunderstorm, wind, waves, water.

OBJECT: Sound made by human activities or by objects commonly found in the world. Phone, door, cooking, bells, ice, shots, teapot, ship, ANIMALS: Sound of animals, both domestic and wild. Bird, rooster, dog, cow, wolf, pig, owl, cat, crickets, frog.

URBAN SOUNDS: Sounds related city or town environment. Traffic, siren, siren, train, airport, jackhammer.

Certain sounds may be placed in an order that may be construed as a scene. For example: shot, scream, accident, and siren.

The final portion of the sound association test according to embodiments of the present disclosure may allow the reintroduction of physiological data originally present in Jung's Word Association Test. While this design does effectively introduce an interface that allows for theses measurements, this function was not introduced in the early tests of this population sample. This exclusion was due to ongoing improvements in the implementation of such devices as well as the rendering of such information into graphical form. Additional comments by subject indicated that use of these devices was awkward and made one feel as if in a "lie detector" test. It was also noted that the use of such devices tended to limit the ability for natural gestural responses. Questions of instrument calibration and appropriate baseline readings for the representation of graphical material are ongoing. The test, however, does present some sample graphical examples of the rendering of such information.

Subject Tests Instructions

The presentation of the subject instructions is an integral part of the design. Both the word and the sound association component have their own set of instructions. It is important that the subject understand the instructions.

Word Association Test:

Prior to beginning the testing one must introduce the instructions. For the word association test one explains to the test subject (TS) that he is undergoing an association test (not an intelligence test).

"I will read 50 (or 100) words, one after the other. To each of these words you are requested to answer, as quickly as possible, with the very first word, thing or image that occurs to you in connection to that word. Please answer with one word only, if possible. I will measure the time you will take to answer. It is important that you really say the first word or thought that comes to mind".

Sound Association Test:

The instruction is an integral part of the experimental design. This is particularly true for the sound association test. One has to make sure that these instructions are understood. If this is doubtful, one should make a "dry run" or provide an example of what is intended by using a "sample sound" prior to testing. For example, one could use the tapping of a glass or closing of a book. One could respond by saying "glass" or "book" which would be an example of identification. Or one could associate "water" to the glass sound or "study" to the book sound.

"I will play 50 (or 100) sounds, one after the other. Some you may recognize others you may not. To each of these sounds you are requested to answer, as quickly as possible, with the very first word, thought or image that occurs to you in connection to that sound. Avoid trying to describe the sound—simply reply by saying the first thing, be it a word, thought, or image that comes up in connection to that sound. Please answer with one response only, if at all possible. I will measure the time you will take to answer. It is important that you say the first word, thought, or image that comes to mind without "describing" the sound".

Recording

To begin recording, one must choose "New Study" from the menu. This activates the main "Spreadsheet" window (FIG. 5). Both the reactions and the reproduction for the words and sounds are recorded separately. In the menu window, the examiner chooses "Record A" function to record the reactions to stimulus words/sounds and "Record B" function for the reproductions. The difference between the two record functions is that the "Record A" function creates a time stamped response for the reactions whereas the "Record B" function is intended to record the reproductions without the need for a timed element.

Once the record function has been chosen, the examiner uses the mouse to highlight the stimulus word/sound (red indicating ready). The examiner then uses the space bar on the computer to play the stimulus sound. This process plays the stimulus word/sound and additionally records the subject's association (both verbally and visually) as well as records the response time. Depressing the space bar again stops the stimulus and finalizes the recording of the response for that individual stimulus. This design function replaces the use of a stopwatch as a timing mechanism. Once a stimulus word is active ("red") the pressing of the space bar plays the word/sound and pressing the spacebar again stops the stimulus and times the event.

The program records the (video and audio) response time for each stimulus sample and automatically creates the prime mean time value of responses. The reaction column is blank and allows for the examiner to input the response between the presentation of stimulus words or sounds. After stopping the recording by pressing the spacebar, one "double clicks" in the reaction window and inputs the reaction word given. This procedure is done for all 50 words/sounds. Pressing "Record A" while it is red stops the recording for the first trial.

The second recording function (record B) does not calculate response time and is used for the reproductions. The reproduction column allows for the entry of a "+" or "−" sign to identity a positive or negative reproduction. The "notes" column allows the examiner to input the false reproduction and other notes such as gestural or rhyme responses etc. One uses the same procedure as above, clicking on words/sounds to highlight them, then pressing spacebar to activate the stimulus word/sound and record the reproduction; pressing the spacebar again to stop recording and create a time stamp.

Export to Excel

After the recording of the reactions and reproductions, the examiner will use the "export to excel" function. The "Export to Excel" function is found on the top right hand corner of the main "spreadsheet" window. The information to export will include all the recorded timing of reactions, the noted reaction words, the recording of reproductions, the noting of positive or negative reproductions, and any other information noted in the "Notes" section. However, it should be appreciated that other exportation formats may be used without departing from the present disclosure.

The "Export to Excel" function begins the use of the Excel portion of the test. The "Export to Excel" window opens the final portion of the test presented again as an Excel spreadsheet. Next, one will be prompted by a message box to "Get and Process data to Excel". Pressing in this box translates the information gathered in the initial spreadsheet to the master final excel sheet.

The test results are translated into the master Excel program, which calculates the Prime Mean time, number of complex indicators and allows for graphs and tables to be generated. As indicated, the application is now operating within the excel program portion of the test. Once in the master Excel program, the examiner can continue to add complex indicators in the "complex indicator" field. To assist in the process of complex identification one can either refer to comments made in the "note" section or review the video responses for complex indicators. The complex indicators other than >PM, noise, repeat, factual or egocentric are to be noted in the "other" section. In order for these to indicate a complex one must follow a set identification code.

TABLE 1

'Other' CI codes
Table 2. Complex Indicator ID Code

| Code | Description | Example |
| --- | --- | --- |
| DR | Defensive reaction | Can be detailed in Reaction Notes |
| FL ("phrase") | Change to foreign language | |
| GS (gesture) | Non-verbal gesture | GS(frown) |
| MED ("response") | Mediate response | |
| MIS ("mis-heard SW") | Mis-heard SW | For SW "wool", subject hears "wall": MIS("wall") |
| MR | "Meaningless" or unclear relation to the SW | |
| MWR ("response") | Multi-word response | MWR("I can't make my mind up . . . dog") |
| NR | No response after 30 seconds | |
| PT | Perseveration Trigger | |
| RC | A rhyme or completion of the SW | |
| SL ("slip") | Slip of the tongue | Subject says "Dog in heaven": SL("Dog") |
| SM ("phrase") | Stutter or mispronunciation | |
| ST | Stereotype | |
| | Multiple codes example | PT; MWR("I'm thinking about . . . no"), ST |

As the examiner places information in the "complex indicator type" section, the program may evaluate the total number of complexes indicator for that stimulus word/sound and rank all stimulus in order of how many complex indicators are present for each sample. The program may automatically create graphs illustrating response time, reaction time, and CI ranking. Graphs may be displayed in the lower portion of the Excel sheet.

The entire administration of the test, includings the words and sound, reactions and reproductions, are recorded in audio as well as video format. The output of these recordings may be found in the file that was named by the examiner at the beginning of the exam. All recorded information for the word portion of the test may be found in a "Words" folder, while all the information pertinent to the sound test may be found in a "Sounds" folder within the main file. One can review the entire process of both auditory responses and visual cues to stimulus. Individual visual and auditory responses may be "tagged" to each word and sound for ease of recollection. An examiner may "jump" to any particular word or sound response within the test by accessing a pull down menu (video recording) containing the list of stimuli. If the physiological data interface is used, the information for the physiological data is automatically inserted in the columns for which the design is currently set to measure and biometric data is represented in excel graphs. The entire experimental process may be recorded and saved within the main file.

Physiological Measurements

Due to the fact that the inclusion of physiological data was an ongoing element during the design of the test, the presentation of these readings was not administered to all subjects within this sample population. The administration of physiological data testing began with the fifth subject and its continued development involved changes in the design of the graphical representation of the information. The changes represent consideration of appropriate "base line" readings and implementation of averages for the measurements that help facilitate the visual reading of this data. Therefore, being in a state of ongoing development, the reporting of physiological data is not included in the final results of this research but presented a part of the ongoing design of the test.

C. G. Jung, in "Diagnostic Studies in Word Association", first mentioned the use of the psychophysiological components in the Association test. Under Jung's direction, the connection between respiration rate and reaction time was also measured and evaluated. Other collaborators in the use of psychophysiological devices include Binswanger, Peterson, and Riklin senior. Other studies, such as Schlegel's dissertation on "Psychological and Psychophysiological Aspects of the Association Experiment" have further addressed and informed the use of biometric data in the Association test (Jung, 1973; Kast, 1908). The use of such information in the Association Test revealed that complexes are not simply psychic but that bodily phenomena are included as well. Therefore, body movements, gestures, mechanical motions that occur during the test may be considered as complex indicators. The body reacts to emotions just as well as does the psyche. The inclusion of bodily response then provides a more holistic indication of complexes.

One can envision that the inclusion of physiological data and its interpretation can be time consuming. Additional concerns include consideration that the cost of such equipment could also be restrictive for some examiners. Concerns of this nature often create limitations and restrictions for the use of such devices. The design of this test allows for the inclusion of such data via the creation of the realized interface at a relatively affordable cost with a minimal use of space. In an effort to re-establish some of the measures evident in the original Association Test, this design has incorporated the construction of an interface that allows for the inclusion of biometric data comprising of pulse rate, oxygen saturation levels and galvanic skin response (GSR). The biometric data is "tagged" to each reaction word/sound and an excel graph displays the entire biometric data throughout the test period. The program calculates the average of each type of biometric data and displays this information on individual graphs that allows the examiner to see words/sounds reactions that occur above or below said average.

The purpose for the inclusion of the current biometric data was twofold. First, it was to demonstrate that physiological data, once an integral part of the original word association experiment, can be and indeed has been successfully integrated into the current test design. Secondly, it was to demonstrate that space and financial considerations that were once a hindrance to the continued use of such data can be overcome. The current biometric adaptations are objects that can be easily transported and are within reasonable financial reach of most individuals willing to purchase such equipment. The test design and the interface used may be flexible enough to incorporate additional physiological data should future examiners consider this to be of interest.

However, other aspects come into consideration when subjects are connected with electrodes that are meant to read the physiological data. During the design process of this test it has been noted that the inclusion of these devises tend to limit or restrict the freedom of gestural response, particularly hand motions to the face, hair, or mouth, etc. The initial versions of the sound association design did not have a biometric component, and therefore the original subjects who engaged in the preliminary testing of the sound association test were not exposed to the biometric data component.

Once the biometric component was introduced, the execution of the test differed in a subtle way. Comments from test subjects in response to their experience of the physiological data indicate that there exists an occasional reluctance on their part to be connected with such devices as the subjects feel they are undergoing a "Lie Detector" test. If one intends to use biometric data as part of an association test with this design, then the nature of the biometric data, its use and purpose in the test must be clearly explained to the subject. The addition of these measurements is a part of the overall design of the test. The interface can additionally be adapted to read other biometric measurements not currently employed in this test.

The test can be conducted effectively without theses additional devices if necessary. The option to include physiological data or to exclude it from the exam remains the choice of each examiner. As stated before, one of the reasons for these additional factors to be excluded is that subjects may feel the process to be to invasive. However, if the nature of the physiological data and its use is clearly explained, the subject may then feel more willing to participate.

Figure 9:
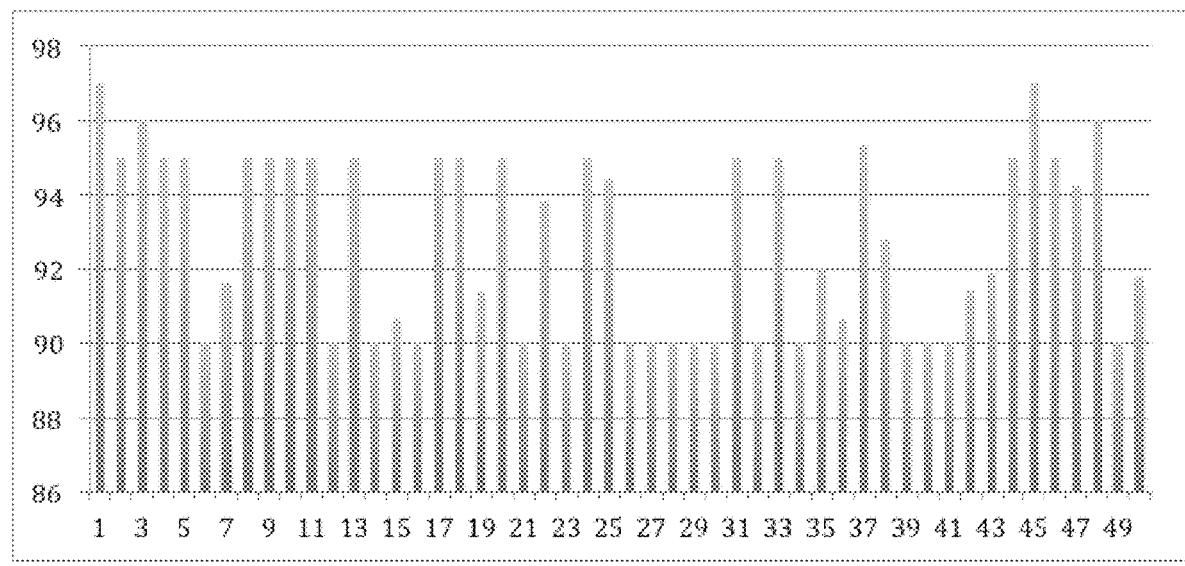
FIG. 9 depicts oxygen saturation in a sound association test according to an embodiment of the present disclosure.
Figure 10:
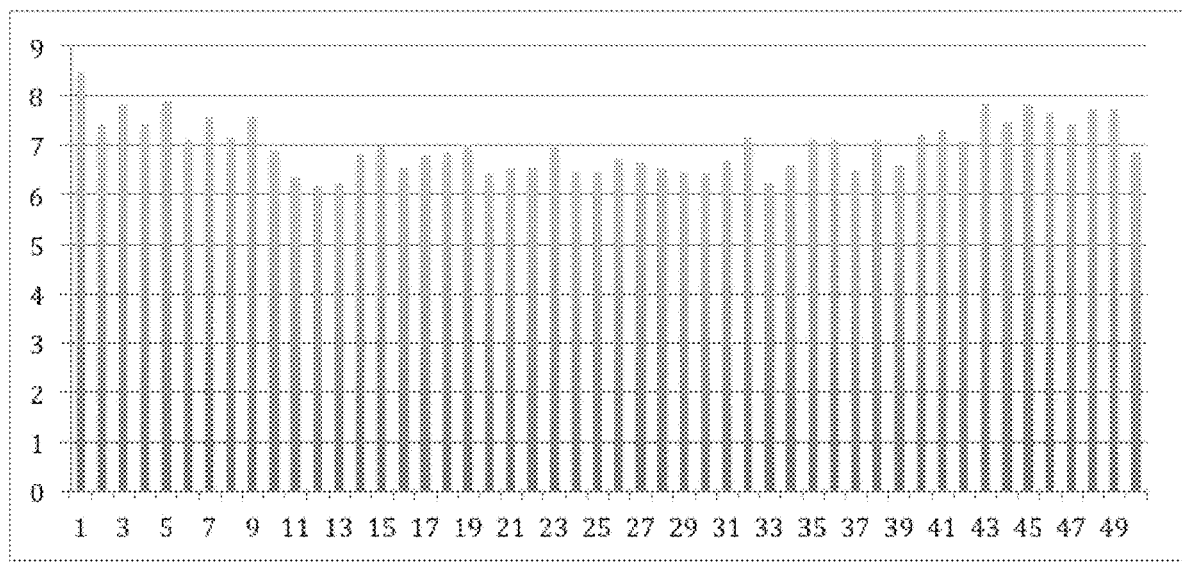
FIG. 10 depicts galvanic skin response in a sound association test according to an embodiment of the present disclosure.
Figure 11:
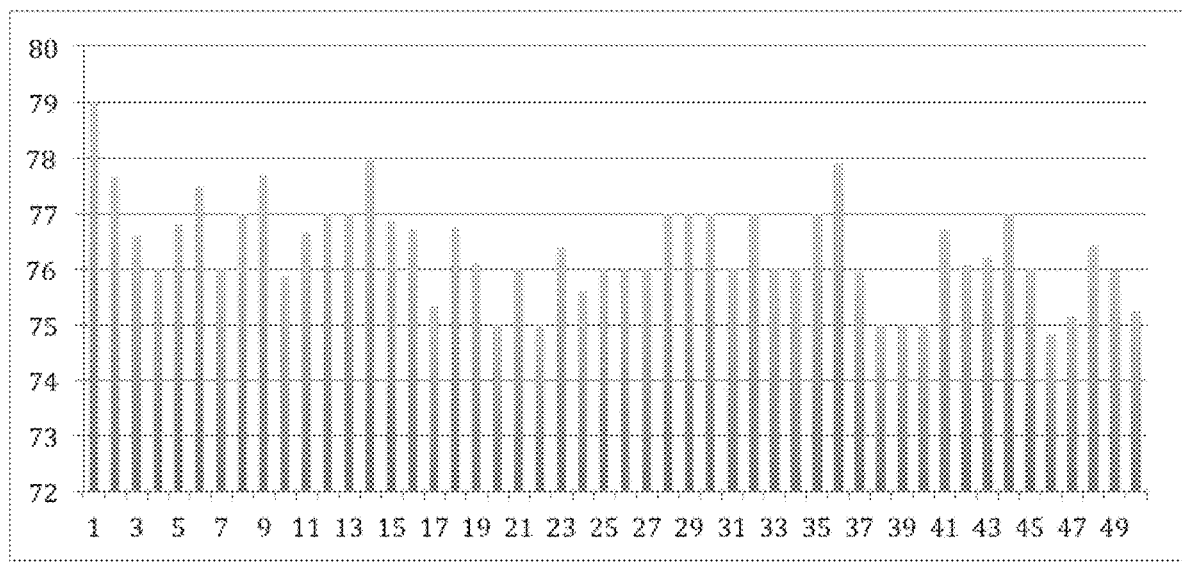
FIG. 11 depicts average pulse in a sound association test according to an embodiment of the present disclosure.
Figure 12:
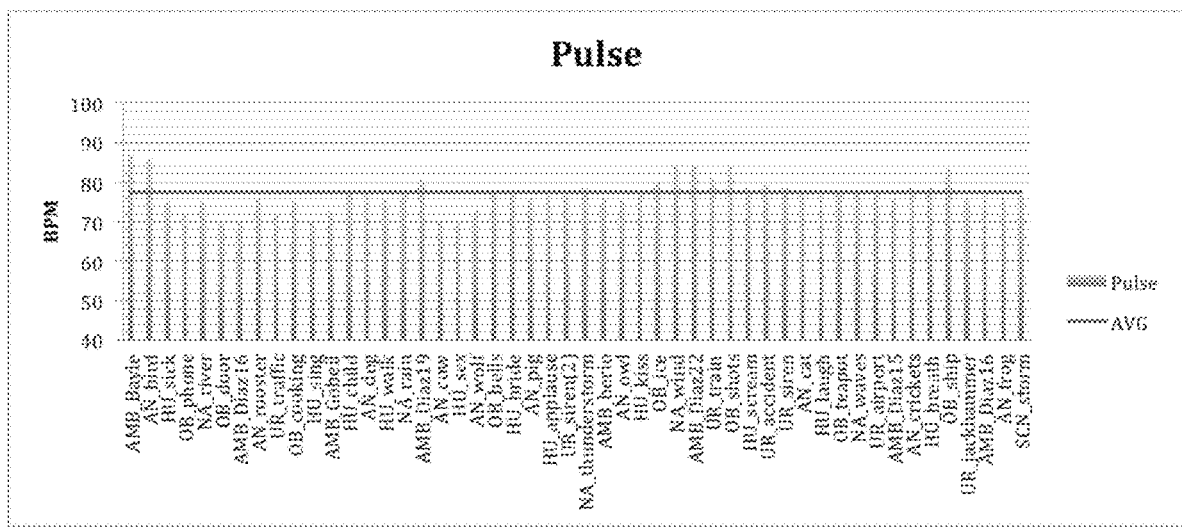
FIG. 12 depicts pulse readings in a sound association test according to an embodiment of the present disclosure.
Figure 13:
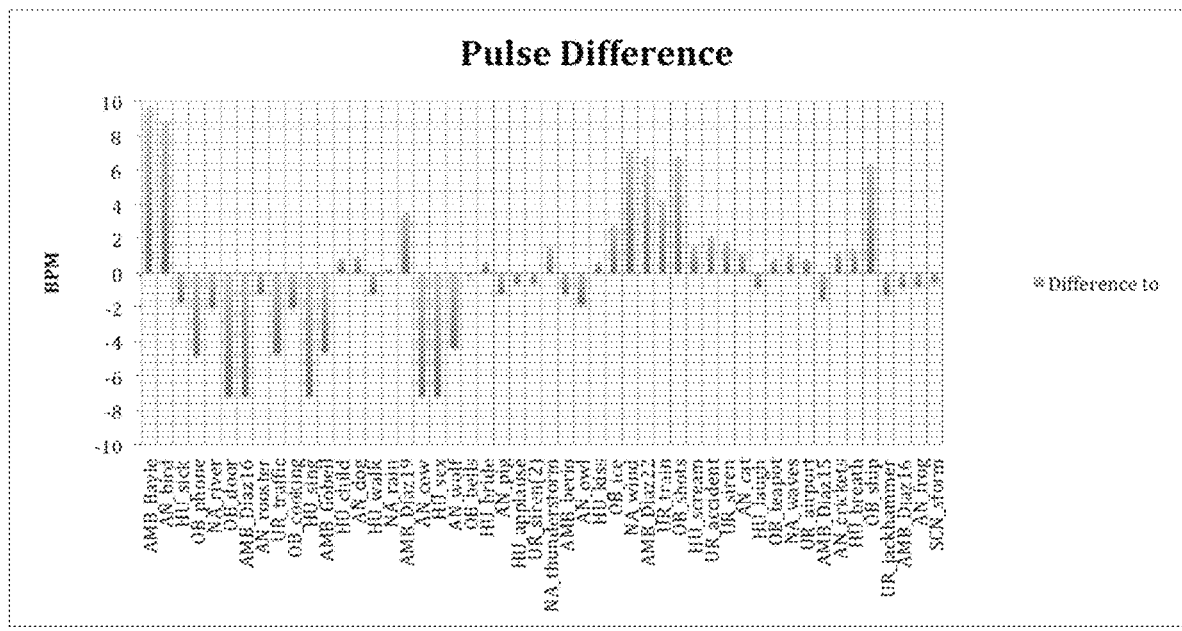
FIG. 13 depicts pulse difference in a sound association test according to an embodiment of the present disclosure.
Figure 14:
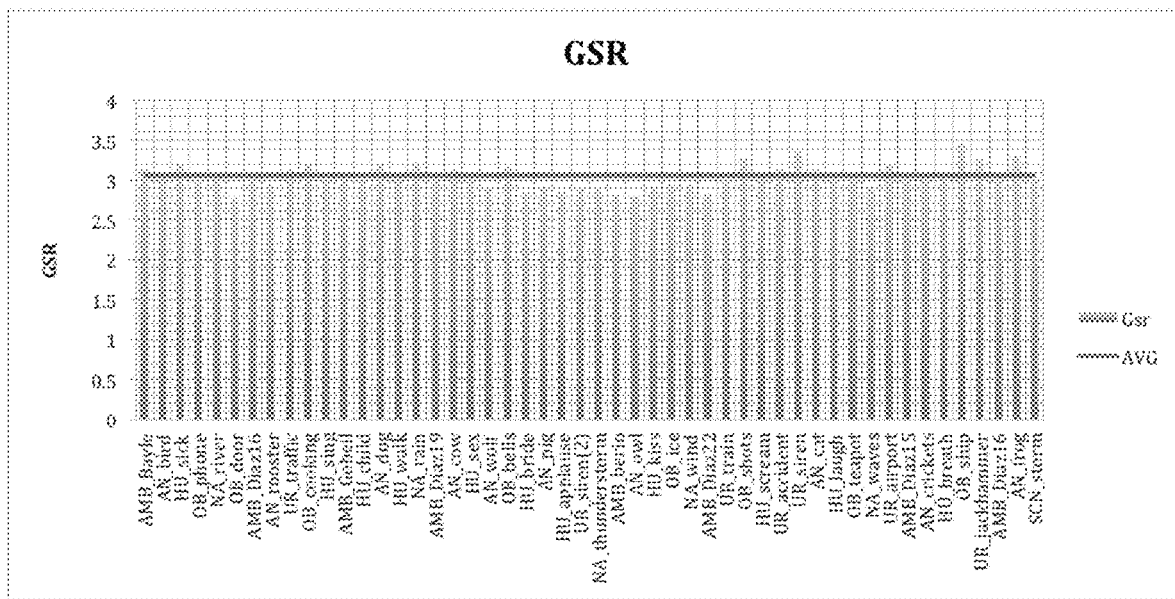
FIG. 14 depicts galvanic skin response (bar graph with average) in a sound association test according to an embodiment of the present disclosure.
Figure 15:
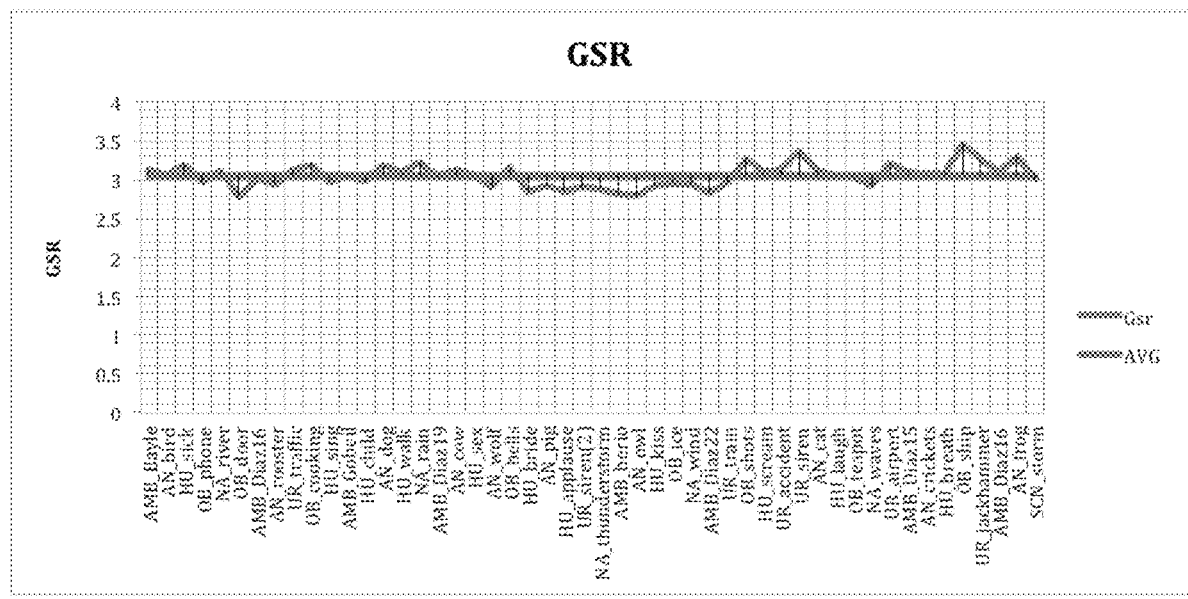
FIG. 15 depicts GSR (average difference) in a sound association test according to an embodiment of the present disclosure.
Figure 16:
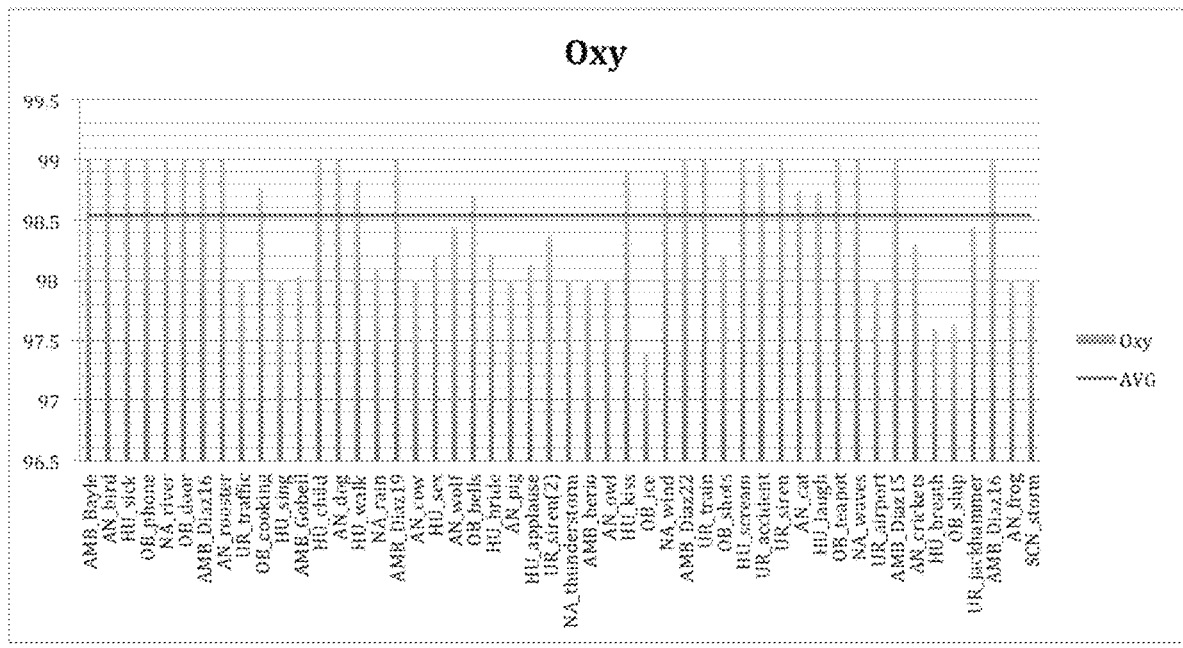
FIG. 16 depicts oxygen saturation in a sound association test according to an embodiment of the present disclosure.

FIGS. 9-11 include some early renderings of physiological data taken from subjects within the sample population. The X-axis of the test represents the time and presentation of consecutive stimuli. The Y-axis represents the physiological element being measured. The early version of the test included only numerical representations (every other number) in the X-axis of the stimuli.

Later versions of the graphs present all the words and or the sounds on the X-axis for easier identification. An examiner can quickly identify a stimulus word or sound that may be of interest. The subsequent graphs also introduce an "average" line that indicates the average measurement of that particular physiological element. This allows the examiner to quickly identify occurrences above the average. Each bar in the graph represents the average measure of physiological data for that particular stimulus. This feature is particularly useful with stimuli that represent a long period of time such as reactions over 30 s. In such a case, the bar graph would represent the average physiological reading for a sample that occurred over 30 s displaying that averaged value along the Y-axis.

Two additional types of graphs are presented for each physiological measurement. One is a bar graph representing each stimulus word or sound with an average marker the other. The second graph establishes an average baseline for the subject's physiological data being measured and then demonstrates incidents above and or below such average baseline. FIGS. 12-16 provide examples of two such graphs rendering information on pulse and galvanic skin response (GSR).

Results

General Considerations

Although numerous versions of the test were conducted, the primary purpose for the administration of the early versions was the design and construction of a stable platform. The results of early versions are not reported herein as they constitute elementary design phases concerned with making corrections. The modifications were primarily those of communication, compatibility and translation of data between programs. Additional early design concerns included testing consecutive versions for the introduction and inclusion of audio and video components, timing factors, recording of physiological data, and formatting constituents for the presentation of information. The trial administrations reported in the results section of this presentation were conducted upon the completion of platform considered stable enough to produce results without software errors. The platform was considered stable for administration after version 25.

The results are expected to provide comparative information between the two tests useful in informing the associative properties of sounds. General information in the form of factual results from the current sample population will be presented. Results will also include a general discussion of protocols as well as the subject's comparative comments and observations addressing the differences between the "word" and "sound" association. The observations and comments of subjects help to provide preliminary insights into the potential of associative properties of sounds and help to inform the design of the test.

Method

The tests were conducted during scheduled sessions. The subjects were informed of the nature of the test and the purpose of the design. The subjects were allowed time to ask questions and present any concerns. Subjects were allowed to choose whether to include physiological devices or not. Once subject was comfortable and at ease with the project the experiment process would begin. Prior to commencing the test a set of instructions is given. Both the "word" and the "sound" section of the test contain its own set of instructions.

The test may be divided into two major sections: the "Word" and the "Sound" portion of the test, each containing 50 words and 50 sounds respectively as stimuli. Each portion of the test (Words and Sounds) is further divided into three stages; the first trial with timed reactions, the second trial with reproductions, and a final discussion. The "word" association portion of the test was administered first, recording both reactions and reproductions. Time was allowed between each section for the subject to pause. The "sound"

portion of the test, both reactions and reproductions, was given after the administration of the words. All information was exported to excel for further notation of complex indicators. A final discussion of contents was arranged at a later date within the week. During the final portion of the test the examiner gathered associative information to the reactions and responses to the stimulus words/sounds. Additional information gathered included subject's comments and observations on their experience between both tests.

Sample

The findings represent the administration of the test to a sample population of eight subjects. The subjects are comprised of male and female participants in an age range of 27 to 56 years of age. The subjects were randomly selected and represent persons professionally engaged in a variety of occupations. Two subjects had high school degree education, three had bachelor degree education and the remaining three had master level education. The majority of the participant's native language was English. Two participant's native language was Spanish, however, these participants were fluent in English as well. The digital samples of the stimulus word in English were used throughout the test. Subjects responded in English to the stimulus words. For consistency of within testing, the responses to sampled sounds were requested to be in English as well.

Discussion of Complex Indicators

While the use of the stimuli (words and sounds) between the two tests differs, it is presumed that the complex indicators used for the word association will also pertain to the sound stimulus. Therefore, the same complex indicators used in the original word association test have been used throughout the subject sample test and applied to the sound association test as well. The use of the similar complex indicators as in the word association test is based upon Jung's criteria for the identification of complexes, as discussed in the complex theory and word association section of this presentation.

Responses that are over the mean average response time, no response or a different response reproduction to stimuli word/sound are considered complex indicators. So too are, gestural reactions, noises, rhymes, multiple word responses, and other "subtle differences in responses . . . all indicative of "complex indicators" . . . helpful for finding out things people cannot or will not talk about" (Jung, C W 2, 1973). However, due to the unique nature between these two sets of stimuli, certain questions and consideration become apparent.

The primary difference amongst the two tests has to do with the contrasting nature of the stimulus; vocal linguistic words, on the one hand, and "sounds" (as defined in this study) on the other. The most noticeable difference is that of time. The utterance of a "word" as a stimulus is a relatively short event in contrast to the presentation of a sound. The words in the word association test can be articulated within a very short time frame ($\leq 1$ sec). The presentation of the sound stimulus, on the other hand, differs in that it takes longer period of time to present.

What constitutes the proper length of time for a sound stimulus is still a matter of consideration. However, it was noted upon the administration of early test trials that shorter sample segments ($\leq 3$ sec) of time did not allow for a clear representation of the sonic stimulus. Neither were excessively long samples (+30 sec) considered adequate as people tended to delay their responses until then end of the sample. For the purpose of this test, the sample length of sounds has been set at ten (10) seconds.

The importance of these differences is that response time to stimulus between words and sounds will naturally differ. The mean response to sounds is approximately double that of words due in part to the length of the sound sample. This difference between stimuli is balanced out in that the both response times represent the average mean for its own test. This is evidenced by the results of the test that indicate that while the median response times between words and sounds differed ($\geq 2$), the individual responses over PM remained relatively similar between the two stimuli. (See Responses over the Mean >PM).

Certain complex indicators, found in the original word association test seem suitable for use with both tests. Categories such as failed reproduction, multiple word responses, responses with gestures, slip of tongue, foreign language, and noises are relatively straight forward and do need any special consideration. There are however, certain categories that may need special consideration due to the evident difference between words and sounds.

One observation in this regard includes the tendency of subjects to identify sounds rather than provide associations. This inclination provided an interesting question as to how this type of response might be considered. One possible way to categorize an "identification" would be to consider it as a repetition. This would be similar in effect to a subject repeating a word. For example, one hears the sound of a "dog" and responds "dog". Another possibility was to consider "identification" as a factual response. This consideration seemed appropriate in that factual responses pertain to the "meaning" of a word, in much the same way, as one would "identify" a sound.

Further questions arise with the complex indicator category of rhyme and completion. Would the use of rhyme or completion be convincing indicator for a sound stimulus and how would this work? For example, hearing the sound of water and responding "fall" would in essence create the word "waterfall".

An additional concern, directly related to the design of the sound association test, was the reflection as what may constitute as "misheard" sound, similar to the complex indicator of "misheard" word. The fact that certain sounds were misheard can be attributed to design issues such as the audio quality and fidelity of the sound used, its amplitude and its location amongst other sounds. However, when such sounds are only "misheard" relatively infrequently and normally recognized by other subjects one must ask whether the "mishearing" is a consequence of the sound itself or related to the subject.

The consideration for the use of similar complex indicators within the sound association portion of the test is further expounded upon in the factual results. Whether certain categories of complex indicators are pertinent with the use sounds is a matter for further examination. The design of the test, however, responds to these kinds of questions by permitting a strategic degree of flexibility. Should certain complex indicators used with the sound association test be considered unreliable, such indicators can be removed from current studies and new data can be automatically generated. As future administrations of the test reveal new results, new "complex indicators" specific to sound stimulus can be considered and eventually added and implemented into the sound component of the test.

Factual Results

This section presents the general findings from the subject sample used. The factual findings of all subjects for both the word and the sound association will be presented in comparative manner. Specific reactions, responses, and context material that are deemed relevant to the comparative study of the stimulus will be discussed.

The sample population included eight persons, male and female ranging in age from 27 to 56 all with a minimum of a high school education (See sample). The current test is divided into two components representing 50 words and 50 sounds. Each of these sections further divided into two sections, reaction responses and reproductions. Each test subject therefore represents 200 responses; that is, 100 word responses (50 reactions/50 reproductions) and 100 sound responses (50 reactions/50 reproductions). For a population sample of eight (8), this represents 1,600 potential responses. This number does not include the discussion of context or subject comments during the final third stage of the experiment.

Formal Evaluation
Complex Indicators.

The following tables present a comparative exposition of the complex indicator results for subjects between words and sounds respectively.

TABLE 3

Results Complex Indicators

Subject 1 Words/Sounds

| | | | |
|---|---|---|---|
| Median for words 1-50: | 23.0 | Median for sounds 1-50: | 43.5 |
| Responses Over PM | 22 | Responses Over PM | 22 |
| Repeated SWs: | 0 | Repeated SWs: | 4 |
| SWs with noise: | 2 | SWs with noise: | 5 |
| SWs with failed repro: | 19 | SWs with failed repro: | 28 |
| Rhymes or completions: | 2 | Rhymes or completions: | 0 |
| Multi-word responses: | 3 | Multi-word responses: | 26 |
| Mis-heard SW: | 2 | Mis-heard SW: | 0 |
| Responses with gestures: | 7 | Responses with gestures: | 5 |
| Perseverations: | 0 | Perseverations: | 0 |
| No response in 30 s: | 0 | No response in 30 s: | 0 |
| Stereotypes: | Fun; Sad (Sadness) | Stereotypes: | |
| Mediate responses: | 0 | Mediate responses: | 0 |
| Meaningless responses: | 0 | Meaningless responses: | 0 |
| Defensive reactions: | 3 | Defensive reactions: | 4 |
| Slip of the tongue: | 0 | Slip of the tongue: | 0 |
| Foreign language: | 0 | Foreign language: | 0 |
| Stutter/mispronunciation: | 0 | Stutter/mispronunciation: | 0 |
| Factual Responses: | 29 | Factual Responses: | 17 |
| Egocentric Responses: | 21 | Egocentric Responses: | 33 |

Subject 2 Words/Sounds

| | | | |
|---|---|---|---|
| Median for words 1-50: | 18.0 | Median for sounds 1-50: | 28.0 |
| Responses Over PM | 15 | Responses Over PM | 23 |
| Repeated SWs: | 0 | Repeated SWs: | 5 |
| SWs with noise: | 5 | SWs with noise: | 9 |
| SWs with failed repro: | 16 | SWs with failed repro: | 13 |
| Rhymes or completions: | 1 | Rhymes or completions: | 1 |
| Multi-word responses: | 6 | Multi-word responses: | 9 |
| Mis-heard SW: | 2 | Mis-heard SW: | 2 |
| Responses with gestures: | 6 | Responses with gestures: | 17 |
| Perseverations: | 0 | Perseverations: | 0 |
| No response in 30 s: | 1 | No response in 30 s: | 1 |
| Stereotypes: | | Stereotypes: | |
| Mediate responses: | 0 | Mediate responses: | 0 |
| Meaningless responses: | 0 | Meaningless responses: | 0 |
| Defensive reactions: | 0 | Defensive reactions: | 0 |
| Slip of the tongue: | 0 | Slip of the tongue: | 0 |
| Foreign language: | 0 | Foreign language: | 0 |
| Stutter/mispronunciation: | 0 | Stutter/mispronunciation: | 0 |
| Factual Responses: | 13 | Factual Responses: | 15 |
| Egocentric Responses: | 37 | Egocentric Responses: | 35 |

Subject 3 Words/Sounds

| | | | |
|---|---|---|---|
| Median for words 1-50: | 18.0 | Median for sounds 1-50: | 33.5 |
| Responses Over PM | 22 | Responses Over PM | 23 |
| Repeated SWs: | 1 | Repeated SWs: | 0 |

TABLE 3-continued

Results Complex Indicators

| | | | |
|---|---|---|---|
| SWs with noise: | 11 | SWs with noise: | 6 |
| SWs with failed repro: | 22 | SWs with failed repro: | 36 |
| Rhymes or completions: | 1 | Rhymes or completions: | 0 |
| Multi-word responses: | 3 | Multi-word responses: | 11 |
| Mis-heard SW: | 6 | Mis-heard SW: | 0 |
| Responses with gestures: | 15 | Responses with gestures: | 24 |
| Perseverations: | 0 | Perseverations: | 0 |
| No response in 30 s: | 0 | No response in 30 s: | 0 |
| Stereotypes: | Free, none | Stereotypes: | |
| Mediate responses: | 0 | Mediate responses: | 1 |
| Meaningless responses: | 0 | Meaningless responses: | 0 |
| Defensive reactions: | 0 | Defensive reactions: | 0 |
| Slip of the tongue: | 0 | Slip of the tongue: | 0 |
| Foreign language: | 0 | Foreign language: | 0 |
| Stutter/mispronunciation: | 0 | Stutter/mispronunciation: | 0 |
| Factual Responses: | 18 | Factual Responses: | 15 |
| Egocentric Responses: | 32 | Egocentric Responses: | 35 |

Subject 4 Words/Sounds

| | | | |
|---|---|---|---|
| Median for words 1-50: | 20.5 | Median for sounds 1-50: | 41.0 |
| Responses Over PM | 21 | Responses Over PM | 22 |
| Repeated SWs: | 0 | Repeated SWs: | 7 |
| SWs with noise: | 5 | SWs with noise: | 2 |
| SWs with failed repro: | 22 | SWs with failed repro: | 18 |
| Rhymes or completions: | 5 | Rhymes or completions: | 0 |
| Multi-word responses: | 7 | Multi-word responses: | 3 |
| Mis-heard SW: | 5 | Mis-heard SW: | 0 |
| Responses with gestures: | 12 | Responses with gestures: | 19 |
| Perseverations: | 0 | Perseverations: | 0 |
| No response in 30 s: | 0 | No response in 30 s: | 2 |
| Stereotypes: | | Stereotypes: | |
| Mediate responses: | 1 | Mediate responses: | 1 |
| Meaningless responses: | 0 | Meaningless responses: | 0 |
| Defensive reactions: | 0 | Defensive reactions: | 3 |
| Slip of the tongue: | 0 | Slip of the tongue: | 0 |
| Foreign language: | 2 | Foreign language: | 2 |
| Stutter/mispronunciation: | 0 | Stutter/mispronunciation: | 0 |
| Factual Responses: | 14 | Factual Responses: | 14 |
| Egocentric Responses: | 36 | Egocentric Responses: | 36 |

Subject 5 Words/Sounds

| | | | |
|---|---|---|---|
| Median for words 1-50: | 27.5 Spanish | Median for sounds 1-50: | 69.5 Spanish |
| Responses Over PM | 23 | Responses Over PM | 23 |
| Repeated SWs: | 1 | Repeated SWs: | 5 |
| SWs with noise: | 17 | SWs with noise: | 12 |
| SWs with failed repro: | 8 | SWs with failed repro: | 19 |
| Rhymes or completions: | 1 | Rhymes or completions: | 0 |
| Multi-word responses: | 3 | Multi-word responses: | 10 |
| Mis-heard SW: | 7 | Mis-heard SW: | 1 |
| Responses with gestures: | 18 | Responses with gestures: | 14 |
| Perseverations: | 0 | Perseverations: | 0 |
| No response in 30 s: | 0 | No response in 30 s: | 3 |
| Stereotypes: | who, what | Stereotypes: | noche-4/ night-4 "4- muy desagradable" |
| Mediate responses: | 1 | Mediate responses: | 1 |
| Meaningless responses: | 0 | Meaningless responses: | 0 |
| Defensive reactions: | 0 | Defensive reactions: | 3 |
| Slip of the tongue: | 0 | Slip of the tongue: | 0 |
| Foreign language: | 2 | Foreign language: | 19 |
| Stutter/mispronunciation: | 0 | Stutter/mispronunciation: | 1 |
| Factual Responses: | 16 | Factual Responses: | 22 |
| Egocentric Responses: | 34 | Egocentric Responses: | 28 |

Subject 6 Words/Sounds

| | | | |
|---|---|---|---|
| Median for words 1-50: | 15.0 | Median for sounds 1-50: | 26.5 |
| Responses Over PM | 20 | Responses Over PM | 21 |
| Repeated SWs: | 0 | Repeated SWs: | 6 |
| SWs with noise: | 6 | SWs with noise: | 6 |
| SWs with failed repro: | 8 | SWs with failed repro: | 14 |
| Rhymes or completions: | 3 | Rhymes or completions: | 2 |
| Multi-word responses: | 1 | Multi-word responses: | 5 |
| Mis-heard SW: | 0 | Mis-heard SW: | 0 |
| Responses with gestures: | 14 | Responses with gestures: | 20 |
| Perseverations: | 0 | Perseverations: | 0 |

TABLE 3-continued

Results Complex Indicators

| | | | |
|---|---|---|---|
| No response in 30 s: | 0 | No response in 30 s: | 0 |
| Stereotypes: Around(5); Many(4) | often(5) | Stereotypes: | footsteps |
| Mediate responses: | 0 | Mediate responses: | 0 |
| Meaningless responses: | 0 | Meaningless responses: | 0 |
| Defensive reactions: | 0 | Defensive reactions: | 0 |
| Slip of the tongue: | 0 | Slip of the tongue: | 0 |
| Foreign language: | 0 | Foreign language: | 0 |
| Stutter/mispronunciation: | 0 | Stutter/mispronunciation: | 0 |
| Factual Responses: | 25 | Factual Responses: | 24 |
| Egocentric Responses: | 24 | Egocentric Responses: | 26 |

Subject 7 Words/Sounds

| | | | |
|---|---|---|---|
| Median for words 1-50: | 14.0 | Median for sounds 1-50: | 15.0 |
| Responses Over PM | 8 | Responses Over PM | 19 |
| Repeated SWs: | 0 | Repeated SWs: | 11 |
| SWs with noise: | 0 | SWs with noise: | 1 |
| SWs with failed repro: | 13 | SWs with failed repro: | 14 |
| Rhymes or completions: | 1 | Rhymes or completions: | 1 |
| Multi-word responses: | 3 | Multi-word responses: | 7 |
| Mis-heard SW: | 3 | Mis-heard SW: | 4 |
| Responses with gestures: | 22 | Responses with gestures: | 20 |
| Perseverations: | 0 | Perseverations: | 0 |
| No response in 30 s: | 0 | No response in 30 s: | 0 |
| Stereotypes: sadness(5) | people(3); dog(3) | Stereotypes: | Trouble(4) |
| Mediate responses: | 0 | Mediate responses: | 0 |
| Meaningless responses: | 0 | Meaningless responses: | 0 |
| Defensive reactions: | 1 | Defensive reactions: | 0 |
| Slip of the tongue: | 0 | Slip of the tongue: | 0 |
| Foreign language: | 0 | Foreign language: | 0 |
| Stutter/mispronunciation: | 0 | Stutter/mispronunciation: | 0 |
| Factual Responses: | 25 | Factual Responses: | 21 |
| Egocentric Responses: | 25 | Egocentric Responses: | 29 |

Subject 8 Words/Sounds

| | | | |
|---|---|---|---|
| Median for words 1-50: | 14.0 | Median for sounds 1-50: | 27.0 |
| Responses Over PM | 18 | Responses Over PM | 24 |
| Repeated SWs: | 1 | Repeated SWs: | 4 |
| SWs with noise: | 4 | SWs with noise: | 6 |
| SWs with failed repro: | 6 | SWs with failed repro: | 6 |
| Rhymes or completions: | 3 | Rhymes or completions: | 0 |
| Multi-word responses: | 0 | Multi-word responses: | 6 |
| Mis-heard SW: | 5 | Mis-heard SW: | 1 |
| Responses with gestures: | 14 | Responses with gestures: | 25 |
| Perseverations: | 0 | Perseverations: | 0 |
| No response in 30 s: | 1 | No response in 30 s: | 0 |
| Stereotypes: | | Stereotypes: Jungle, city, wedding | |
| Mediate responses: | 0 | Mediate responses: | 1 |
| Meaningless responses: | 0 | Meaningless responses: | 0 |
| Defensive reactions: | 0 | Defensive reactions: | 0 |
| Slip of the tongue: | 0 | Slip of the tongue: | 0 |
| Foreign language: | 0 | Foreign language: | 0 |
| Stutter/mispronunciation: | 0 | Stutter/mispronunciation: | 0 |
| Factual Responses: | 21 | Factual Responses: | 16 |
| Egocentric Responses: | 29 | Egocentric Responses: | 34 |

Median for Words/Sounds

Overall results for eight subjects sample indicates that the median reaction time for the sounds is larger than that for the words. The difference in response time between words and sounds is approximately double for the sounds in most cases. One reason for the larger mean response time for the sounds is that the each sound sample used in the sound association test represents 10 seconds of time.

The sound association test according to embodiments of the present disclosure presents new ground and many questions, such as how to present the sounds, are still under consideration. This consideration again pertains to the essential differences between words and sounds. In this case, the longer stimulus resulted in longer responses because reactions happen during the presentation of the sound stimulus not afterwards.

The presentation of the instructions given to the subject prior to testing is an important element in the resulting mean time. Even though the instructions to reply "as quickly as possible" were given before the test, certain subjects tended to hesitate with responses. This could be attributed to the fact that the majority of the subjects were unfamiliar with the examination process and exhibited a degree of restraint and/or forced thoughtfulness.

In "The Association Experiment in Therapeutical Practice" (Kast, 1980 p. 10), the time measure is indicated as follows: "The experimenter starts to measure the time when the first vowel of the first accentuated syllable is pronounced and ends at the first audible letter of the reaction word spoken by the subject". With the sound stimulus there is no similar criteria as the "first vowel of the accented syllable" (Kast, 1980).

This brings us back again to questions concerning the essential difference between the presentation of words as opposed to sound stimulus. As mentioned before the rendering of a word is a relatively short event (≤1 sec) whereas a sound requires more time and is standardized in this test at 10 sec.

Following the above-mentioned instructions, one begins the timing of the reaction to the stimulus words with the "first vowel of the accented syllable". Most words in the word association test can be articulated in a single syllable, that is to say they are monosyllabic ('cat", "go", "red", etc). In these cases the timing would begin directly after the first articulation. In the case of multisyllabic words such as "together" or "family", one could make the point that the timing of the reactions is occurring during the articulation of the stimulus ("first vowel of the accented syllable"). However, or in either case, the timing difference from when one begins the recording of a reaction as to it being "during or after" the word is articulated is essential very marginal (fractions of seconds or difference in one vowel or accent).

Since the timing for the word association begins when the "first vowel of the accented syllable is pronounced" and because the sound stimulus does not have any similar characteristic, for the purpose of this design, the timing of the subject's reaction to the sound begins upon the initial playing of the sound.

As mentioned before, the rendering of a word is a relatively short event (≤1 sec) whereas a sound requires more time and is uniformly set in this test at 10 sec. Thus the longer stimulus resulted in longer (mean) responses time because the timing of reactions happen during the presentation of the sound not afterwards. Depending upon the individual many responses occurred during the presentation of the stimulus. In other cases, however, the response time was lengthened beyond the occurrence of the sound (10 sec) by the tendency of subjects' to listen to the entire sample regardless of the instruction to associate as quickly as possible.

In the case of the response to sounds, it was noticed throughout the initial trials and administration to this subject sample, that participants tended to want to listen to the entire sample before making a response. In earlier trials using shorter samples (no more than 5 seconds), it was observed that instead of offering an association, subjects tended to ask questions to clarify the sound and often requested to "hear more". The design of the test addressed this question of sample length issue by creating a "Set Sample Time" window in the settings menu. This will allow flexibility for the examiner to experiment with timing. However, it was noted that when a subject does pay close attention to the instructions, the response times between words and sounds could be relatively equal. Subject 7, for example, had a one second increase difference between responses to sounds over words.

Additional reasons for the decision to record the timing of reaction during the presentation of the sound relate again to the fundamental differences between the subjects' reactions to sounds as opposed to words. From the results of early pre trial testing it was visually evident that sounds elicited heightened emotional and physical responses. Recording the subject's reaction after the sound (after 10 seconds) might overlook numerous complex indicators such as, gestural responses, noises, and physical motions attributed to listening to the sound. Additionally, one would potentially miss important readings from physiological measurements that occur while the subject is listening to the sound. In embodiments of the present disclosure, the test may observe and record the reactions of the subject during the presentation of the stimulus.

Other examiners, however, may wish to experiment by providing a complete rendering of the sound first and then requesting an association. A difficulty with this approach would be the subject identifying when the stimulus stopped and then identifying the appropriate moment to begin recording a response. There are no linguistic parameters in "sounds" such as vowels or accents that can be used as triggering events. The method involving the simultaneous activation of the sound stimulus and recording of reaction mentioned above was used consistently throughout this research and represents a standardized approach. These and other questions having to do with the essential differences between words and sounds as stimulus continue to be issues for further examination.

TABLE 4

Median Times Results

| Median Time Words | Median Time Sounds |
|---|---|
| Subject 1 = 23.0 | Subject 1 = 43.5 |
| Subject 2 = 18.0 | Subject 2 = 28.0 |
| Subject 3 = 18.0 | Subject 3 = 33.5 |
| Subject 4 = 20.5 (Spanish) | Subject 4 = 41.0 (Spanish) |
| Subject 5 = 27.5 (Spanish) | Subject 5 = 69.5 (Spanish) |
| Subject 6 = 15.0 | Subject 6 = 26.5 |
| Subject 7 = 14.0 | Subject 7 = 15.0 |
| Subject 8 = 14.0 | Subject 8 = 27.0 |
| Average = 18.75 | Average = 35.5 |

Responses Over the Mean (>PM)

While the median response time for the sound association test in comparison to the word association test was normally greater (≥2×), the number of individual responses over the mean (>PM) remained rather constant between the two tests. For example, Subject 1 and Subject 5 had the same number of responses over the mean (>PM) for the word and the sound test alike. Subject 1 had 22 responses over PM for both words and sounds, while Subject 5 had 23 responses over PM for both words and sounds. Subject 3, Subject 4 and Subject 6 all differed by only one more response over PM for the sounds. Subject 2, Subject 7 and Subject 8 show the greatest discrepancy between responses over PM between the words and the sounds. Subject 2 had 15 responses over PM for the words and 23 responses over PM for the sounds (+7). Subject 7 had 8 responses over PM to the words and 19 responses over PM for the sounds (+8). Subject 8 had 18 responses over PM for the words and 24 responses over PM for the sounds (+6). Generally speaking, from the results of these preliminary tests one can see that while there is a large difference in between the median response times amongst the two tests, the number of responses over PM between the two tests does not vary as considerably.

TABLE 5

Response over PM≥

| Subject # | Word Test | Sound Test |
|---|---|---|
| Subject 1 | 22 | 22= |
| Subject 2 | 15 | 23> |
| Subject 3 | 22 | 23> |
| Subject 4 | 21 | 22> |
| Subject 5 | 23 | 23= |
| Subject 6 | 20 | 21> |
| Subject 7 | 8 | 19> |
| Subject 8 | 18 | 24> |
| Totals | 149 | 177 |

Repetitions

Another characteristic of the sound association test that became apparent during the early trials was a propensity to "identify" or "name" the sound. For example, subjects would inevitably respond to the sound of a "cow" or a "bell" by responding, "that's a cow" or "that's a bell". Even though the instructions for the sound portion of the test clearly request an individual to resist the inclination to identify a sound, there was nevertheless a tendency to do so. The propensity to identify "sounds" differed from the inclination to repeat "words" in the word association as evidenced by a diminished frequency of repetitions within the word association segment of the test.

When a subject exhibited the tendency to identify the sound during the testing process, the subject would be reminded of the instructions to provide an association rather than identifying the sound. Occasionally this would prove useful in reducing the identification of sounds, however, the continued need to identify the sounds rather than provide associations became an interesting characteristic of the sound association test. It was considered during the implementation of this design that continual tendency for identification of sounds may be indicative of complex material in that, the lack of associations to the sounds may be representative of repressed memories or contain an unusual amount of emotional content. Therefore, one of the reasons for the increased frequency for repetitions in the sound component of the test was the choice to include the "identification" of sounds as a "repetition" and thus a complex indicator. The "identification" of sound as a repetition indicates 42 more "repetitions" in the sound component of the test as compared to 3 for the word component representing a total of 31 more repetitions (identifications) for the sounds.

TABLE 6

Stimulus Words/Sounds with Repetitions

| Subject # | Word Test | Sound Test |
|---|---|---|
| Subject 1 | 0 | 4> |
| Subject 2 | 0 | 5> |
| Subject 3 | 1> | 0 |
| Subject 4 | 0 | 7> |
| Subject 5 | 1 | 5> |
| Subject 6 | 0 | 6> |
| Subject 7 | 0 | 11> |
| Subject 8 | 1 | 4> |
| Totals | 3 | 42 |

Stimulus Words/Sounds (SW) with Noise

The incident of stimulus accompanied by noise within this subject sample was greater for the word association portion of the test. For the subject sample used herein, the word portion of the test indicated 52 responses with noise, while the sound portion of the test indicated 42 responses with noise. One possible explanation for this discrepancy could be attributed to the large number of noise responses for subject 5, with 17 noise responses to the words and 12 noise responses to the sounds. However, one should take into account that subject 5's native language is Spanish. It was noted that with subject's whose native language is not English, that there may be a tendency to make noise that resembled contemplation of the answer, such as, "Uhmm", "ahhh", "ohhh", etc., possibly indicative of an internal translation process or consideration of the meaning of the word from one language to the other. Conversely, this noise reaction may simply be a personality characteristic of subject 5 as the sound responses also indicated a high number (12) of noise response to sounds.

With the exception of the above example, the distribution of noise responses between the word and the sound portion of the test was relatively similar. For the subject sample used herein, the total number of noises for the word component of the test was 52 while the sound component contained 42; a difference of 10 more noise responses for the word association. Of the subject sample presented herein, three subjects: subject 3, subject 4 and subject 5 all had larger noise responses to words, while four other subjects: subject 1, subject 2, subject 7, and subject 8 all had larger noise responses to sounds. Subject 6 had an equal number of noise responses to words and sounds. (See table 7.)

TABLE 7

Stimulus Words/Sounds with Noise

| Subject # | Word Test | Sound Test |
| --- | --- | --- |
| Subject 1 | 2 | 5> |
| Subject 2 | 5 | 9> |
| Subject 3 | 11> | 6 |
| Subject 4 | 5> | 2 |
| Subject 5 | 17> | 12 |
| Subject 6 | 6 | 6= |
| Subject 7 | 0 | 1> |
| Subject 8 | 4 | 6> |
| Totals | 52 | 42 |

Stimulus Words/Sounds with Failed Reproductions

The occurrence of stimulus with failed reproductions within this subject sample was greater for the sound association portion of the test. The sound portion of the test indicated 148 failed reproductions, while the word portion of the test indicated 114 failed reproductions. This represents a total of 34 more failed reproductions for the sound component of the test. While the results presented here report the factual findings of the administration of the test, one can at the moment only speculate as to the meaning of the larger number of failed reproductions for sound association as compared to the word association component of the test.

Subjects' comments concerning their experience of the sound versus the word association test may help to inform this difference. Subjects often reported that there was a marked experiential difference between the use of words and sounds as stimulus. The variance was most notably characterized as a difference between an "intellectual" exercise for the words, while the "sounds" test represented a more "emotional" experience that tended to elicit a more "moving", "expressive" or "emotive" response. With the word association, subjects indicated that they tended to "think" of a good answer and that despite the instruction to respond "as quickly as possible"; they would nonetheless attempt to make a "smart" or "meaningful" response. Subjects reported that attempting an "intellectual" or "clever" response to sounds was more difficult as the sounds evoked "scenes" of emotional experiences often difficult to describe in single words. The increased attention given to the emotional content of the sound, its reported ability to elicit "scenes" and "memories" may account for the increased incidence of failed reproductions. Subjects reported that sounds had the ability to produce additional memories and thus a tendency to manifest different reproductions.

TABLE 8

Stimulus Words/Sounds with Failed Reproductions

| Subject # | Word Test | Sound Test |
| --- | --- | --- |
| Subject 1 | 19 | 28> |
| Subject 2 | 16> | 13 |
| Subject 3 | 22 | 36> |
| Subject 4 | 22> | 18 |
| Subject 5 | 8 | 19> |
| Subject 6 | 8 | 14> |
| Subject 7 | 13 | 14> |
| Subject 8 | 6 | 6 |
| Total | 114 | 148 |

Rhymes or Completions

The use of rhymes or completions for the subject sample indicated a larger occurrence for the word association over sounds. The total number of rhymes for the word association segment of the test was 17, while rhymes for the sound component of the test numbered 4. This represent a total of 13 more rhymes and completions for the word portion of the test.

One explanation for the larger occurrence of rhyme and completions within the word association section of the test may be that it is easier and more natural to construct a rhyme or completion for a word than it is for a sound. Additionally, one must ask what would constitute a rhyme or completion to a "sound" stimulus. There are as several examples of responses to sounds that have, for the purpose of this test, been considered to be rhymes.

Within the word association component of the test, an example occurrence of a rhyme or completion was the word "free" that elicited the response "dom" making the word "freedom". The incidence of rhymes occurring to sounds can be illustrated by citing examples. For instance, a subject hears the sound of a "pig" and responds by saying "sty", in effect making the word "pigsty". Another subject hears the sound of "thunder" and answers "thunderstorm" or hears the sound of "water" and reacts with "fall" creating the word "waterfall". For the purpose of this design, examples such as these were considered to be in the "rhyme/completion" category of complex indicators.

TABLE 9

Rhymes or Completions

| Subject # | Word Test | Sound Test |
| --- | --- | --- |
| Subject 1 | 2> | 0 |
| Subject 2 | 1 | 1= |

TABLE 9-continued

Rhymes or Completions

| Subject # | Word Test | Sound Test |
|---|---|---|
| Subject 3 | 1> | 0 |
| Subject 4 | 5> | 0 |
| Subject 5 | 1> | 0 |
| Subject 6 | 3> | 2 |
| Subject 7 | 1 | 1= |
| Subject 8 | 3 | 0 |
| Total | 17 | 4 |

Multiple Word Responses

The incidence of multiple word responses was markedly greater for the sound association portion of the test than for the word association. There were a total of 77 multiple word responses (MWR) to the sounds compared to 24 MWR in the word association representing a total of 53 more MWR for the sound component of the test. The increased occurrence of multiple word responses appears to be a specific characteristic of the difference between the use of words and sounds stimulus. Despite the repetition of the instructions to "answer, as quickly as possible, with the very first word, thought or image that occurs to you in connection to that sound. Avoid trying to describe the sound—simply reply by saying the first thing, be it a word, thought, or image that comes up in connection to that sound", subjects found it consistently difficult to do so.

As noted when addressing failed reproductions, subjects reported an experiential difference between the use of words and sounds as stimulus. The discrepancy was most notably characterized as a difference between an "intellectual" exercise for the words, while the "sounds" test represented a more "emotional" experience that tended to elicit a more "moving" or "expressive" and "emotive" response. Subjects reported that attempting an "intellectual" or "clever" response to sounds was more difficult as the sounds evoked "scenes" of emotional experiences often difficult to describe in single words. The reported ability of sounds to elicit these "scenes" would often lead a subject to want to explain the environment or circumstances in which the sound memory occurred for them. This would lead to the use of multiple words in an attempt to describe the "scene".

TABLE 10

Multiple Word Responses

| Subject # | Word Test | Sound Test |
|---|---|---|
| Subject 1 | 3 | 26> |
| Subject 2 | 6 | 9> |
| Subject 3 | 3 | 11> |
| Subject 4 | 7> | 3 |
| Subject 5 | 3 | 10> |
| Subject 6 | 1 | 5> |
| Subject 7 | 3 | 7> |
| Subject 8 | 0 | 6> |
| Total | 26 | 77 |

Misheard Words/Sounds

The frequency of "misheard" words was greater for the word portion than for the sound portion of the association test. For the subject sample used, the word portion of the test indicated 30 misheard words, while the sound portion of the test indicated only 8 misheard sounds. This represents a total of 22 more misheard words attributed to the word component of the test. The tendency to not misunderstand a sound in contrast to mishearing a word also appear to be a characteristic of the sound association test. While words have the potential for homonym (spelled and pronounced the same but with different meaning) and homophones (shared pronunciation regardless of spelling), this characteristic would be difficult to identify in a sound.

Due to the unique difference between words and sounds as stimuli, another question arises as to the equivalency of complex indicators between words and sounds. The question is, what constitutes a "Misheard" sound? As indicated above, the choice and categories of sounds used in the sound association include recognizable sounds as well as ambiguous sounds. The use of recognizable sounds was chosen so as to more closely follow the intent of the word association test. That is to say, excluding any foreign language misunderstanding, the stimulus words found in the word association are readily understood by the participants. So too then, where sounds chosen that represented readily recognizable settings, objects and/or environments.

The incidents of misheard sounds reported within this test sample represent, in the opinion of the examiner, a clear mishearing of the sound. For example, one subject heard the sound of kittens as "puppies". Another heard the sound for cooking in the kitchen as "a small boy urinating" (not only a misheard sound but a multiple word response). These sound samples on the other hand were clearly understood by other subjects. Examples such as these were considered for this test to be indication of misheard sounds and thus complex indicators.

A more questionable interpretation of mishearing a sound includes, for example, one subject who heard the sound of sex as "painful" or "torture". Another heard the sound of sex as "giving birth". It must be noted that these "misheard" sounds were clearly identified by other participants who in turned offered associations. In these cases, however, it may be that the "mishearing" of the sound is more closely accounted for by a complex reaction to the sound. Of course, technical issues such as the quality of the sound, the fidelity, potential ambiguity of the sample itself must also be taken into consideration. However, due to the emotionally charged nature of such a response, examples of such "mishearing" are counted as complex indicators.

The inclusion of ambiguous sounds was an experimental component of the sound association test. Due to the fact that theses sounds are intentionally meant to be unrecognizable, responses to ambiguous stimuli were not considered to be a misheard sound. The use of these ambiguous sounds are based upon the projective hypothesis that indicates that when subjects are exposed to ambiguous stimuli they tend to project their own meaning on to it.

TABLE 11

Misheard Words/Sounds

| Subject # | Word Test | Sound Test |
|---|---|---|
| Subject 1 | 2> | 0 |
| Subject 2 | 2 | 2= |
| Subject 3 | 6> | 0 |
| Subject 4 | 5> | 0 |
| Subject 5 | 7> | 1 |
| Subject 6 | 0 | 0= |
| Subject 7 | 3 | 4> |
| Subject 8 | 5 | 1 |
| Total | 30 | 8 |

Response with Gestures Words/Sounds

The frequency of "response with gestures" was greater for the sound portion than for the word portion of the test. For the subject sample used, the sound portion of the test indicated 136 gestural responses, while the word portion of the test indicated 114 gestural responses. This represents a total of 22 more gestural for the sound component of the test. Due to the visible physical reactions to sounds evident in early testing as well as the subject's feedback concerning the "emotional" quality of the sounds over words, it was expected that the gestural response for sound would be greater than the results indicated herein.

Initial tests that did not include the use of physiological measurement instruments did demonstrate a higher incidence of gestural responses to sounds. It was noted that the introduction of the physiological instruments, used in the later tests within this sample did have an effect on the gestural responses. The devices placed on the fingers and hands of the participants tended to diminish the expression of gestural actions, particularly motions to the face, mouth, eyes or hair. More testing with and without the physiological instruments will be necessary to determine if the sound component of the association test has the characteristic of evoking an increased level of gestural responses.

The use of the physiological instruments also affected the gestural response to words. Subject became more reluctant to demonstrate gestures as they often commented that the physiological measurement devices made them feel as if undergoing a "lie detector" test. Subjects became increasingly aware of their actions and motions while connected to theses devices. Subjects who were not connected to biometric devices appeared unaware or less concerned with their gestures. It would seem then that a subject's level of unawareness of his/her gestural movements helps to reinforce the concept that unconscious expression of gestures are a good complex indicator. The pros and cons of the use of the physiological data devices and their overall affect on the spontaneity of the reactions to stimulus are yet to be evaluated.

TABLE 12

Response with Gestures

| Subject # | Word Test | Sound Test |
|---|---|---|
| Subject 1 | 7> | 5 |
| Subject 2 | 6 | 9> |
| Subject 3 | 15 | 24> |
| Subject 4 | 12 | 19> |
| Subject 5 | 18> | 14 |
| Subject 6 | 14 | 20> |
| Subject 7 | 22> | 20 |
| Subject 8 | 14 | 25 |
| Total | 114 | 136 |

Complex Indicator Rankings for Words and Sounds

This section presents the comparative results of complex indicator (CI) rankings between words and sounds. The tables shown in this section present stimulus words and sound with a complex indicator equal to or greater than one. The remaining stimuli without complex indication is left out from these tables but can be referred to by examining the excel spreadsheet results for each subject within the appendix (Appendix 5 Subject Results—Excel).

Table 12 shows the occurrences of each CI ranking (from 1 to 5) for the each subject for both the word and the sound component of the test. The total number of CI's for the word portion of the test was 234 compared to a total of 288 CI's for the sound portion of the test. This represents a total of 54 more CI's for the sound portion of the test. Within this subject sample, the occurrence of stimuli with complex ranking of 5 occurred 6 times within the word association portion of the test in comparison to 12 times within the sound association component. This represents an increase of 50%, or a total of 6 more CI rankings of 5 for the sound portion of the test. With the exception of CI ranking of 1, the table results indicate, there were more occurrences of higher rankings within the sound association component.

TABLE 13

Complex Indicator Rankings

| Fre-quency: | Words CI rankings | | | | | Sounds CI Rankings | | | | |
|---|---|---|---|---|---|---|---|---|---|---|
| | 5 | 4 | 3 | 2 | 1 | 5 | 4 | 3 | 2 | 1 |
| Subject 1 | 1 | 2 | 4 | 10 | 20 | 2 | 2 | 9 | 15 | 14 |
| Subject 2 | 1 | 1 | 5 | 7 | 11 | 1 | 1 | 10 | 13 | 15 |
| Subject 3 | 0 | 3 | 9 | 14 | 14 | 5 | 4 | 9 | 21 | 9 |
| Subject 4 | 3 | 3 | 5 | 13 | 12 | 1 | 1 | 8 | 17 | 11 |
| Subject 5 | 0 | 5 | 9 | 8 | 10 | 2 | 7 | 14 | 10 | 12 |
| Subject 6 | 0 | 1 | 7 | 9 | 15 | 1 | 1 | 8 | 13 | 14 |
| Subject 7 | 1 | 3 | 2 | 11 | 15 | 0 | 5 | 6 | 15 | 11 |
| Subject 8 | 2 | 1 | 4 | 10 | 7 | 1 | 2 | 5 | 13 | 19 |
| Total | 8 | 19 | 45 | 82 | 104 > | 13 > | 24 > | 71 > | 117 > | 105 |
| Sum Total | | | 258 CI's | | | | | 330 CI's | | |
| Difference | | | | | Sound > by 72 | | | | | |

While further testing with a larger sample of subjects may be necessary to draw more definitive conclusions, these initial findings reveal the potential of sounds to identify complexes as evidenced by the higher occurrence of CI between the two associative tests.

Factual and Egocentric Responses

The results for factual and egocentric responses differed slightly between the word association and sound association component of the test. For the subject sample used, both the word and the sound association test showed a higher incidence of egocentric responses to factual responses. Factual responses for the words totaled 140 while the factual responses for sounds totaled 128, indicating a total of 12 more factual responses within the word association test. Egocentric responses for the words totaled 210 while egocentric responses for sounds totaled 222, indicating a total of 12 more egocentric responses within the sound association test.

Within the word component of the test only subject 1 had higher factual responses. Subjects 2, 3, 4, 5, 8 all reported higher egocentric responses. Subjects 6 and 7 had a similar occurrence (25) of factual and egocentric responses, which in turn represents an equal division of factual and egocentric responses amongst the fifty words. All subjects within the sound association component of the test showed higher number of egocentric responses over factual responses. This may be accounted for by the question of what may constitute a factual and egocentric response to a sound stimulus.

The criteria for an egocentric response to "sounds" are herein considered to be similar to that use for the word association test, in that the reactions and responses to sounds correspond to personal experiences of the subject. For example, the sound of a "storm" evokes the reaction "peaceful" in a certain subject and not in others, indicative more of a personal experience for that subject. The sound of "wolf" evokes the reaction "lonely" and "lonesome" also indicative of a personal association to the sound. The sound of "rooster" elicits the response "chores" and "duties" because the subject raises and maintains chickens for their eggs.

Additionally, we consider factual responses to sounds when a subject produces a reaction corresponding to the "meaning" of the stimulus. A factual response, for example, may be characterized by the response to the sound of a "siren" by responding "police" or "ambulance". The sound of "coughing" may elicit the response of "sick". The choice of whether a reaction to a sound is factual or egocentric is somewhat arbitrary but can be clarified by associative material provided by the subject. For the purpose of this test, the "identification" of sounds, for example, hearing a "bell" and responding "bell" is also considered to be a factual response.

TABLE 14

Comparison of Factual and Egocentric Responses

| Subject # | Word Test | | Sound Test | |
|---|---|---|---|---|
| | Factual | Egocentric | Factual | Egocentric |
| Subject 1 | 29> | 21 | 17 | 33> |
| Subject 2 | 13 | 37> | 15 | 35> |
| Subject 3 | 18 | 32> | 15 | 35> |
| Subject 4 | 14 | 36> = | 14 | 36> |
| Subject 5 | 16 | 34> | 22 | 28> |
| Subject 6 | 25 | 25= | 24 | 26> |
| Subject 7 | 25 | 25= | 21 | 29> |
| Subject 8 | 21 | 29> | 16 | 34> |
| Totals | 161 | 239> | 142 | 256> |

Both the word and the sound association test indicated higher occurrences of egocentric to factual responses. The word association had a total of 161 factual responses to 239 egocentric responses for a total of 78 more egocentric responses within the word association test. The sound association had a total of 142 factual responses to 256 egocentric responses for a total of 114 more egocentric responses within the sound association test. For the sample population used, this represents higher factual responses for the word association by 19 and higher egocentric responses to the sound association by 27.

Remaining Complex Indicators

The remaining complex indicators were not as prominent throughout the test. These result include the following:

TABLE 15

Remaining Complex Indicators

| Total remaining CI for Test | Words | Sounds |
|---|---|---|
| Stereotypes | 10 | 8 |
| Mediated response | 2 | 4 |
| Defensive reactions | 2 | 10 |
| Slip of tongue | 0 | 0 |
| Foreign language | 4 | 21 |
| Stuttering/mispronunciation | 0 | 0 |
| No Responses in 30 sec | 1 | 6 |

The occurrence of stereotypes was not significantly different between the word and sound portions of the test. The higher incidence of foreign language responses was directly related to the subjects whose native tongue was not English. These subjects tended to respond in their native language when listening to the sounds. One subject found it difficult to remain in one language throughout the sound association portion of the test and presented 19 foreign language shifts. No foreign language indications were present in those subjects whose native language was English. Defensive reactions were more prominent in the sound association and were often accompanied by multiple word responses and comments on the sound. "No response over 30 sec" was more prominent in the sound association portion of the test. However, due to the length of the sound sample used (10 sec) one must consider factoring this element in (See rational in "time over mean" section above). The response to sounds over a certain number of seconds as indicative of a complex is yet to be determined.

General Comments

The consideration of the use of similar complex indicators for the sound association test as those used with the word association is based upon the criteria offered by Jung as to what constitutes a complex indication (Jung, C W 2, 1973). The use of equivalent complex indicators between words and sounds was used to provide a compare and contrast environment that might highlight differences to be further explored. While the above section presents instances that reflect essential differences between the use of word and sounds as stimuli, it is not the intent to offer conclusive results as to their proportional ability to elicit associations. The focus of the design does offer an experimental environment that will permit for further examination of such questions. As mentioned previously, the design addresses these kinds of questions by permitting a certain degree of flexibility within the software that allows for parameters to be changed and further examined.

Subject General Observations

This section will present the participant's comments and observation of subject experiences during the administration of the design. The primary observations and most frequent comments were related to the essential differences between the word and the sound component of the test. A discussion of comments and observations from amongst the subject sample will help to demonstrate their views.

The first set of comments comes from a female subject age 32 currently professionally employed as an administrative secretary. She is unmarried and has two children. This subject states, "I felt that responses to words were more difficult to come up with than responses to sounds. I felt I wanted to have "clever" responses to words but I did not feel this need with the sounds. The word association was more difficult because it seemed more intellectual and I worried about my response, what they might mean, etc. The sound association was more relaxed, I did not feel the need to have a clever response or worry about what my response might "mean". The sound test was more emotional while the words test seemed more "matter of fact".

The same subject continues, "I noticed that it took longer for me to answer to a sound than a word. Maybe that was because I wanted to listen to the entire sound . . . I don't know. It took me longer to respond to sounds and I felt strong desire to not only describe the sounds but also use several words to describe my experience. The second time around however, I did not feel the need to be so descriptive or to respond with multiple words . . . maybe because I had heard the sound already . . . I don't know. Certain sounds such as the screaming and the dogs barking were very emotional . . . some of the sounds can be disturbing".

A 36-year old unmarried male subject currently working as an attorney provides further comments. He states, "The sounds are more difficult to respond to, that is with a single word response, because they bring up a whole internal visual component, a visual landscape and or event. It is hard to respond with just one word because the imagery is richer, and it is not static, it is a sound in motion. The sounds tend to put you "in a place" or create an environment. Your first tendency is to identify the sound but then comes all the emotions and memories that are behind or associated with each sound. With the words there seems to be a "mental" visual image while with the sounds there seems to be an "emotional" visual image".

Additional comments and observations come from a 56-year old female currently in transition between jobs. In reference to the similarities and difference between the word and sound component of the test she offered the following statement. "It's a different approach. I felt I had to change my approach to interpretation. The words activated a more intellectual function and that was not the case with the sounds. I could allow my body to feel the sounds and it was a more complete bodily experience. The sounds would then take me to a place and then I would have an association to that place. I tended to want to close my eyes. With my eyes closed I could easily go to that place. The sound would put me into the environment. Then I would remember all kind of things surrounding that place. For me the sounds were more effective because I did not "think" about answers. With sounds I would hear it and feel it; it was difficult to describe in one word. I had a real strong desire to tell you more about the sound, not with every sound but certainly with some. The sounds felt more experiential."

A 27-year old male student whose native language is Spanish provides the following comments and observations. "Overall it was a very interesting experience. With the words and with the sounds it was very different. First, the words were definitely harder to think about. When I didn't have anything to say most often I would just say something that rhymed. The words didn't really have much impression on me, and also I couldn't relate them to anything in particular". It must be noted, however, that this particular comment may have to do with the fact that the subject's native language is Spanish.

He continues, "For the sounds I had stronger feelings because they (sounds) provoked more memories and emotions. The dog sound, for example, was surprising and evocative of the fear I had to a particular dog when I was a child. All which was because of the unfortunate memory of a stray dog trying to attack me in the street". Concerning the characteristics of certain sounds he states, "There were sounds that reminded me of objects. In general these were the sounds that I liked the most, the ones that had no easy association because then I instinctively tried to associate them to these objects or spaces. Some sounds, like the park or the laughter, were very evocative of these spaces. Also they were hard to answer because although I had an association in my mind (i.e. the laughter reminded of a park next to were I used to live), I had no words to express correctly the feeling. However there were sounds that were very easy to relate like a children laughing or the bells. His final comment was, "I felt that the GSR sensor and the Pulse sensor made me somewhat nervous in general."

A 42-year old married female homemaker provides the following comments. "When I heard the sounds, I could feel them up and own my body . . . deep inside my back and shoulders. Its like the sounds come from around the back of my neck. I later had dream about the sounds and felt similar sensations . . . the dream had a similar sensation, as did the sound . . . as if the dream came from the same place that did the sound . . . but not in a negative way . . . it was a really good experience. The subject continues, "Some sounds were pleasant other can be disturbing. I had several dreams about the sounds. Certain sounds came back to me in my dreams . . . I thought that was interesting".

Some final comments and observations will help to further demonstrate the somewhat relatively similar experiences reported by the subjects as a result of the administration of the sound association test. A 40-year old male married performing artist provides the following insights. "I felt more going on in my mind with the sounds. Words felt a bit "tit-for-tat". The use of sounds felt like a larger scale process, a deeper process, and my body was more involved with the sounds. Oddly enough, sounds were more visual for me . . . I noticed a visual image and tactile feeling sensations. For example, the sound of the pig elicited the smell of pigs, multi-sensory . . . certainly more feeling and more emotion. This would remind me of the farm life and then of the family and how it was back then and on and on." He continues on to say, "words were not quite like that . . . they were more of an intellectual process. Words were more conversational, like a person giving me the word, and then responding."

Additional comments by this subject confirm the views of other participants. Like other participants he states, "It was hard to not identify a sound . . . I felt like I wanted to name the sound. It was also difficult to respond to sounds with one word. I wanted to say more. Sounds seem more open ended as far as offering associations go. As to the length of the sample . . . I tended to answer quickly because that was what the instructions said to do. However, I did feel I like wanting to listen to the entire sound . . . . The use of the biometric devices felt a bit confining. I could not move as much and I felt as if I was in a lie detector test . . . but maybe that was just my perception. The choice of sounds seemed good. There were recognizable sounds and others I could not identify. I liked the ambiguous sounds, they were like an auditory Rorschach, sparking a great deal of material (visual and emotional), even smell in one case."

Effect of Subject's Comments on Design

The comments and observation of the participants were helpful in informing the design of the sound association test according to embodiments of the present disclosure. As the administration of the word association test is well established, most of the comments and observations informing the design pertain to the sound component of the test.

For example, the above comments made evident the tendency to want to "listen to entire sound" or request longer sounds when those provided were too short. In initial trials in which the sounds samples were generally long (+20 sec) participants would tend to delay responses until listening to the entire sound, regardless of the instructions to respond quickly. When sounds were to short participants requested longer samples. Theses comments and observations resulted in the design and implementation of a "Set Sample Time" button in the menu portion of the test with which the examiner could establish a standard time for all sound stimuli. As a result and for the use of this trial experiment, the sample time for sounds was set at 10 seconds. The "Set Sample Time" function will allow for subsequent examiners to explore and help determine a standard length of time. The incidence of subjects taking longer to respond to a sound was also considered as far as responses over >30 sec being indicators of complexes.

The desire to respond to a sound with multiple words was also a characteristic demonstrated by the participants. As one is seeking single response associations, the tendency to respond with multiple words may be viewed as a fundamental characteristic of the use of sound stimulus. The tendency of participants to respond with multiple words serves as a reminder for the examiner to clearly articulate the instructions. The participant can be reminded during the sound association test that he/she will have time to elaborate on the sound during the final portion of the test. However, if the instructions are clearly indicated, the continual use of multi word responses may then be considered a complex indicator in the traditional sense. On the other hand, the tendency to want to say more about the sounds proves beneficial during the presentation of the subject context portion of the test, as participants have more associative material to share.

The comments of Spanish speaking participants also provided insight into the design construction. Foreign language participants often experienced difficulty making associating to words in a language other than their native tongue. This observation led to consideration for implementing digital recordings of the words that could in turn be offered in multiple languages. This function was incorporated into the current design and is currently presented in English. The default presentation is the use of the digitally recorded vocal samples. A "mute" word button was installed to allow the examiners to articulate the words themselves should they choose to do so.

The comments regarding the choice of sounds used in the test also proved helpful to the design. General comments on the use of sounds centered on the ability of sounds to elicit "feelings" and "emotions" as well as, the tendency of sounds to prompt the desire for a "narrative description". These general comments seem to provide an indication that reactions and associations to sounds can offer additional information that may well compliment the findings of the word association test. The comparative comments between words being an "intellectual" experience while sounds are a more "emotional" experience may indicate that the combined use of both tests might provide a more holistic approach to association by accessing different sensory modalities and memory pathways.

Remarks on the use of identifiable sounds had primarily to do with recalling environmental experiences. Some subject even commented that sounds evoked other sensory experiences (visual and olfactory). While some subjects reported confusion or frustration with unidentifiable sound others commented that they preferred these sound as they allowed a greater range of imagination (as in an auditory Rorschach test). Further subject observations included comments that the presentation of identifiable sounds and ambiguous sounds was well balanced.

In regards to the sound association test, a particular subject suggested the use of headphones and or external speakers. Both headphones and external speakers were tried with different results. Certain participants did not like the use of headphone as they reported feeling "isolated" from the testing environment and from interaction with the examiner. The use of headphones did not allow for the examiner to monitor the reactions and responses of the subject, as the examiner could not hear the sound being played within the headset. The examiner could use an additional set of headphones to monitor reaction and responses however this equipment along with the use of biometric devices proved to be too cumbersome and restrictive. As a result the design incorporates the use of external speakers audible to both participant and examiner within the same experimental environment. As the design is flexible, the choice of whether to use headphones or speakers can be left up to the participant and examiner.

While the use of video recording also can be an integral part of the design, certain unforeseen issues arose in regards to its use. During discussions concerning confidentiality and the presentation of the test results, the use of the video component was addressed. The majority test subjects reported that they were not comfortable with the presentation of their video recorded images in the discussion of results with other examiners, as this would invalidate their confidentiality. Certain subjects reported being ok with using certain portions of the video but not the entire presentation of examination.

The sensor (physiological data) information was only applied during the last four trials of the population sample. Nevertheless, these final participants presented similar comments and observations to the use of these devices. While initially the subjects tended to show curiosity and interest about the biometric devices, their final comments were invariably somewhat less enthusiastic. In general, there was an observation that the devices tended to limit gestural and body motions. However, what seemed to be the main complaint was that the addition of these devices made one feel as if they were undergoing a "lie detector" test. Although none of the participants had undergone a lie detector test, subjects commented on the apparent similarity of the biometric devices being used with images of such devices as seen in the media. One is reminded that the methods used in the words association test and the use of physiological data did inform the construction of the so-called "lie detector" test. (Trovillo, P. 1939.)

Subjects that used these devices commented that, "it tended to make them feel nervous". Others felt the need to provide "sane, stable, or rational" answers. These comments may indicate, that for some subjects, the devices have the potential to alter the nature of the responses, as they become more self-conscious and wary of their answers. As mentioned before, the devices were incorporated to demonstrate a design function that allows the reintroduction of physiological measurements in a similar manner as evidenced in early word association testing. The examiner should consider whether the use if these devices may alter the spontaneity of the responses to the stimuli. It is recommended that the examiner discuss the purpose and intended use of theses devices with the participants prior to their use. The use of these devices is not recommended if the subject feels uncomfortable with their use or is ill informed as to their purpose. The sound association test can be administered with or without the use of these devices.

Discussion of Protocols

This research presents the word association test in conjunction with the sound association test. This format provides for a comparative setting between the word and sound association test. Due to the large volume of response data collected, this section will provide a general rather than a comprehensive exposition of protocol responses from amongst the subject sample. A general discussion of remaining subject context responses will help to enhance the presentation of the capacity of sounds association to inform the associative process.

Based upon the substantive context answers provided by a subject in response to the sounds, one can begin to appreciate the potential of sounds to elicit associations. An analysis of the above protocol would seem to indicate the presences of recurring thematic material in both the word and sound association test. While this section does not attempt a full and complete analysis of all the potential complexes and consequent themes, it does demonstrate the presences of parallel complex material obtained from both the word and the sound association test.

The subject provides the following comments in response to the review of the sounds: "My issues with my mother overshadow those of I have with my father . . . father is bad just not as bad . . . maybe bad but in a different way—I definitely got issues around my parents. I relate "perfection" to mother and "abuse" to father, we feared him, and he was powerful in the community. The paradox was that he beats us and the society and community I lived in always talked about how great he was . . . so I resolved the dilemma by believing I was bad. In general, the sound associations are more historical, reminiscent of childhood, they bring up a chain of events".

The first subject presented comments about her parents in response to certain words and/or sounds. From the complex indicators present in the word association test and the above comments offered by the subject in regards to the sounds, one may begin to intimate the presence of a negative parental complex. Also, as we consider the topic of family, it is interesting to note that an apparently unrelated sound can access similar emotional content and shed further light on the nature of a family situation, even with seemingly unrelated sounds such as the sound "cow" or the sound of a "cellphone." It is interesting to observe that while the above sounds are "identifiable" (cow and cellphone) they nonetheless evoke associations not necessarily directly correlated to the sound itself.

Ambiguous sounds on the other hand also demonstrate associative capacities. For example, an ambiguous sound (#27 AMB Berio or AMB_Diaz16) was associated with "suffering" and prompted comments on childhood and family. However, besides just negative or painful experiences, certain sounds ("bells" or "walk") evoked some positive memories.

Discussing words such as "family" or "choice" raised the issue of "mother" for example. While evaluating comments by a subject may help us to formulate an initial picture of the subject's mother, information offered in the sound association helps to reveal other aspects not elicited by the words. Again, another apparently unrelated sound (sound of a "train") brought forth additional associations to mother. The apparently unrelated sound of "airport" and "bride" also prompted an association to mother. Not only do these associations pertain to mother, they displayed other topics not revealed in the word association. The ability of a sound to create a narrative that contains numerous issues is further illustrated by the sound of "bride". Not only did this sound (bride) elicit an association to mother, it also reinforced the subject's account of other experiences by providing a memory of a particular incident. Other themes may be highlighted in the word association test and can center on stimulus words relevant to the theme. Further associations made to sounds also revealed this topic and thus demonstrated the capacity of sounds reinforce and compliment the content of the associations.

With respect to another subject, words and sounds elicited reminders to the influence of subject's community and parental relationships. The context of a sound (such as "applause" or "scream") helped to identify more specific information related to the personal family or family dynamics. This shows the ability of the sound association test to compliment and enhance the findings of the word association. Potentially charged topics that were generally alluded to but not fully disclosed by subject in the word association can be further developed in the sound association. It is observed that the combined use of both stimuli seem to provide a testing environment that is mutually beneficial and supportive.

Additional protocol examples illustrated the capacity of sounds to prompt associations. The subject's reactions and associations to the sounds provided some significant information that was not readily offered in the word association. There were some isolated associations to certain sounds of interest to note due to the unusual and unexpected responses. Similarly misheard sounds can produce different responses.

Ambiguous Sounds

In considering a comparison between the characteristics of sounds and words as stimuli, certain questions arise in connection to the abstract or ambiguous nature of sounds versus words. For example, if a sound can be considered abstract does this same quality pertain to words as well? Deliberating as to whether words can be abstract or not could be simply a question of semantics, that is, what do we mean when we use the word "abstract", is it the right word or does it carry the correct connotation.

The abstract quality of words could be illustrated by contrast between abstract nouns versus non-abstract or "concrete" nouns. A concrete noun (non abstract) would refer to something a person could interact with physically, such as a person, place or thing. An abstract noun, on the other hand, could be an intangible concept, idea, and experience, state of being or other entity not experienced by the five senses. For example, I "love" my son is an action with "love" acting as a verb. I send my "love" could be said to act as an abstract noun since it describes an abstract (or subjective) concept . . . a state beyond the five senses. (We all may experience love but how does "my" love differ form others, how do I interpret it, how has life itself affected my understanding of it, and in what ways is it similar or different form everyone else's understanding and experience). The same could be said of other words such as "peace", "beauty", "success", "truth", "faith", etc. All these words mean different things to different people and to this degree could be said to abstract.

One could consider whether this quality of abstractness relates to sounds as well. Certainly there are many sounds, which we recognize, sounds of nature, sounds of environment, human sounds, and language itself. However, sounds that are not created from natural phenomena or that are unfamiliar to our personal environment may be said to represent abstract sounds. As far as sounds are concerned, an abstract sound may be defined as a synthetically created (not naturally occurring) sonic occurrence. This "abstraction" may not be possible to create linguistically unless we consider languages that are foreign to us.

But rather than using the word "abstract" we could consider whether the character of sounds or words are "ambiguous". In this case, the characteristic of ambiguity may very well be suitable to words and sounds as well. This would mean, for example, that a word could have different meanings and could be open for multiple interpretations, a common occurrence in the word association test.

This ambiguous characteristic would seem to be applicable to sounds as well. This was evident in numerous cases in which a subject "misheard" certain sounds while a majority of subjects could identify the sound. These sonic "misheard" incidents however, could be attributed to personal subjective interpretive ambiguity.

In order to accurately attempt to produce ambiguous (or abstract) sounds one must endeavor to create an experience not readily available or recognizable in one's environment.

For this purpose the ambiguous sound used in this test were derived form non-environmental sources. These sounds were created using electronic synthesizers and music software programs. Basic building blocks of sonic material such as sine or saw waves, amplitude, modulation, and audio processing elements were used in their creation. This type of material is very removed from normal everyday sonic experiences as to be both abstract and ambiguous.

Several of the sounds used are excerpts from electronic music compositions by composers such as Luciano Berio (1925-2003), noted for his experimental and pioneering works in electronic music as well as the work of Jean-Claude Risset (1938-) best known for his contributions to computer music (AMB_Diaz19). The Berio excerpt (AMB_Berio), for example, resembles the use of early sound association material, such as the ambiguously articulated vowels used by Skinner (1936) used in his Verbal Summator.

This concept of ambiguity is related to the projective hypothesis, which states "when a subject attempts to understand an ambiguous stimuli they tend to impose their own meaningful structure with the result that their personal interpretation reflects the unconscious needs, motives and conflicts of the subject" (Gregory, 1996, p. 51 as cited in Merrell, 2003, p. 184). Therefore in relation to the ability of stimuli (words or sounds) to elicit unconscious material, ambiguity is a desirable characteristic as it allows one to freely impose their personal interpretations and unconscious beliefs.

The responses given to the ambiguous sound stimulus demonstrated some interesting characteristics. For a certain subject, two separate responses to the same ambiguous sound brought forth a personal description of his current condition and effort to grow beyond the confines his restrictive environment. The AMB_Dias16 sound elicited, "A ping under the ocean . . . a locator sound echo location . . . a mental image . . . what happening under the surface . . . trying to find where I am . . . how do I find myself when I cant rely on any of the conventional ways in which I was taught . . . who and what else is out there . . . does the ping come back". In response to another ambiguous sound, "I'm testing the emptiness . . . how far is it . . . where is my process leading to?"

The responses to ambiguous sounds varied between subjects. Some enjoyed the sounds because they afforded a degree of imagination while others found the sounds to be disturbing. Certain subjects could offer no response at all. The responses to "AMB_berio" for example, ranged from "theater," "suffering", "and insanity" to "I don't know" and "disgusting". For the most part, the association to ambiguous sounds offered the subject an opportunity to be creative and use imagination. Subjects who had a predilection for subjectivity responded to the ambiguous sound with description of scenes or emotions such as "floating", "peaceful", "impatient", 'beautiful", "chaos", "empty" and references to "mystery" and "nighttime" (egocentric responses). Other subjects whose character could be described as more "formal", "restrained" or "intellectual" found it difficult to respond or associate to ambiguous sounds.

Words have the ability to elicit associations that are specific to the word being used, whether they have a single meaning or multiple meanings. Sound also has the ability to elicit (experiential) association related to the sound being heard. But the quality of abstract sounds, those not related to natural occurrences, synthetically generated sounds, also have the ability to elicit associations. So while associations are normally triggered by events specific to them, we have incidents of associations triggered by unrelated (sonic) material. We could therefore hypothesize that abstract sounds, considered to be "unrelated to the 'natural' environment" and thus not specific to any event, fundamentally have the ability to activate associations. This leads to the potential of eliciting associations from theoretically "unrelated" events.

The above presentation is not a comprehensive representation of all reactions and reproductions in the test sample but rather a general discussion of findings that demonstrate the ability of sounds to elicit associative material. Further exploration of the reactions and reproductions afforded by the sounds (and words) can be viewed by referring to the individual spreadsheet results in the appendix.

Conclusion

This presents the design of an auditory association test founded upon Jung's word association test. The presentation includes a literary review of the historical endeavors at auditory testing and the rational for the construction of a sound association test. An extensive description of the computer application design is presented along with the findings from the administration of the test to a sample population. The software application presents an innovative approach to the administration of association testing. Findings from the pre-trial administration of the test helped to direct the construction of the design. The primary early design changes included addressing compatibility and communications issues between different software applications.

The main design modification from the word association test is the inclusion of "sounds" as associative stimuli. The test offers an experimental "compare and contrast" scenario by presenting the sound association test along side the traditional word association. The software application automatically calculates relevant information to the association test, including measurement of reaction time, calculation of median time, time over prime mean, complex indicators and renders information in graphical format. Several additional innovative features include the integration of video and audio recording which allows the examiner to review subject reactions and responses for clarification of complex indicators. The comments and observation of the participants additionally helped to inform the design, leading for example, to the addition of recorded vocal samples as well as the choice and length of sounds samples. The design incorporates the use of digital vocal recording of the words, a feature that holds the promise of offering the word association test in multiple languages. Although still in the experimental stages of implementation, the design reintroduces the measurement and graphical representation of physiological data found in early versions of the word association test. The design is created to be flexible and allows for other examiners to study and test additional parameters relevant to sound stimulus. The design represents further research in the field of analytical psychology.

This presentation does not seek to establish or stipulate conclusive results as to the comparative benefits or disadvantages of words and sounds to elicit associations. The "compare and contrast" presentation of both tests within the same application does provide a format in which comparative stimuli can be examined and further explored. While the population sample used was relatively small the resulting quantity of information gathered may be adequate to propose some basic observations.

Results of the test given herein offer both a positive outlook for the use of sounds in association as well as some specific challenges. The "comparative" presentation of the sound and word association test does appear to reveal the potential of sounds to elicit associative material, in a similar manner, as does the word association test. This is primarily evident in the context discussions of the subject's reactions and responses to the sounds. As seen in the results section, context responses to sounds often elicited additional and complimentary information not addressed in the word association but nevertheless useful in identifying complexes.

Another interesting consideration for the use of sounds comes from the comments and observation offered by the participants. A predominant view from amongst participants was a reference to the ability of sounds to foster a more "emotional" response as well as recreate "memories", "spaces" and "events". Subjects regularly commented on the differences between words and sounds stipulating that, responding to sounds was more of an "emotional" experience as compared to an "intellectual" process with the words. While the validity of such an observations may be questioned on the basis that such comments represent a purely subjective point of view, it nonetheless, provides an interesting theme. If we consider the construction of complexes, we recall that they originate from the personal unconscious (memories) and are connected to significant events (or archetype) that arouse strong emotions. The comments of subjects in regards to the capacity of sounds to elicit a greater degree of "emotion" and to recreate "spaces" and "memories" connected to significant events, would therefore seem to be directly related to potential of sounds to identify complex material.

Additional challenges are presented by the difference in the nature of the stimuli. The variance between sounds and words revealed a need to consider the general applicability of the similar complex indicators as those utilized in the word association. Indicators that presented challenges within the sound association tests included: rhyme/completion, misheard sound, and repetition. Although the discussion of complex indicators provided rational for the use of the above-mentioned indicators, agreement as to their use from amongst other examiners may be forthcoming.

The research revealed that most complex indicators employed in the word association test could be considered for use within the sound association test. Although timing elements between word and sounds differ the basic concept of responses over the average mean, as a complex indicator, seems to be valid for sounds as well. Other complex indicators suitable for use with the sound association include: gestures, foreign language, mediated responses, multiple word responses, defensive reactions, no response and stereotypes.

The introduction of audio and video recording presented some additional concerns. The video recording of participants has proven helpful in identifying complex indicators that one may be overlooked during the initial administration of the test. Examiners can return to the video component of either the word or the sound association test to review subject reactions, reproductions and other behaviors for further evidence of complex reactions. While the successfully implementation of the video component has proven helpful in identifying complex indicators, subjects have routinely requested that the video footage not be shown in the discussion of results. The video constituent therefore presents another level of confidentiality not present in the current versions of the word association.

The use of digital vocal samples provides some interesting themes for discussion. While the potential to administer the word association test in multiple languages may seem attractive, one must consider the choice of words and whether directly translated words from the original word association are relevant in other languages. The design of this test allows for examiners from different cultural backgrounds to record and use their own list of words that may be more culturally relevant. Additionally, one may explore the differences between administering the test to same subjects using different genders. One could explore difference in response to masculine or feminine voices amongst the same subject. The design of the test allows for an examiner to mute the digital vocal recordings and articulate the words themselves. This function could be used to examine questions of transference that may or may be evident due to the use of recorded sample as opposed to direct articulation of words by an analyst with which the subject may have transference issues.

The use of sounds also provides some interesting topics for discussion. The choice of sounds used for this research was based upon categorization methods established in earlier sound association tests (Stone, 1953). However, the current design permits for the use of numerous alternative sounds than those present herein. Examiners may create folders by choosing their own sounds to be implemented and tested for results. The question as to what may constitute the correct length of a sound sample is still uncertain, however, the design addresses this concern by providing a means to vary length of the sound sample and examine the findings.

An interesting feature of the sound association is that "sounds" are not necessarily related to a particular language. A similar set of sounds may be given cross culturally to different subjects who can then respond in their native language. However, examiners may want to consider the cultural relevance of sounds between contrasting cultures. Again, the question of the relevance of sounds across cultures is an issue for further examination that is addressed by the flexible design and the ability of examiners to create their own collection of sound for testing.

One final addition to the design of the test was the inclusion of a "load study" function that allows the examiner to import a previously saved test back into the application. This function allows for the sharing of completed administration of tests amongst researchers. Previous tests can then be reviewed in other locations by other examiners who can access all information recorded during the test, including audio and video recordings as well as physiological measurements. It is conceivable that the test may be self administered and then sent on to an analyst for final rendering of information. Such an analyst would be able to view the subject throughout the entire administration of the test and make decisions on additional complex indicators.

The flexibility of the current design to allow for the implementation and testing of alternative samples anticipates the creation of a standard "canon" of sounds. A standard canon of sounds would thus be equivalent to an established set of words such as those used in the word association test. More research and testing with alternative sounds and larger population samples are necessary to reveal additional dimensions of sounds to elicit associations. A future component may be the creation of a central data bank that can gather and organize the findings of responses to sounds. Further information regarding the nature of reactions and responses as well as an examination of the number of complexes in response to certain sounds may be useful in identifying psychologically significant acoustic stimuli.

Accumulation of such observations and a more far-reaching penetration into the ability of sounds to elicit associations in a similar manner, as does the word association test, is necessary before making any definitive comparative statements. It is the hope of this examiner that this application and the further efforts of psychologists, researchers, or practicing analysts will help to inform and promote the use of sounds in the associative method.

APPENDICES

Table of Contents

1. Appendix 1 - Sections and Contents - Technical Description
2. Appendix 2 - List Of Words/Sounds
3. Appendix 3 - Operating Instructions
4. Appendix 4 - Subject Complex Indicator Rankings
   - 4.1.1. Subject 1 Words/Sounds
   - 4.1.2. Subject 2 Words/Sounds
   - 4.1.3. Subject 3 Words/Sounds
   - 4.1.4. Subject 4 Words/Sounds
   - 4.1.5. Subject 5 Words/Sounds
   - 4.1.6. Subject 6 Words/Sounds
   - 4.1.7. Subject 7 Words/Sounds
   - 4.1.8. Subject 8 Words/Sounds
5. Appendix 5 - Association Protocols Excel Spreadsheets (SEE ATTACHED FILE)
   - 5.1.1. Subject 1 Words/Sounds
   - 5.1.2. Subject 2 Words/Sounds
   - 5.1.3. Subject 3 Words/Sounds
   - 5.1.4. Subject 4 Words/Sounds
   - 5.1.5. Subject 5 Words/Sounds
   - 5.1.6. Subject 6 Words/Sounds
   - 5.1.7. Subject 7 Words/Sounds
   - 5.1.8. Subject 8 Words/Sounds

Appendix 1

Sections and Contents

Application AT_v27_50

This section presents and describes the different windows and components of the test, as well as their function within the application. The application can reside on the desktop or within the application folder in the main hard drive. The application is currently identified as "AT_v27_50a", that is Association test version 27 using 50 word/sound samples. Upon opening the application one will see the menu page (see FIG. 1). The main "Menu" contains information that is necessary for the test set up.

The main menu includes "Audio On/Off" and "Camera On/Off". These allow for options to conduct the test with or without audio/visual components. A small display window shows the contents of the video. The video component defaults to the built in camera on the lap top computer. Two record functions ("A" and "B") are available. Record "A" is used to record the first trial (reaction) providing a timed stamp of the response. Record "B" is used to record the second trail (reproduction) and does not contain a timing element, as these reproductions do not require timing. In this menu one can read the "elapsed time" during the experiment. One can also read and set the volume input and volume output.

The "Settings" button in the menu page opens the "Settings" window, which is used to initialize the video recording elements used in the test.

All recording functions, audio and visual, are done through USB ports. The program will read and recognize the USB device being used. A "refresh input list" button erases all previous settings and allows for new device settings to be set. Within this menu one can "select source camera". The program defaults to the computer's "built in camera". One can either use the built in laptop computer camera or a variety of other video cameras. The "Select Quality" button allows one to choose the quality recording desired. The inclusion of the video component was a design element that was incorporated to aid in the detection and identification of visual complex indicators. Note that increased resolution, particularly for video, will require larger amounts of hard disk space.

In this "Settings" window one also chooses the length of the audio samples for the test in the "Set time for samples in seconds" window. The inclusion of the ability to set the sample playback time was a design consideration that will allow flexibility in experimentation for subsequent examiners. The ability to determine the length of the sound sample will allow for further examiners to experiment with and eventually consider an "optimal" length of time for the presentation of sound samples. This option will also allow different types of sound association tests to be conducted. One such, test would include the use of a long samples with various sound elements occurring in a linear narrative fashion. The subject would then be asked to create a "story" based upon the sound sequences heard.

Figure 3:
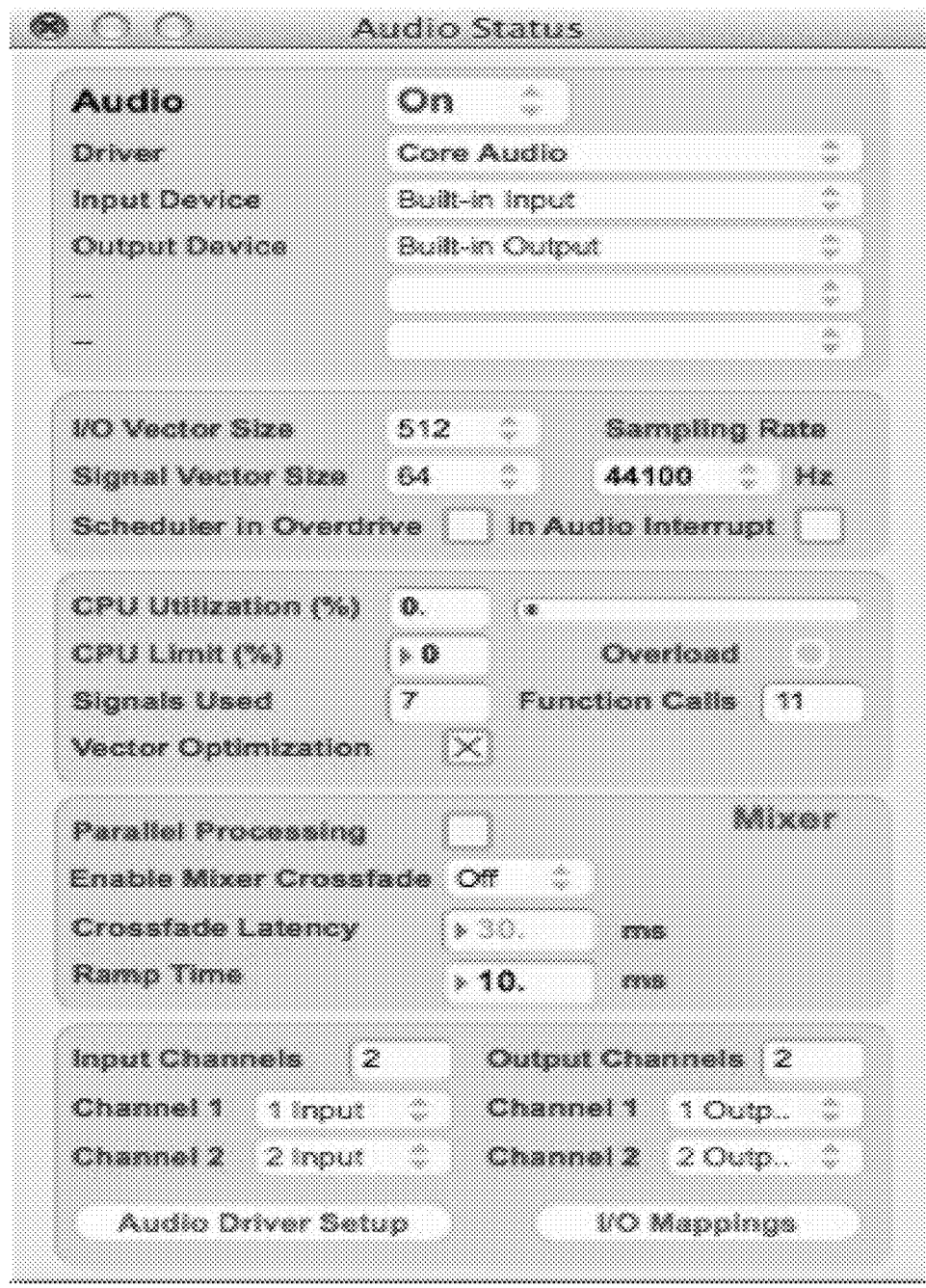
FIG. 3 depicts audio status for use in a sound association test according to an embodiment of the present disclosure.

The "Audio Settings" button opens up a page for the setting of all parameters relating to the use of audio. The "Audio Status" section (see FIG. 3) allows one to choose the audio "Input Device" as well as audio "Output Device". One can use the laptop computer microphone or choose from a variety of other microphones and sample rates. This window displays additional important information concerning recording parameters. Note that increased sample rates also will require more hard disk space. (See FIG. 3. Audio Status).

Figure 4:
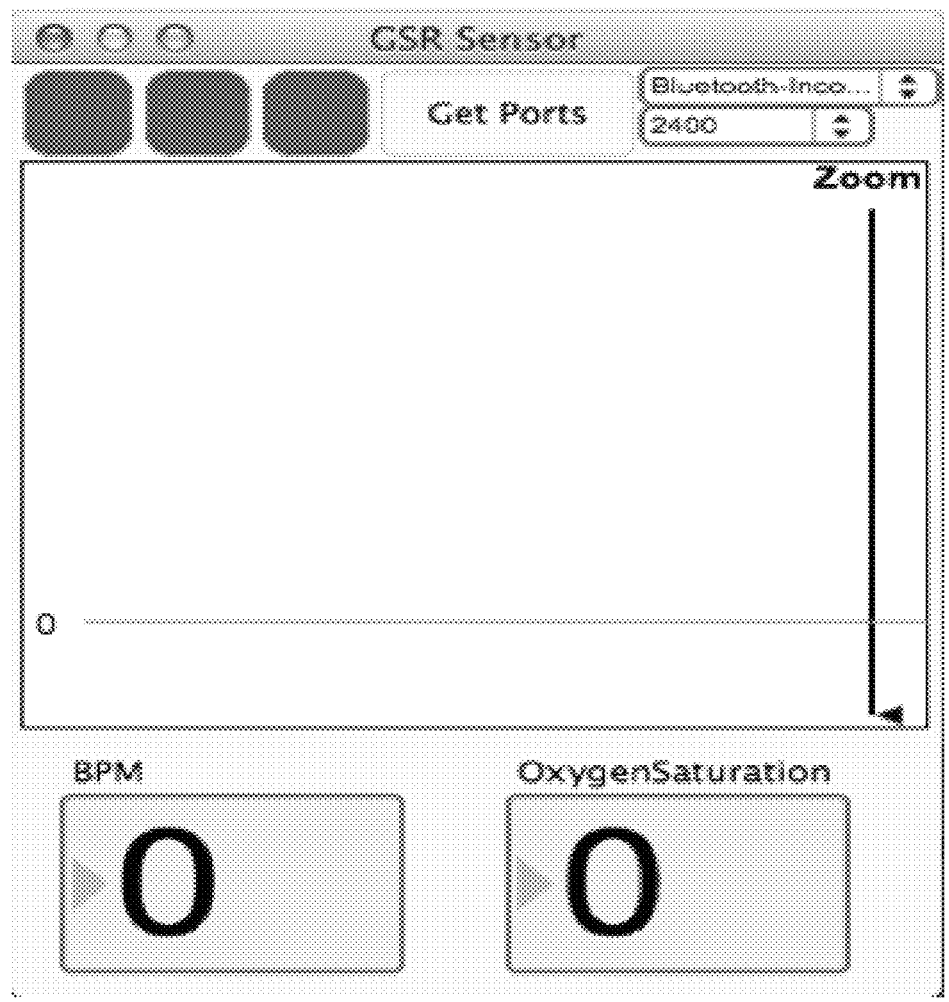
FIG. 4 depicts a GSR sensor for use in a sound association test according to an embodiment of the present disclosure.
Figure 6:
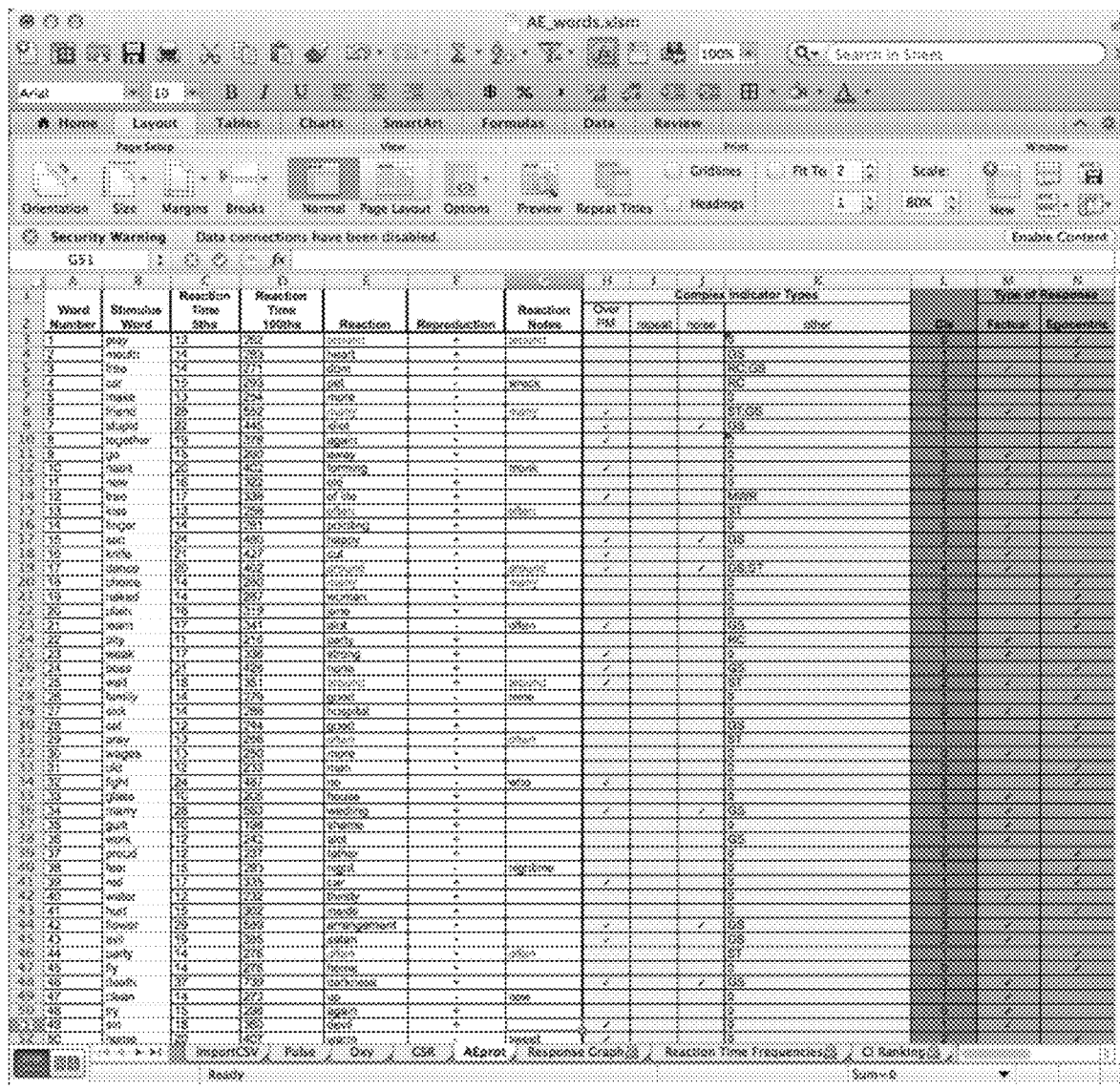
FIG. 6 depicts a sample Excel sheet for use in a sound association test according to an embodiment of the present disclosure.
Figure 8:
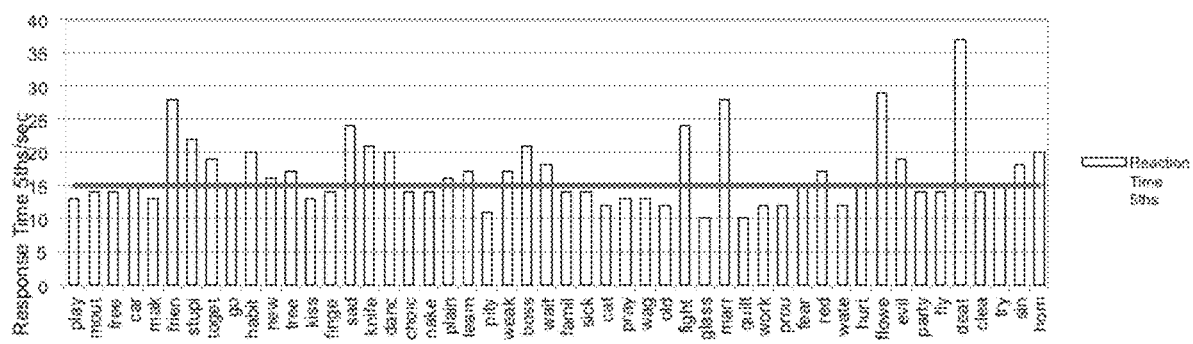
FIG. 8 depicts a graph of response times in a sound association test according to an embodiment of the present disclosure.

Returning to the main "Menu" window (FIG. 1) one can then use the "Sensor" button to access the "GSR Sensor" window (See FIG. 4). The "GSR Sensor" window is used to activate the physiological measuring devices data to be used. The "Gets Ports" button recognizes and activates the devises being used. All sensor data connects to an interface created specifically to work with Mac computer and the current software application. The interface is connected to the computer via USB. The selection for the input connection for the interface device is located in upper right hand corner of the "GSR Sensor" window. Another window directly bellow, allows for the resolution index to be set. Inside the "GSR Sensor" window we see we see the measured physiological components; BPM (beats per minute), Oxygen (in body saturation content), and Galvanic Skin Response (GSR) indicated on the graph. The inclusion of sensor data is an additional design element that was added to reintroduce the use of certain measurements of physiological data evident in Jung's original word association test. It is envisioned that the inclusion of physiological data will help the identification complex indicators that may not be visually apparent. For a full discussion of the use of biometric data in this sample population see section on physiological data below.

Returning to the main "Menu" (FIG. 1) one can initiate a study by choosing the "new study" button. Selecting this button brings forth a prompt to name the test. The naming of a study creates a file on the desktop in which all information pertinent to that study will be held. One can see that the application page looks like an Excel "Spreadsheet" with multiple fields and columns (see FIG. 5). This initial page appears as a copy of the final excel sheet in which all data will be gathered. The choice of this initial page was made for ease of use in that the general user will likely be more familiar with an excel layout than with the internal layout of the object oriented MAX program from IRCAM.

In this initial spreadsheet one can see that the test is divided into two components, "Words" and "Sounds" indicated in the top bar column of the test. The examiner can choose whether one will begin with the word association or choose the sound association portion of the test by clicking in the corresponding bar. The current application defaults to begin with the word association test. The current design presents the stimulus words via digital recording of the words. The examiner has the choice to use these existing vocal recordings or use the "mute" function and administer the words themselves. The inclusion of the vocal samples was a design consideration meant to explore the possibility of making the Word Association Test available in multiple languages. Examples of tests presented for this research have used the vocal recording default and begin with the word association test.

The main page "spreadsheet" (FIG. 5) contains the data fields relevant to the test.

Table 1. Data Field Contents

Data fields include:
1. Word/Sound number
2. Stimulus word/sound
3. Reaction time in 5ths
4. Reaction time in 100ths
5. Reaction
6. Reproduction
7. Reaction notes And Complex indicator section:
1. Sample time over PM
2. Repeat
3. Noise
4. Other
5. CI column (number of complex indicators)

Type of Response
1. Factual
2. Egocentric

Physiological Data
1. GSR—Galvanic skin response
2. Pulse
3. Oxygen

The physiological data includes Galvanic Skin Response (GSR), pulse rate, and oxygen content.

Appendix 2

List of Fifty Words

1) Play
2) Mouth
3) Free
4) Car
5) Make
6) Friend
7) Stupid
8) Together
9) Go
10) Habit
11) New
12) Tree
13) Kiss
14) Finger
15) Sad
16) Knife
17) Dance
18) Choice
19) Naked
20) Plain
21) Learn
22) Pity
23) Weak -continued 24) Boss
25) Wait
26) Family
27) Sick
28) Cat
29) Pray
30) Wages
31) Old
32) Fight
33) Glass
34) Marry
35) Guilt
36) Work
37) Proud
38) Fear
39) Red
40) Water
41) Hurt
42) Flower
43) Evil
44) Party
45) Fly
46) Death
47) Clean
48) Try
49) Sin
50) Home Appendix 2—Continued List of Fifty Sounds Categories:
AMB=Ambiguous
AN=Animal
HU=Human
OB=Object
NA=Nature
UR=Urban
Sounds:

1) AMB_Bayle
2) AN_bird
3) HU_sick
4) OB_phone
5) NA_river
6) OB_door
7) AMB_Diaz16
8) AN_rooster
9) UR_traffic
10) OB_cooking
11) HU_sing
12) AMB_Gobeil
13) HU_laugh
14) AN_dog
15) HU_walk
16) NA_rain
17) AMB_Diaz19
18) AN_cow
19) HU_sex
20) AN_wolf
21) OB_bells
22) HU_bride
23) AN_pig
24) HU_applause
25) UR_siren
26) NA_thunderstorm
27) AMB_Berio
28) AN_owl
29) HU_kiss
30) OB_ice
31) NA_wind
32) AMB_Diaz22

33) UR_train
34) OB_shots
35) HU_scream
36) UR_accident
37) UR_siren
38) AN_cat
39) HU_laugh
40) OB_teapot
41) NA_waves
42) UR_airport
43) AMV_Diaz15
44) AN_crickets
45) HU_breath
46) OB_ship
47) UR_jackhammer
48) AMB_Diaz16
49) AN_frog
50) SCN_storm Operating Instructions Implementation:

One begins by double click on the application icon currently identified as AT_27_v50. This opens and makes active the main "menu" (FIG. 1).

Chose "On/Off" options for camera and audio.

Next one proceeds to the "settings" button to set the parameters for the hardware to be used with the test. A refresh input list can be used to clear previous settings. All video settings are completed in this window.

Proceed to the audio button and set audio recording parameters and choice for the audio equipment to be used.

If biometric data is to be used connect the interface and devices to be used. Press "Sensor" button to calibrate and recognize the instruments.

[Note all devices are connected to the software program via USB ports].

Figure 5:
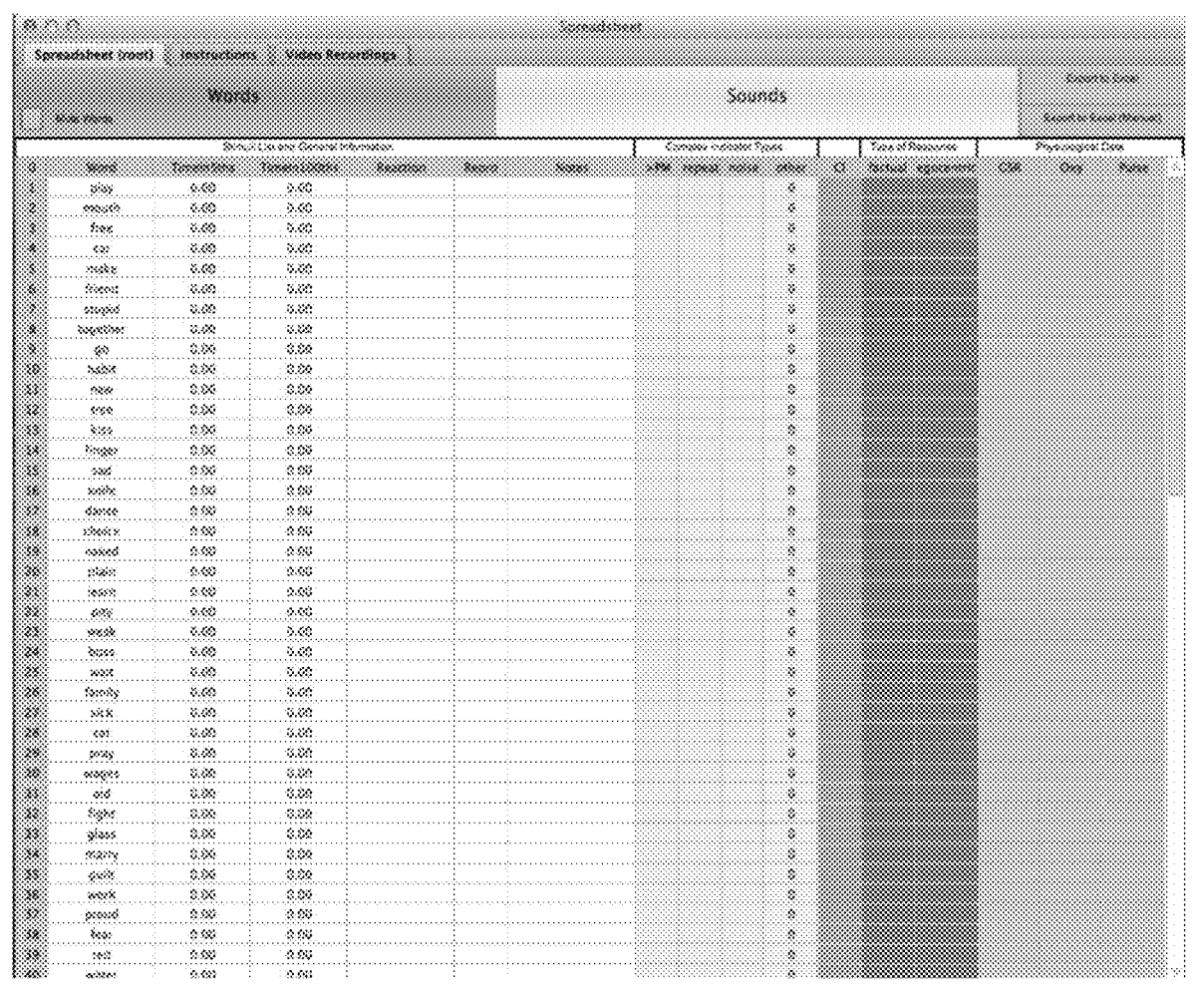

Once all settings have been established, one is ready to begin the test. Next, click on "New Study" to bring forth and activate main "Spreadsheet" application window (FIG. 5).

One can chose to administer either the "word" or "sound" portion of the test. The default is to start with the "word" portion of the test.

You will be prompted to name the test. The default naming is "AT_SubjectXX_Test#x". Name the test according to preferences. This creates a folder in which all information for the test, both words and sounds, will be saved. This action will initialize an "excel" spreadsheet window.

In the "Menu" window chose "Record A" by clicking on it. The record button becomes "red" indicating active status. The elapsed time indicator begins to function showing elapsed time. This record function will remain "On" throughout the entire recording of the first trial.

Next click on the first stimulus word in the word column. The word becomes "red" indicating that it is active and ready to be played. (Use "mute" button if digital recording of words will not be used. Default is to use digital recording of words).

While the stimulus word is "red" press the space bar to play the sound and press the spacebar again upon the completion of the subject's reaction. The pressing of the spacebar for "play" and again for "stop" records the time of the reaction response. The response time will be indicated in the appropriate column in 5ths and 100th.

Next double click in the reaction window and write in the reaction word. Press enter.

Proceed to next stimulus word in the column. Click on the next word. The word will turn "red" indicating that it is active and ready to be played. While the stimulus word is "red" press the space bar to play the sound and press the spacebar again upon the completion of the subject's reaction. The pressing of the spacebar for "play" and again for "stop" records the time of the reaction response. The response time will be indicated in the appropriate column in 5ths and 100th.

Proceed in similar fashion through all fifty (50) stimulus words for the first trial.

When done with the first trial press "Record A" again to stop recording for that portion of the test. The contents of the recording are automatically saved within the initial folder named at the start of the test.

To commence the second trial, find "Record B" in the "Menu" window and chose "Record B" by clicking on it. (The main spreadsheet is still active).

The record button becomes "red" indicating active status. The elapsed time indicator begins to function showing elapsed time. This "Record B" function will remain "On" throughout the entire recording of the first trial. The "Record B" function does not provide a timing of the response.

Next click on the first stimulus word in the word column. (Use "mute" button if digital recording of words will not be used). The word becomes "red" indicating that it is active and ready to be played.

While the stimulus word "red" press the space bar to play the stimulus word/sound and press the spacebar again upon the completion of the subjects reaction.

Next double click in the "Reproduction" column and insert a "+" or "−" for positive or false reproduction. Choose to double click in "notes" column to write and make note of the false reproduction. Any other observation can be input in the "notes" column as well. When done Press enter.

Proceed in similar fashion through all fifty (50) second trial reproduction of the words.

When done with the second trial press "Record B" again to stop recording for that portion of the test. The contents of the recording are automatically save within the initial folder named at the start of the test.

Do not exit application. When done "Export to Excel" and save.

The entire above procedure is repeated for the Sound portions of the test by selecting the sound portion of the test. The procedure is the same with the exception of the importation of the sound file.

Return again to the main spreadsheet window.

Click in the "Sound" portion of the test.

In the "menu" click on the "Read Folder" button. Choose the sound folder to be used. Currently this folder resides on the desktop and is identified as "Mastersounds50". Once file has been chosen, Click and choose OK.

Return to main application window and press the "sound" bar in the main window to activate and input the sound file.

Proceed with the test in similar fashion as with the word portion of the test.

"Record A" is used for the first trial and "record B" is used for the second trial. "Export to Excel" when done and save.

All information will be contained within the file named at the beginning of the test.

END.

Appendix 3

Subject Complex Indicator Ratings

Word Rankings Subject 1
Sounds CI Ranking Subject 1

| Sound Number | Stimulus Sound | Reaction | CIs |
|---|---|---|---|
| 34 | OB_shots | Fear uncomfortable | 5 |
| 36 | UR_accident | Oh horrible accident | 5 |
| 11 | HU_sing | Lady singing | 4 |
| 32 | AMB_Diaz22 | Annoying monotone | 4 |
| 6 | OB_door | Creaking door opening | 3 |
| 10 | OB_cooking | Peeing . . . can't describe | 3 |
| 12 | AMB_Gobeil | Haunted house . . . or dinosaur | 3 |
| 15 | HU_walk | Walking through mud in woods | 3 |
| 19 | HU_sex | Fearful . . . running . . . distress | 3 |
| 23 | AN_pig | Dog eating bone . . . hunger | 3 |
| 31 | NA_wind | Peaceful breeze | 3 |
| 40 | OB_teapot | Bird like ear piercing | 3 |
| 44 | AN_crickets | Rainforest . . . frogs | 3 |
| 2 | AN_bird | Rainforest | 2 |
| 5 | NA_river | Calmness | 2 |
| 7 | AMB_Diaz16 | Fear . . . scary | 2 |
| 8 | AN_rooster | Farm life | 2 |
| 9 | UR_traffic | Busy . . . chaos | 2 |
| 13 | HU_laugh | Fun . . . joy . . . dancing | 2 |
| 16 | NA_rain | Peace . . . waterfall | 2 |
| 18 | AN_cow | Slaughter house | 2 |
| 21 | OB_bells | Huge church . . . beautiful bells | 2 |
| 27 | AMB_berio | Insanity | 2 |
| 28 | AN_owl | Outdoors | 2 |
| 38 | AN_cat | Sweetness kitten | 2 |
| 39 | HU_laugh | Funny . . . fun | 2 |
| 41 | NA_waves | Peaceful | 2 |
| 49 | AN_frog | A lake or a swamp | 2 |
| 1 | AMB_Bayle | Bells | 1 |
| 3 | HU_sick | Sickness | 1 |
| 17 | AMB_Diaz19 | Mystery . . . intrigue | 1 |
| 20 | AN_wolf | Cold night | 1 |
| 22 | HU_bride | Carrousel . . . children | 1 |
| 25 | UR_siren | Fear . . . run | 1 |
| 30 | OB_ice | Refreshing | 1 |
| 33 | UR_train | Repetitive | 1 |
| 37 | UR_siren | Unknown | 1 |
| 42 | UR_airport | Excitement | 1 |
| 45 | HU_breath | Lust . . . love | 1 |
| 46 | OB_ship | Water . . . seagulls | 1 |
| 48 | AMB_Diaz16 | Stalking | 1 |
| 50 | SCN_storm | Freedom | 1 |

Subject 2

Words CI Rankings

| Word Number | Stimulus word | Reaction | CIs |
|---|---|---|---|
| 34 | Marry | Go round | 5 |
| 5 | Make | That's weird | 4 |
| 7 | Stupid | Um 0 slow | 3 |
| 8 | Together | World | 3 |
| 11 | New | Shoes | 3 |
| 20 | Plain | Like . . . Air cloud | 3 |
| 38 | Fear | Dark n | 3 |
| 41 | Hurt | Heal | 3 |
| 14 | Finger | Ring | 2 |
| 17 | Dance | Left foot | 2 |
| 19 | Naked | Woman | 2 |
| 37 | Proud | Accomplishment | 2 |
| 46 | Death | Loud | 2 |
| 49 | Sin | Um judge | 2 |
| 50 | Home | Comfort | 2 |
| 1 | Play | Ground | 1 |
| 3 | Free | Bird | 1 |
| 21 | Learn | More | 1 |
| 23 | Weak | Mouse | 1 |
| 25 | Wait | Gain | 1 |
| 26 | Family | Together | 1 |
| 32 | Fight | Lots | 1 |
| 36 | Work | Love | 1 |
| 43 | Evil | Lie | 1 |
| 45 | Fly | Knat | 1 |
| 47 | Clean | Relaxing | 1 |

Sounds—CI Rankings Subject 2

| Sound Number | Stimulus Sound | Reaction | CIs |
|---|---|---|---|
| 12 | AMB_Gobeil | Clock | 5 |
| 37 | UR_siren | Ambulance | 4 |
| 4 | OB_phone | Phone call | 3 |
| 6 | OB_door | Sneaky | 3 |
| 14 | AN_dog | Neighborhood | 3 |
| 18 | AN_cow | (Ha-ha) cow | 3 |
| 19 | HU_sex | (Ha-ha) sex | 3 |
| 32 | AMB_Diaz22 | Floating | 3 |
| 33 | UR_train | Train tracks | 3 |
| 36 | UR_accident | Stop | 3 |
| 44 | AN_crickets | Spring time | 3 |
| 47 | UR_jackhammer | Alarm clock wake up | 3 |
| 2 | AN_bird | Beach 0 forest | 2 |
| 3 | HU_sick | Danger | 2 |
| 7 | AMB_Diaz16 | Thunder | 2 |
| 9 | UR_traffic | No thank you | 2 |
| 13 | HU_laugh | Crowd | 2 |
| 15 | HU_walk | Potato chip | 2 |
| 27 | AMB_berio | Cold | 2 |
| 30 | OB_ice | Thirsty | 2 |
| 31 | NA_wind | Skyscraper | 2 |
| 39 | HU_laugh | Busy | 2 |
| 41 | NA_waves | Salt water | 2 |
| 42 | UR_airport | Trip | 2 |
| 49 | AN_frog | Frog | 2 |
| 5 | NA_river | That's a creek | 1 |
| 8 | AN_rooster | Good morning | 1 |
| 11 | HU_sing | Bush land | 1 |
| 17 | AMB_Diaz19 | Aliens | 1 |
| 22 | HU_bride | Busy | 1 |
| 23 | AN_pig | Slop | 1 |
| 25 | UR_siren | City | 1 |
| 26 | NA_thunderstorm | Porch | 1 |
| 34 | OB_shots | (Ha-ha) video games | 1 |
| 35 | HU_scream | Pain | 1 |
| 38 | AN_cat | Puppy | 1 |
| 40 | OB_teapot | Tea kettle | 1 |
| 43 | AMB_Diaz15 | Loose connection | 1 |
| 45 | HU_breath | Exercise? | 1 |
| 48 | AMB_Diaz16 | Impatient | 1 |

Subject 3

Words—CI Rankings

| Word Number | Stimulus Word | Reaction | CIs |
|---|---|---|---|
| 20 | Plain | Path | 4 |
| 35 | Guilt | Complex | 4 |
| 50 | Home | Looking for one | 4 |

-continued

| Word Number | Stimulus Word | Reaction | CIs |
|---|---|---|---|
| 3 | Free | Free, free | 3 |
| 5 | Make | Create | 3 |
| 21 | Learn | Progress | 3 |
| 25 | Wait | Anxiety | 3 |
| 34 | Marry | Sam - mis (names) | 3 |
| 38 | Fear | No more | 3 |
| 42 | Flower | Fragrant | 3 |
| 45 | Fly | Freedom (insect fly) | 3 |
| 49 | Sin | Evil | 3 |
| 4 | Car | Escape | 2 |
| 7 | Stupid | Nobody | 2 |
| 8 | Together | Family | 2 |
| 10 | Habit | Day | 2 |
| 11 | New | Life | 2 |
| 12 | Tree | Life | 2 |
| 15 | Sad | Emotion | 2 |
| 22 | Pity | No | 2 |
| 24 | Boss | Control | 2 |
| 26 | Family | None | 2 |
| 32 | Fight | Determined | 2 |
| 40 | Water | Fall | 2 |
| 46 | Death | Everyone | 2 |
| 48 | Try | Effort | 2 |
| 1 | Play | Fun | 1 |
| 2 | Mouth | Dog | 1 |
| 6 | Friend | Love | 1 |
| 13 | Kiss | Expression | 1 |
| 16 | Knife | Girl (nice) | 1 |
| 18 | Choice | Me | 1 |
| 23 | Weak | Normal | 1 |
| 27 | Sick | Health | 1 |
| 29 | Pray | Spirit | 1 |
| 37 | Proud | History | 1 |
| 39 | Red | Blue | 1 |
| 41 | Hurt | Pain | 1 |
| 44 | Party | Fun | 1 |
| 47 | Clean | Dirty | 1 |

Subject 3

Sounds—CI Ranking

| Sound Number | Stimulus Sound | Reaction | CIs |
|---|---|---|---|
| 34 | OB_shots | Frightening | 5 |
| 18 | AN_cow | Cattle | 4 |
| 26 | NA_thunderstorm | Dark clouds | 4 |
| 32 | AMB_Diaz22 | Deep | 4 |
| 41 | NA_waves | Noise cancelation | 4 |
| 6 | OB_door | Noise weird | 3 |
| 11 | HU_sing | Beautiful | 3 |
| 17 | AMB_Diaz19 | Eerie | 3 |
| 25 | UR_siren | Pain | 3 |
| 33 | UR_train | Terrifying | 3 |
| 36 | UR_accident | Impact . . . Ahhh trauma | 3 |
| 38 | AN_cat | Sympathy | 3 |
| 43 | AMB_Diaz15 | Distracting | 3 |
| 44 | AN_crickets | Enjoyable | 3 |
| 46 | OB_ship | Pleasurable | 3 |
| 1 | AMB_Bayle | Sunday | 2 |
| 2 | AN_bird | Nature | 2 |
| 4 | OB_phone | Cellphone annoyance | 2 |
| 5 | NA_river | Hum serene | 2 |
| 8 | AN_rooster | Neighbors | 2 |
| 9 | UR_traffic | San Francisco | 2 |
| 12 | AMB_Gobeil | A cave | 2 |
| 13 | HU_laugh | Party | 2 |
| 15 | HU_walk | Fresh snow | 2 |

-continued

| Sound Number | Stimulus Sound | Reaction | CIs |
|---|---|---|---|
| 19 | HU_sex | Childhood | 2 |
| 20 | AN_wolf | Rest eye closed | 2 |
| 21 | OB_bells | Wedding | 2 |
| 22 | HU_bride | Practice | 2 |
| 23 | AN_pig | Indulge | 2 |
| 27 | AMB_berio | Suffering | 2 |
| 28 | AN_owl | Calm | 2 |
| 31 | NA_wind | Alone | 2 |
| 35 | HU_scream | Torture x2 | 2 |
| 39 | HU_laugh | Enjoyment | 2 |
| 40 | OB_teapot | Piercing | 2 |
| 45 | HU_breath | Sex passion | 2 |
| 3 | HU_sick | Irritated | 1 |
| 7 | AMB_Diaz16 | Kids | 1 |
| 10 | OB_cooking | Cooking | 1 |
| 14 | AN_dog | Baxter | 1 |
| 24 | HU_applause | Appreciation | 1 |
| 37 | UR_siren | Help | 1 |
| 47 | UR_jackhammer | Work | 1 |
| 49 | AN_frog | Autumn | 1 |
| 50 | SCN_storm | Energy | 1 |

Subject 4

Words CI Ranking

| Word Number | Stimulus Word | Reaction | CIs |
|---|---|---|---|
| 5 | Make | Shirt/camisa | 5 |
| 25 | Wait | For the train | 5 |
| 29 | Pray | Meat | 5 |
| 17 | Dance | Twin peaks | 4 |
| 48 | Try | To success | 4 |
| 50 | Home | Field | 4 |
| 21 | Learn | To dance | 3 |
| 26 | Family | Teddy bear | 3 |
| 28 | Cat | Guess | 3 |
| 30 | Wages | Chairs | 3 |
| 33 | Glass | Water | 3 |
| 1 | Play | Jugar | 2 |
| 4 | Car | Auto | 2 |
| 6 | Friend | Wolf | 2 |
| 7 | Stupid | Cow | 2 |
| 9 | Go | Pro | 2 |
| 14 | Finger | Nail | 2 |
| 15 | Sad | Horse | 2 |
| 20 | Plain | Bomb | 2 |
| 27 | Sick | Dog | 2 |
| 32 | Fight | Neighborhood | 2 |
| 34 | Marry | Jane | 2 |
| 37 | Proud | Eagle | 2 |
| 40 | Water | Lake | 2 |
| 2 | Mouth | Table | 1 |
| 3 | Free | Beer | 1 |
| 8 | Together | Beatles | 1 |
| 12 | Tree | Cherry | 1 |
| 22 | Pity | Dog | 1 |
| 23 | Weak | Strong | 1 |
| 31 | Old | Ancient | 1 |
| 35 | Guilt | Digger | 1 |
| 36 | Work | No fun | 1 |
| 38 | Fear | Monster | 1 |
| 39 | Red | Mayonnaise | 1 |
| 43 | Evil | Kennevil | 1 |

Subject 4

Sounds CI Rankings

| Sound Number | Stimulus Sound | Reaction | CIs |
|---|---|---|---|
| 20 | AN_wolf | Don't know | 5 |
| 39 | HU_laugh | Don't know | 4 |
| 7 | AMB_Diaz16 | Cold | 3 |
| 8 | AN_rooster | Chicken | 3 |
| 12 | AMB_Gobeil | Train | 3 |
| 15 | HU_walk | Ice | 3 |
| 17 | AMB_Diaz19 | Risset (med a name) | 3 |
| 19 | HU_sex | Sex | 3 |
| 24 | HU_applause | Sad | 3 |
| 49 | AN_frog | Insect . . . ducks | 3 |
| 1 | AMB_Bayle | Campana | 2 |
| 5 | NA_river | Wet | 2 |
| 10 | OB_cooking | Frying | 2 |
| 11 | HU_sing | Death | 2 |
| 16 | NA_rain | River | 2 |
| 22 | HU_bride | Married | 2 |
| 27 | AMB_berio | Berio - id | 2 |
| 28 | AN_owl | Cat | 2 |
| 29 | HU_kiss | Dog | 2 |
| 31 | NA_wind | Cold | 2 |
| 33 | UR_train | Busy | 2 |
| 42 | UR_airport | Fly | 2 |
| 44 | AN_crickets | Incests . . . bugs | 2 |
| 45 | HU_breath | Sex | 2 |
| 46 | OB_ship | Lake | 2 |
| 48 | AMB_Diaz16 | Heartbeat | 2 |
| 50 | SCN_storm | Cold | 2 |
| 2 | AN_bird | Insectos | 1 |
| 3 | HU_sick | Sick | 1 |
| 9 | UR_traffic | Busy | 1 |
| 18 | AN_cow | Meat | 1 |
| 23 | AN_pig | Food | 1 |
| 25 | UR_siren | Police | 1 |
| 26 | NA_thunderstorm | Storm | 1 |
| 32 | AMB_Diaz22 | Movie | 1 |
| 34 | OB_shots | Video game | 1 |
| 37 | UR_siren | Police | 1 |
| 40 | OB_teapot | Tea | 1 |

Subject 5

Words CI Rankings

| Word Number | Stimulus Word | Reaction | CIs |
|---|---|---|---|
| 2 | Mouth | Eating | 4 |
| 30 | Wages | Language work (que es?) | 4 |
| 31 | Old | Building | 4 |
| 34 | Marry | Challenge (Mari) | 4 |
| 46 | Death | Mystery | 4 |
| 3 | Free | What is it? | 3 |
| 17 | Dance | With who | 3 |
| 18 | Choice | Of what | 3 |
| 20 | Plain | Trip | 3 |
| 22 | Pity | Of who? | 3 |
| 25 | Wait | Now | 3 |
| 32 | Fight | How? | 3 |
| 35 | Guilt | Killing | 3 |
| 49 | Sin | Wound | 3 |
| 7 | Stupid | Stupid | 2 |
| 12 | Tree | Of life | 2 |
| 15 | Sad | Tear | 2 |
| 16 | Knife | Kill | 2 |
| 28 | Cat | Fear | 2 |
| 37 | Proud | Of who | 2 |
| 41 | Hurt | Wound | 2 |
| 48 | Try | What | 2 |
| 1 | Play | Freedom | 1 |
| 5 | Make | What | 1 |
| 6 | Friend | Warmth | 1 |
| 8 | Together | Careful | 1 |
| 10 | Habit | Routine | 1 |
| 13 | Kiss | Who? | 1 |
| 14 | Finger | Print | 1 |
| 19 | Naked | Exposed | 1 |
| 23 | Weak | Father | 1 |
| 24 | Boss | School | 1 |
| 26 | Family | Troubles | 1 |
| 29 | Pray | For hope | 1 |
| 38 | Fear | Black | 1 |
| 39 | Red | Fire | 1 |
| 42 | Flower | Spring | 1 |
| 43 | Evil | Teacher | 1 |
| 45 | Fly | Dangerous | 1 |

Subject 5

Sounds CI Ranking

| Sound Number | Stimulus Sound | Reaction | CIs |
|---|---|---|---|
| 7 | AMB_Diaz16 | Yawning | 5 |
| 35 | HU_scream | Loneliness | 5 |
| 12 | AMB_Gobeil | Noche | 4 |
| 27 | AMB_berio | No se | 4 |
| 39 | HU_laugh | No se | 4 |
| 40 | OB_teapot | Muy desagradable el sonido | 4 |
| 41 | NA_waves | By the sea | 4 |
| 45 | HU_breath | Despair | 4 |
| 48 | AMB_Diaz16 | Night memory | 4 |
| 4 | OB_phone | IPhone ringing | 3 |
| 15 | HU_walk | Broken ice | 3 |
| 19 | HU_sex | Giving birth | 3 |
| 22 | HU_bride | Boda | 3 |
| 28 | AN_owl | Noche | 3 |
| 31 | NA_wind | Night storm | 3 |
| 32 | AMB_Diaz22 | Organo | 3 |
| 33 | UR_train | Too loud | 3 |
| 38 | AN_cat | Kitten | 3 |
| 43 | AMB_Diaz15 | Muy desagrable | 3 |
| 44 | AN_crickets | Street at night | 3 |
| 46 | OB_ship | Train station in Europe | 3 |
| 49 | AN_frog | Noche en el campo | 3 |
| 50 | SCN_storm | Horseback riding in the night | 3 |
| 1 | AMB_Bayle | Church bells | 2 |
| 6 | OB_door | Puerta en casa del terror | 2 |
| 9 | UR_traffic | 0 yawning chaos | 2 |
| 10 | OB_cooking | Freir | 2 |
| 20 | AN_wolf | Campo | 2 |
| 26 | NA_thunderstorm | Night storm | 2 |
| 29 | HU_kiss | Beso | 2 |
| 30 | OB_ice | Fresh water | 2 |
| 34 | OB_shots | Guerra | 2 |
| 36 | UR_accident | End | 2 |
| 2 | AN_bird | Mosca molesta | 1 |
| 3 | HU_sick | Ahogo | 1 |
| 5 | NA_river | Arroyo | 1 |
| 8 | AN_rooster | Mañana | 1 |
| 14 | AN_dog | Guardia | 1 |
| 16 | NA_rain | Lluvia | 1 |
| 17 | AMB_Diaz19 | Expansion | 1 |
| 18 | AN_cow | Tambo (cow milking) | 1 |
| 23 | AN_pig | Chiquero | 1 |
| 37 | UR_siren | No sense | 1 |
| 42 | UR_airport | Farewell | 1 |
| 47 | UR_jackhammer | Wake up | 1 |

Subject 6

Words CI Rankings

| Word Number | Stimulus Word | Reaction | CIs |
|---|---|---|---|
| 17 | Dance | Around | 4 |
| 6 | Friend | Many | 3 |
| 7 | Stupid | Idiot | 3 |
| 15 | Sad | Happy | 3 |
| 21 | Learn | A lot | 3 |
| 34 | Marry | Wedding | 3 |
| 42 | Flower | Arrangement | 3 |
| 46 | Death | Darkness | 3 |
| 3 | Free | Dom | 2 |
| 4 | Car | Pet | 2 |
| 10 | Habit | Forming | 2 |
| 12 | Tree | Of life | 2 |
| 24 | Boss | None | 2 |
| 25 | Wait | Around | 2 |
| 32 | Fight | No | 2 |
| 43 | Evil | Satan | 2 |
| 50 | Home | Warm | 2 |
| 2 | Mouth | Heart | 1 |
| 8 | Together | Again | 1 |
| 13 | Kiss | Often | 1 |
| 16 | Knife | Cut | 1 |
| 22 | Pity | Party | 1 |
| 23 | Weak | Strong | 1 |
| 26 | Family | Good | 1 |
| 28 | Cat | Good | 1 |
| 29 | Pray | Often | 1 |
| 36 | Work | A lot | 1 |
| 38 | Fear | Night | 1 |
| 39 | Red | Car | 1 |
| 44 | Party | Often | 1 |
| 47 | Clean | Up | 1 |
| 49 | Sin | Devil | 1 |

Subject 6

Sounds CI Rankings

| Sound Number | Stimulus Sound | Reaction | CIs |
|---|---|---|---|
| 36 | UR_accident | Oh. Accident | 5 |
| 27 | AMB_berio | Insane | 4 |
| 6 | OB_door | Dungeon | 3 |
| 14 | AN_dog | Neighborhood | 3 |
| 15 | HU_walk | Walking on leaves | 3 |
| 18 | AN_cow | Cattle | 3 |
| 22 | HU_bride | Wedding | 3 |
| 23 | AN_pig | Sty; pigsty | 3 |
| 29 | HU_kiss | Kissing | 3 |
| 50 | SCN_storm | Voyage | 3 |
| 4 | OB_phone | Not again | 2 |
| 5 | NA_river | River | 2 |
| 11 | HU_sing | Indian | 2 |
| 12 | AMB_Gobeil | Solitary | 2 |
| 17 | AMB_Diaz19 | UFO | 2 |
| 19 | HU_sex | Good | 2 |
| 20 | AN_wolf | Lonely | 2 |
| 32 | AMB_Diaz22 | Floating | 2 |
| 33 | UR_train | Cargo | 2 |
| 35 | HU_scream | Torture | 2 |
| 41 | NA_waves | Distance | 2 |
| 48 | AMB_Diaz16 | Marching | 2 |
| 49 | AN_frog | Pond | 2 |
| 1 | AMB_Bayle | Bells | 1 |
| 3 | HU_sick | Coughing | 1 |
| 7 | AMB_Diaz16 | Footsteps | 1 |
| 8 | AN_rooster | Chores | 1 |
| 9 | UR_traffic | 5oclock | 1 |
| 16 | NA_rain | Shower | 1 |
| 30 | OB_ice | Cocktail | 1 |
| 31 | NA_wind | Desert | 1 |
| 34 | OB_shots | War | 1 |
| 38 | AN_cat | Kitty cat | 1 |
| 43 | AMB_Diaz15 | Electric | 1 |
| 44 | AN_crickets | Rainforest | 1 |
| 45 | HU_breath | Out of breath | 1 |
| 46 | OB_ship | Fog | 1 |

Subject 7

Words CI Rankings

| Word Number | Stimulus Word | Reaction | CIs |
|---|---|---|---|
| 35 | Guilt | Sadness | 5 |
| 10 | Habit | Don't understand | 4 |
| 20 | Plain | Jumping | 4 |
| 46 | Death | Sad | 4 |
| 2 | Mouth | Mouse | 3 |
| 7 | Stupid | Friends | 3 |
| 3 | Free | Playing | 2 |
| 8 | Together | Groups | 2 |
| 12 | Tree | Branches | 2 |
| 14 | Finger | Stimulus | 2 |
| 26 | Family | People | 2 |
| 28 | Cat | Dog | 2 |
| 32 | Fight | Fire | 2 |
| 36 | Work | Strong | 2 |
| 41 | Hurt | Sadness | 2 |
| 47 | Clean | Chemicals | 2 |
| 48 | Try | Harder | 2 |
| 1 | Play | Dancing | 1 |
| 6 | Friend | People | 1 |
| 13 | Kiss | Girlfriend | 1 |
| 17 | Dance | Free play | 1 |
| 21 | Learn | Many things | 1 |
| 22 | Pity | Sadness | 1 |
| 27 | Sick | Illness | 1 |
| 30 | Wages | Money | 1 |
| 31 | Old | Senior | 1 |
| 34 | Marry | Woman | 1 |
| 37 | Proud | Dog | 1 |
| 38 | Fear | Anxiety | 1 |
| 39 | Red | Flames | 1 |
| 45 | Fly | Flying around | 1 |
| 49 | Sin | Evil | 1 |

Subject 7

Sounds CI Rankings

| Word Number | Stimulus Word | Reaction | CIs |
|---|---|---|---|
| 16 | NA_rain | Eggs? | 4 |
| 24 | HU_applause | Applause | 4 |
| 27 | AMB_berio | Berio | 4 |
| 36 | UR_accident | Danger | 4 |
| 41 | NA_waves | Nighttime | 4 |
| 2 | AN_bird | Bird | 3 |
| 12 | AMB_Gobeil | Chaotic | 3 |
| 19 | HU_sex | Whispering | 3 |
| 28 | AN_owl | Owl | 3 |
| 44 | AN_crickets | Night jungle | 3 |

-continued

| Word Number | Stimulus Word | Reaction | CIs |
|---|---|---|---|
| 48 | AMB_Diaz16 | Depth code | 3 |
| 7 | AMB_Diaz16 | Empty | 2 |
| 8 | AN_rooster | Loud | 2 |
| 15 | HU_walk | Cutting | 2 |
| 18 | AN_cow | Farm | 2 |
| 23 | AN_pig | Smell | 2 |
| 29 | HU_kiss | Marriage | 2 |
| 30 | OB_ice | Glasses | 2 |
| 31 | NA_wind | Far away | 2 |
| 33 | UR_train | In the way | 2 |
| 34 | OB_shots | In trouble | 2 |
| 37 | UR_siren | In trouble | 2 |
| 38 | AN_cat | Small | 2 |
| 40 | OB_teapot | Teakettle | 2 |
| 42 | UR_airport | Airport | 2 |
| 47 | UR_jackhammer | Too much | 2 |
| 1 | AMB_Bayle | Bell | 1 |
| 4 | OB_phone | Phone | 1 |
| 5 | NA_river | Turbulence | 1 |
| 11 | HU_sing | Singing | 1 |
| 17 | AMB_Diaz19 | Sy fi | 1 |
| 22 | HU_bride | Pilgrimage | 1 |
| 25 | UR_siren | In trouble | 1 |
| 26 | NA_thunderstorm | Storm | 1 |
| 35 | HU_scream | Pain | 1 |
| 45 | HU_breath | Breathing | 1 |
| 46 | OB_ship | Fog horn | 1 |

Subject 8

Word CI Rankings

| Word Number | Stimulus Word | Reaction | CIs |
|---|---|---|---|
| 20 | Plain | Fly | 5 |
| 35 | Guilt | Guilty | 5 |
| 5 | Make | Bake | 4 |
| 32 | Fight | Gloves | 3 |
| 34 | Marry | Wed | 3 |
| 39 | Red | Butter | 3 |
| 42 | Flower | Scent | 3 |
| 3 | Free | Bird | 2 |
| 4 | Car | Ride | 2 |
| 7 | Stupid | Idiot | 2 |
| 10 | Habit | Nails | 2 |
| 11 | New | Clothes | 2 |
| 14 | Finger | Long | 2 |
| 19 | Naked | Bathrobe | 2 |
| 25 | Wait | Heavy | 2 |
| 44 | Party | Food | 2 |
| 48 | Try | Succeed | 2 |
| 2 | Mouth | Smile | 1 |
| 8 | Together | Band | 1 |
| 9 | Go | Speed | 1 |
| 12 | Tree | Green | 1 |
| 22 | Pity | Sad | 1 |
| 27 | Sick | Ill | 1 |
| 45 | Fly | Wall | 1 |

Subject 8

Sound CI Rankings

| Word Number | Stimulus Word | Reaction | CIs |
|---|---|---|---|
| 38 | AN_cat | Newborn | 5 |
| 15 | HU_walk | Packing bubbles | 4 |

-continued

| Word Number | Stimulus Word | Reaction | CIs |
|---|---|---|---|
| 48 | AMB_Diaz16 | First thing is basketball | 4 |
| 1 | AMB_Bayle | Beads | 3 |
| 10 | OB_cooking | Grill | 3 |
| 33 | UR_train | BNSF | 3 |
| 35 | HU_scream | Death metal | 3 |
| 40 | OB_teapot | Neighbor | 3 |
| 7 | AMB_Diaz16 | Helicopter | 2 |
| 8 | AN_rooster | Early morning | 2 |
| 12 | AMB_Gobeil | Basement | 2 |
| 13 | HU_child | Toddler | 2 |
| 18 | AN_cow | Cattle drive | 2 |
| 21 | OB_bells | London | 2 |
| 25 | UR_siren(2) | City | 2 |
| 26 | NA_thunderstorm | Danger | 2 |
| 28 | AN_owl | Quiet | 2 |
| 31 | NA_wind | Prairie | 2 |
| 32 | AMB_Diaz22 | 80's | 2 |
| 39 | HU_laugh | Jazz club | 2 |
| 45 | HU_breath | Annoying | 2 |
| 2 | AN_bird | Jungle | 1 |
| 3 | HU_sick | Sick | 1 |
| 4 | OB_phone | Cellphone | 1 |
| 5 | NA_river | Waterfall | 1 |
| 9 | UR_traffic | New york | 1 |
| 11 | HU_sing | Swedish | 1 |
| 16 | NA_rain | Shower | 1 |
| 17 | AMB_Diaz19 | Magical | 1 |
| 19 | HU_sex | Scared | 1 |
| 23 | AN_pig | Farm | 1 |
| 27 | AMB_berio | Theater | 1 |
| 29 | HU_kiss | Smooch | 1 |
| 30 | OB_ice | Cocktail | 1 |
| 36 | UR_accident | Insurance | 1 |
| 41 | NA_waves | Sleep | 1 |
| 42 | UR_airport | Airport | 1 |
| 44 | AN_crickets | Nature | 1 |
| 46 | OB_ship | Harbor | 1 |
| 47 | UR_jackhammer | City | 1 |

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method for sound association testing, the method comprising:
presenting the Jung traditional Word Association test alongside a sound association test which introduces sonic stimuli to inform of underlying psychological processes evident in a subject based upon responses to sonic stimuli, wherein the combination of the Jung traditional Word Association Test and the sound association test elicit associations that reveal unconscious material and provides additional information as complex indicators to discern psychological complexes through associations to auditory stimuli;

wherein the Jung traditional Word Association test and the sound association testing run on a single laptop computer using both, an object-oriented music programming software, and a spreadsheet program, the Jung traditional Word Association test and the sound association testing providing a compare and contrast scenario in psychological testing, wherein the object-oriented music programming software is configured to record the response time of the subject to both sounds and word;

calculating and exporting the mean response time to the spreadsheet program; and automatically creating a graph depicting the mean response time and the mean.

2. The method of claim 1 wherein the sonic stimuli are ambiguous and identifiable sound stimuli.

3. The method of claim 1 wherein the complex indicators include response time above average mean, no response to stimulus, different reproduction, repetition, identification of sound versus association, multiple word response, gestures, movement, laughter, stuttering, noises, rhymes, disconnected reactions, misunderstood sound, mediated response, and response in foreign language.

4. The method of claim 1 wherein the single laptop computer includes one or more of the following additional hardware components:
a video recorder, a microphone, headphones, and a digital interface for physiological data.

5. The method of claim 1 wherein the Jung traditional Word Association test includes at least fifty (50) word associations and the sound association test includes at least fifty (50) sound stimuli.

6. The method of claim 5 wherein the sound stimuli are classified by categories, the categories selected from the group comprising:
sounds of nature, human sounds, animal sounds, urban sounds, and ambiguous stimuli.

7. The method of claim 1 further comprising:
using audio and visual recording to record reactions to both words and sounds during the sound association testing.

8. The method of claim 1 further comprising:
monitoring and recording supplementary physiological data during the sound association testing, the supplementary physiological data including heart rate, oxygen response and galvanic skin response.

9. The method of claim 1 wherein the sound association test is administered using digital voice samples of stimulus words.

10. The method of claim 1 wherein the sound association test is administered by an administrator articulating stimulus words himself/herself.

* * * * *